(12) United States Patent
Warrell, Jr. et al.

(10) Patent No.: US 10,093,631 B2
(45) Date of Patent: Oct. 9, 2018

(54) BIFUNCTIONAL COMPOUNDS AND USE FOR REDUCING URIC ACID LEVELS

(71) Applicant: Acquist LLC, Westfield, NJ (US)

(72) Inventors: Raymond P. Warrell, Jr., Westfield, NJ (US); John J. Piwinski, Lebanon, NJ (US)

(73) Assignee: Acquist LLC, Westfield, NJ (US)

( * ) Notice: Subject to any disclaimer, the term of this patent is extended or adjusted under 35 U.S.C. 154(b) by 0 days.

(21) Appl. No.: 15/118,243

(22) PCT Filed: Jan. 22, 2015

(86) PCT No.: PCT/US2015/012370
§ 371 (c)(1),
(2) Date: Aug. 11, 2016

(87) PCT Pub. No.: WO2015/123003
PCT Pub. Date: Aug. 20, 2015

(65) Prior Publication Data
US 2017/0197923 A1 Jul. 13, 2017

Related U.S. Application Data

(60) Provisional application No. 61/939,818, filed on Feb. 14, 2014.

(51) Int. Cl.
| | | |
|---|---|---|
| A61K 31/506 | (2006.01) | |
| C07D 239/557 | (2006.01) | |
| C07D 413/12 | (2006.01) | |
| C07D 417/12 | (2006.01) | |
| C07D 403/12 | (2006.01) | |
| C07D 239/60 | (2006.01) | |
| C07D 413/04 | (2006.01) | |
| C07D 401/12 | (2006.01) | |

(52) U.S. Cl.
CPC ....... *C07D 239/557* (2013.01); *C07D 239/60* (2013.01); *C07D 401/12* (2013.01); *C07D 403/12* (2013.01); *C07D 413/04* (2013.01); *C07D 413/12* (2013.01); *C07D 417/12* (2013.01)

(58) Field of Classification Search
CPC .. C07D 239/62; C07D 239/64; C07D 239/66; C07D 239/68
See application file for complete search history.

(56) References Cited

U.S. PATENT DOCUMENTS

| | | | | | |
|---|---|---|---|---|---|
| 4,034,093 A | * | 7/1977 | Klemm | .................. | A01N 37/52 514/211.15 |
| 4,239,762 A | * | 12/1980 | Kramer | ................. | A01N 43/54 514/270 |
| 4,602,912 A | * | 7/1986 | de Sousa | ............... | A01N 53/00 427/427.7 |
| 4,634,707 A | * | 1/1987 | Brewer | .............. | C07D 239/557 514/270 |
| 4,636,508 A | * | 1/1987 | Brewer | .............. | C07D 239/545 514/269 |
| 4,762,830 A | * | 8/1988 | Sturm | .................. | C07D 233/70 514/270 |
| 4,879,276 A | * | 11/1989 | Brewer | .............. | C07D 239/557 514/269 |
| 4,880,811 A | * | 11/1989 | Warrell, Jr. | .......... | A61K 31/515 514/270 |
| 6,335,332 B1 | | 1/2002 | Olivia | | |
| 7,119,201 B2 | | 10/2006 | Reiter | | |
| 9,428,466 B2 | * | 8/2016 | Warrell, Jr. | .......... | C07D 239/60 |
| 2009/0264401 A1 | | 10/2009 | Gill et al. | | |

FOREIGN PATENT DOCUMENTS

| | | | | |
|---|---|---|---|---|
| WO | 88/10114 A1 | 12/1988 | | |
| WO | WO-8810114 A1 | * 12/1988 | ........... | A61K 31/515 |
| WO | 91/13623 A1 | 9/1991 | | |
| WO | WO-9113623 A1 | * 9/1991 | ........... | A61K 31/515 |
| WO | 2015/073317 A1 | 5/2015 | | |
| WO | 2015/123003 A1 | 8/2015 | | |
| WO | 2016/118611 A1 | 7/2016 | | |

OTHER PUBLICATIONS

CAS Abstract U.S. Pat. No. 4,634,707 (1987).*
CAS Registry No. 1349276-03-4 (2011).*
PCT Preliminary Report on Patentability in PCT/US2015/012370 dated Aug. 25, 2016, 7 pages.
PCT International Search Report and Written Opinion in PCT/US2015/012370 dated Apr. 17, 2015, 8 pages.
International Preliminary Report on Patentability in PCT/US2016/014107, dated Aug. 3, 2017, 7 pages.
International Search Report and Written Opinion in Intl. Appl. No. PCT/US2017/038525, dated Aug. 22, 2017, 16 pgs.
International Search Report and Written Opinion in PCT/US2016/014107, dated May 17, 2016, 11 pages.
Partial Search Report in PCT Application No. PCT/US2017/038522, dated Aug. 15, 2017, 2 pgs.
Search Opinion in EP Application No. 15 748 739.8, dated Sep. 1, 2017, 5 pgs.
Provisional Opinion Accompanying the Partial Search Result in EP 15 748 739.8, dated May 22, 2017, 5 pages.
Supplementary Partial European Search Report in EP 15 74 8739, dated May 22, 2017, 4 pages.
Lebedyeva, et al., "Reaction of barbituric acid with organic azides and phosphonium ylides", Central European Journal of Chemistry, vol. 11, No. 6, 2013, pp. 1019-1022.
International Search Report and Written Opinion in PCT/US2017/040836, dated Sep. 12, 2017, 15 pages.
International Search Report and Written Opinion in PCT/US2017/038522, dated Oct. 3, 2017, 20 pages.

* cited by examiner

*Primary Examiner* — Alexander R Pagano
(74) *Attorney, Agent, or Firm* — Servilla Whitney LLC

(57) ABSTRACT

Bifunctional compounds that increase uric acid excretion and reduce uric acid production. Methods of using these compounds for reducing uric acid levels in blood or serum, for treating disorders or uric acid metabolism, and for maintaining normal uric acid levels in blood or serum are provided. Pharmaceutical compositions comprising the bifunctional compounds are also provided.

15 Claims, 29 Drawing Sheets

Scheme 4

BIFUNCTIONAL COMPOUNDS AND USE FOR REDUCING URIC ACID LEVELS

CROSS REFERENCE TO RELATED APPLICATIONS

This is a National Phase entry of International Application No. PCT/US2015/012370, filed Jan. 22, 2015, which claims priority to U.S. Provisional Application 61/939,818, filed Feb. 14, 2014, the disclosures of which are incorporated herein by reference in their entireties.

TECHNICAL FIELD

This invention relates to compounds, pharmaceutical compositions and methods for reducing uric acid in blood or serum of a subject employing bifunctional compounds as active agents.

BACKGROUND

Gout afflicts more than 8 million U.S. subjects, and is associated with chronic elevation of uric acid (UA) in blood. The incidence of this condition has doubled in the past ten years. When UA exceeds solubility limits, it forms crystals that settle into joints and kidney, causing severe pain, destructive arthritis, and kidney failure. Treatment for chronic gout entails extended—if not lifelong—therapy focused on reducing UA production or increasing its excretion. The standard-of-care for initial therapy is allopurinol, a drug that inhibits xanthine oxidase (XO), a key production enzyme. Launched in 2009, Uloric® (febuxostat; Takeda), has similar activity as an XO inhibitor with somewhat higher efficacy and improved safety. Xanthine oxidase inhibitors are used as initial therapy in more than 90% of gout patients, but the therapeutic target is achieved in less than one-third of patients, the drugs have multiple side effects, and hypersensitivity (especially to allopurinol) is common. Given that most patients do not actually respond, the continued use of ineffective treatment administered over many months in order to determine the low percentage of patients who might respond represents an important burden to patients as well as substantial costs to global healthcare systems. Moreover, the high proportion of failures causes many patients to become non-compliant with therapy and thus at increased risk for development of chronic complications of gout, especially destructive arthritis and renal insufficiency.

Since 2000, rapid advances in the biology of proteins known as transporters have presented an array of new drug targets. The enzyme URAT1 is a high capacity renal transporter that reabsorbs most of the UA that is initially filtered into the urine from the blood by the kidney. Inhibitors of certain urate transporters may prevent such reabsorption and thereby increase UA excretion. Several drugs are now known to inhibit URAT1, including benzbromarone (approved but withdrawn in the U.S. by Sanofi in 2003), probenecid, and lesinurad (AstraZeneca), an investigational drug currently in late-stage development.

These drugs are all mono-functional. That is, they inhibit only one of the two equilibrium paths that reduce the levels of UA in blood (i.e., decreased production or increased excretion). Allopurinol is an example of a drug that decreases UA production by inhibiting xanthine oxidase, but it has no effect on renal excretion. As expected, allopurinol does not affect the activity of URAT1 or other renal urate transporters. Benzbromarone, lesinurad and probenecid increase UA excretion (i.e., they promote uricosuria) primarily via inhibition of URAT1, but these agents have no effect on UA production, since they have no substantial effect on xanthine oxidase. Since xanthine oxidase inhibition is the principal, preferred, and primary form of treatment for hyperuricemia, agents that promote uricosuria are typically used second-line and are commonly employed only in combination with xanthine oxidase inhibitors rather than as single-agents.

Non-sedating 5-carboxanilide derivatives of barbiturates, including merbarone (5-(N-phenylcarboxamido)-2-thio-barbituric acid), have been evaluated as potential cytotoxic anticancer drugs. Subsequently, it was discovered that clinical treatment with merbarone was associated with a marked reduction of UA levels in blood. Despite these discoveries, the cytotoxic activity of merbarone would completely preclude its use as a treatment for chronic lifelong disorders of UA metabolism, since the safety of such use (primarily its genotoxic potential) would pose a serious risk to other aspects of human health. Such clinical utility would only be possible if the genotoxic activity could be chemically dissociated from the various hypouricemic activities. The inventors have since described a number of non-genotoxic hypouricemic derivatives of merbarone.

There exists a compelling need for new drugs than can reduce UA levels in blood and provide better treatment for patients afflicted by gout. Reduction in UA is universally acknowledged as beneficial for patients with gout and other hyperuricemic disorders, and reduced serum UA is accepted by international drug regulatory agencies (e.g., the U.S. Food and Drug Administration (FDA), the European Medicines Agency (EMA), etc.) as an endpoint for commercial drug approval in these diseases. As previously noted, drugs that can overcome the limited clinical activity of xanthine oxidase inhibitors are available or are currently being investigated, but only as "add-ons" for combination use. The present invention relates to new compounds that can provide alternatives to current therapy for elevated UA levels and treatment of disorders of UA metabolism such as gout. Certain of these compounds have the particular advantage of bifunctional activity (i.e., decreasing UA production by inhibiting xanthine oxidase and increasing UA excretion by inhibiting a renal urate transporter), making them suitable for use as initial therapy and as single agents rather than "add-on" therapies. In addition, certain of these compounds have reduced toxicity compared to prior art drugs such as merbarone.

SUMMARY

In a first aspect, the invention relates to a compound having a structure represented by Formula (I):

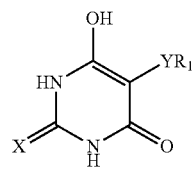

Formula (I)

wherein
  X is O or S;
  Y is present or absent, and if present is an alkyl group, or a heteroatomic group having from two to six atoms, wherein each atom is independently selected from the group consisting of carbon, oxygen, sulfur and nitrogen; and wherein each atom is optionally substituted with oxygen, sulfur or $C_1$-$C_6$ alkyl;

$R_1$ is substituted or unsubstituted phenyl, substituted or unsubstituted pyrimidyl; substituted or unsubstituted pyridyl; substituted or unsubstituted naphthyl; substituted or unsubstituted purinyl; substituted or unsubstituted thiazole; substituted or unsubstituted oxazole or isoxazole; substituted or unsubstituted cycloalkyl; substituted or unsubstituted piperidinyl; substituted or unsubstituted benzimidazole or imidazole; substituted or unsubstituted indazole; or substituted or unsubstituted benzoxazole or benzisoxazole;

provided that when $R_1$ is unsubstituted phenyl or 4'-hydroxyphenyl, Y is not —CONH—.

In one embodiment, the compound having a structure represented by Formula (I) is a compound wherein $R_1$ is phenyl substituted with at least one of W and Z, and X is O or S. In a modification of this embodiment, W and Z are independently halo, —$CF_3$, —$OR^2$, —$C(O)R^2$, $SR^2$, —$S(O)_e R^3$ where e is 1 or 2, —$N(R^2)_2$, —$NO_2$, —$CO_2 R^2$, —$OCO_2 R^3$, $OC(O)R^2$, —$CON(R^2)_2$, —$NR^2 C(O)R^2$, —CN, alkyl, aryl, alkenyl or alkynyl, and Y is present and is —CONH—. $R^2$ independently represents H, alkyl or aryl and $R^3$ independently represents alkyl or aryl. These compounds have a structure represented by Formula (II):

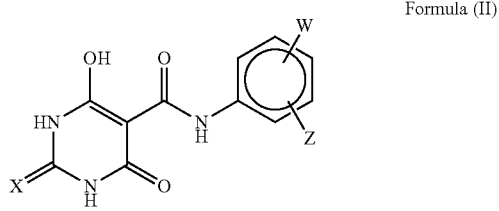

Formula (II)

wherein
X is O or S;
W is present or absent, and if present is one or more hydroxyl moieties;
Z is present or absent, and if present is halo, —CN, —$CF_3$, —$OR^2$, —$C(O)R^2$, $SR^2$, —$S(O)_e R^3$ where e is 1 or 2, —$N(R^2)_2$, —$NO_2$, —$CO_2 R^2$, —$OCO_2 R^3$, $OC(O)R^2$, —$CON(R^2)_2$, —$NR^2 C(O)R^2$, —CN, alkyl, aryl, alkenyl or alkynyl;
each $R^2$ is independently H, alkyl or aryl; and
each $R^3$ is independently alkyl or aryl;
provided that at least one of W and Z is present; if W is present and Z is absent, W is not 4'-hydroxy, and; if Z is present and W is absent, Z is not —$OCH_3$ or —$OCOCH_3$. In certain embodiments, alkyl is C1-C6 alkyl. In other embodiments, aryl is C6-C10 aryl. In other embodiments alkenyl is C2-C6 alkenyl. In other embodiments alkynyl is C2-C6 alkynyl.

In a specific embodiment, the compound having a structure represented by Formula (II) is a compound wherein W is hydroxyl and Z is one or more halogen atoms. In a further specific embodiment, W is hydroxyl and Z is one or more fluorine atoms. In another specific embodiment, Z is —NHC(O)$CH_3$. In another specific embodiment, Z is —$S(O)_2 CH_3$. In another specific embodiment, Z is —CN. In another specific embodiment, W is OH and Z is —CN. In another specific embodiment, Z is —$CO_2 H$.

In another embodiment, the compound having a structure represented by Formula (I) is a compound wherein $R^1$ is heteroaryl optionally substituted with W and/or Z, X is O or S; W if present is one or more hydroxyl moieties; and Z if present is one or more halogen atoms, —CN, —$CF_3$, —$OR^2$, —$C(O)R^2$, $SR^2$, —$S(O)_e R^3$ where e is 1 or 2, —$N(R^2)_2$, —$NO_2$, —$CO_2 R^2$, —$OCO_2 R^3$, $OC(O)R^2$, —$CON(R^2)_2$, —$NR^2 C(O)R^2$, —CN, alkyl, aryl, alkenyl or alkynyl, and at least one of a, b, c, d, and e is nitrogen; $R^2$ is H, alkyl or aryl, and; $R^3$ is alkyl or aryl:

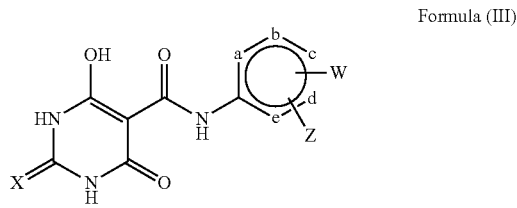

Formula (III)

wherein $R^2$ and $R^3$ are as defined above.

In a specific embodiment, the compound having a structure represented by Formula (III) is the compound wherein $R^1$ of Formula (I) is pyridazine, i.e., two adjacent residues of a-e are nitrogen. A specific example of a pyridazine derivative of Formula (III) is the compound wherein W and Z are absent, and any two adjacent residues of a, b, c, d, and e are nitrogen, such as the compound wherein both c and d are nitrogen, and a, b, and e are carbon. In another specific embodiment, the compound having a structure represented by Formula (III) is a compound wherein Z is —CN; for example, $R^1$ may be —CN substituted pyridyl.

In a second aspect, the invention relates to a compound having a structure represented by Formula (IV):

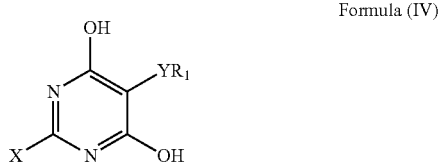

Formula (IV)

wherein
X is H or cyanoamino;
Y is present or absent, and if present is an alkyl group, or a heteroatomic group having from two to twenty atoms, wherein each atom is independently selected from the group consisting of carbon, oxygen, sulfur and nitrogen; and
$R_1$ is substituted or unsubstituted phenyl, substituted or unsubstituted pyrimidyl; substituted or unsubstituted pyridyl; substituted or unsubstituted naphthyl; substituted or unsubstituted purinyl; substituted or unsubstituted thiazole; substituted or unsubstituted oxazole or isoxazole; substituted or unsubstituted cycloalkyl; substituted or unsubstituted benzimidazole or imidazole; substituted or unsubstituted indazole; or substituted or unsubstituted benzoxazole or benzisoxazole In one embodiment, the compound having a structure represented by Formula (IV) is a compound wherein $R_1$ is unsubstituted phenyl. In a modification of this embodiment, X is —NH—CN (cyanoamino). In an alternative modification of this embodiment, X is H. In a further modification of any of these embodiments, Y is present and is —CONH—.

A third aspect of the invention relates to methods for reducing uric acid levels in blood or serum of a subject comprising administering a compound having a structure represented by Formula (I), Formula (II), Formula (III), Formula (IV), or a combination thereof, to a subject in need thereof in an amount effective to reduce blood or serum uric acid levels. It is to be understood that such methods for reducing uric acid levels correspond to a compound having a structure represented by Formula (I), Formula (II), Formula (III), Formula (IV), or a combination thereof, for use in medicine as well as a compound having a structure represented by Formula (I), Formula (II), Formula (III), Formula (IV), or a combination thereof, for use in the treatment of elevated uric acid levels. In a specific embodiment, the methods for reducing uric acid levels in blood or serum of a subject comprise administering to a subject in need thereof one or more compounds having a structure represented by Formula (I) or Formula (II), wherein $R_1$ is phenyl substituted with W and Z, W is hydroxyl, Z is one or more halogen atoms, and X is O or S. In a modification of this embodiment, the methods comprise administering one or more compounds having a structure represented by Formula (I) or Formula (II), wherein $R_1$ is phenyl substituted with W and Z, W is hydroxyl, Z is one or more fluorine atoms, X is O or S, and Y is —CONH—, to a subject in need thereof in an amount effective to reduce blood or serum uric acid levels.

A modification of this aspect of the invention relates to methods for preventing elevation of uric acid levels in blood or serum of a subject comprising administering a compound having a structure represented by Formula (I), Formula (II), Formula (III), Formula (IV), or a combination thereof, to a subject in need thereof in an amount effective to prevent elevation of blood or serum uric acid levels. It is to be understood that such methods for preventing elevation of uric acid levels correspond to a compound having a structure represented by Formula (I), Formula (II), Formula (III), Formula (IV), or a combination thereof, for use in medicine as well as a compound having a structure represented by Formula (I), Formula (II), Formula (III), Formula (IV), or a combination thereof, for use in the prevention of elevated uric acid levels. In a specific embodiment of this aspect, the methods for preventing elevation of uric acid levels in blood or serum of a subject comprise administering to a subject in need thereof one or more compounds having a structure represented by Formula (I) or Formula (II), wherein $R_1$ is phenyl substituted with W and Z, W is hydroxyl, Z is one or more halogen atoms and X is O or S. In a modification of this embodiment, the methods comprise administering one or more compounds having a structure represented by Formula (I) or Formula (II), wherein $R_1$ is phenyl substituted with W and Z, W is hydroxyl, Z is one or more fluorine atoms, X is O or S, and Y is —CONH—, to a subject in need thereof in an amount effective to prevent elevation of blood or serum uric acid levels.

In certain embodiments of these methods, a compound having a structure represented by Formula (I), Formula (II), Formula (III), Formula (IV), or a combination thereof, is administered to a subject with gout, hyperuricemia, kidney disease, arthritis, kidney stones, kidney failure, urolithiasis, plumbism, hyperparathyroidism, psoriasis, inborn genetic errors of metabolism, sarcoidosis or cardiovascular disease to reduce uric acid levels. In specific embodiments, the drug(s) are administered to a subject with gout or hyperuricemia to reduce uric acid levels. It is to be understood that such methods of treatment correspond to a compound having a structure represented by Formula (I), Formula (II), Formula (III), Formula (IV), or a combination thereof, for use in medicine as well as a compound having a structure represented by Formula (I), Formula (II), Formula (III), Formula (IV), or a combination thereof, for use in the treatment of gout, hyperuricemia, kidney disease, arthritis, kidney stones, kidney failure, urolithiasis, plumbism, hyperparathyroidism, psoriasis, inborn genetic errors of metabolism, sarcoidosis or cardiovascular disease to reduce uric acid levels. In other embodiments, one or more compounds having a structure represented by Formula (I) or Formula (II), wherein $R_1$ is phenyl substituted with W and Z, W is hydroxyl, Z is one or more halogen atoms, X is O or S, and Y is —CONH— is/are administered to a subject with gout, hyperuricemia, kidney disease, arthritis, kidney stones, kidney failure, urolithiasis, plumbism, hyperparathyroidism, psoriasis, inborn genetic errors of metabolism, sarcoidosis or cardiovascular disease to reduce uric acid levels. In further specific embodiments, the methods comprise administering one or more compounds having a structure represented by Formula (I) or Formula (II), wherein $R_1$ is phenyl substituted with W and Z, W is hydroxyl, Z is one or more fluorine atoms, X is O or S, and Y is —CONH— to reduce uric acid levels.

In certain embodiments of any of the foregoing methods, a compound having a structure represented by Formula (I), Formula (II), Formula (III), Formula (IV), or a combination thereof, is administered by injection, infusion, intranasal, intrarectal, or oral administration. In other embodiments, a compound having a structure represented by Formula (I), Formula (II), Formula (III), Formula (IV), or a combination thereof, is administered by injection, infusion, or oral administration.

In certain embodiments of any of the foregoing methods, a compound having a structure represented by Formula (I), Formula (II), Formula (III), Formula (IV), or a combination thereof, is administered in a formulation that enables controlled release, i.e., a formulation that releases the active ingredient more slowly or prolongs the duration of its action within the body. In specific embodiments, the controlled release formulation is an oral controlled release formulation. In other embodiments of any of the foregoing methods, one or more compounds having a structure represented by Formula (I) or Formula (II), wherein $R_1$ is phenyl substituted with W and Z, W is hydroxyl, Z is one or more fluorine atoms, X is O or S, and Y is —CONH— is/are administered in a formulation that enables controlled release.

In certain embodiments of any of the foregoing methods, blood or serum uric acid levels are reduced by at least about 25% compared to blood or serum uric acid levels prior to administration of a compound having a structure represented by Formula (I), Formula (II), Formula (III), Formula (IV), or a combination thereof. In specific embodiments, blood or serum uric acid levels of the subject are reduced by at least about 50% compared to levels prior to administration. In a specific embodiment, uric acid levels are reduced by about 75% even at daily doses of 1,500 mg/m²/day or less.

In certain embodiments of any of the foregoing methods, a compound having a structure represented by Formula (I), Formula (II), Formula (III), Formula (IV), or a combination thereof, is administered to the subject up to four times per day, once daily, once, twice or three times per week or once monthly. In other embodiments of any of the foregoing methods, one or more compounds having a structure represented by Formula (I) or Formula (II), wherein $R_1$ is phenyl substituted with W and Z, W is hydroxyl, Z is one or more halogen atoms and X is O or S, is/are administered to the subject up to four times per day, once daily, once, twice or three times per week or once monthly. In further embodiments of any of the foregoing methods, one or more compounds having a structure represented by Formula (I) or Formula (II), wherein $R_1$ is phenyl substituted with W and Z, W is hydroxyl, Z is one or more fluorine atoms, X is O or S, and Y is —CONH— is/are administered to the subject up to four times per day, once daily, once, twice or three times per week or once monthly.

A fourth aspect of the invention relates to methods for treating a disorder of uric acid metabolism associated with or caused by elevated uric acid in blood or serum comprising administering to a subject in need thereof a compound having a structure represented by Formula (I), Formula (II), Formula (III), Formula (IV), or a combination thereof, in an amount effective to reduce blood or serum uric acid levels or prevent elevation of blood or serum uric acid levels, thereby treating the disorder of uric acid metabolism. One such embodiment relates to methods for treating a disorder of uric acid metabolism associated with or caused by elevated uric acid in blood or serum comprising administering to a subject in need thereof one or more compounds having a structure represented by Formula (I) or Formula (II), wherein $R_1$ is phenyl substituted with W and Z, W is hydroxyl, Z is one or more halogen atoms and X is O or S, in an amount effective to reduce blood or serum uric acid levels, thereby treating the disorder of uric acid metabolism. A second such embodiment relates to methods for treating a disorder of uric acid metabolism associated with or caused by elevation of uric acid in blood or serum comprising administering to a subject in need thereof one or more compounds having a structure represented by Formula (I) or Formula (II), wherein $R_1$ is phenyl substituted with W and Z, W is hydroxyl, Z is one or more fluorine atoms and X is O or S, in an amount effective to prevent elevation of blood or serum uric acid levels, thereby treating the disorder of uric acid metabolism. In either embodiment, Y may be present in one or more of the compounds having a structure represented by Formula (I), and Y may be —CONH—, as shown in Formula (II). Specific embodiments of these methods for treating a disorder of uric acid metabolism are as described above for reducing uric acid levels in blood or serum.

A further aspect of the invention provides pharmaceutical compositions comprising a compound having a structure represented by Formula (I), Formula (II), Formula (III), Formula (IV), or a combination thereof, and a pharmaceutically acceptable carrier. In a specific embodiment, the pharmaceutical composition comprises a compound having a structure represented by Formula (I) or Formula (II), wherein $R_1$ is phenyl substituted with W and Z, W is hydroxyl, Z is one or more halogen atoms and X is O or S. In a further specific embodiment, the pharmaceutical composition comprises a compound having a structure represented by Formula (I) or Formula (II), wherein $R_1$ is phenyl substituted with W and Z, W is hydroxyl, Z is one or more fluorine atoms, X is O or S, and Y is present and is —CONH—.

In certain embodiments of the pharmaceutical composition, the pharmaceutically acceptable carrier is selected from the group consisting of one or more of a solvent, a dispersing agent, a coating, a surfactant, a preservative, an alcohol, a polyol, and an isotonic agent.

In certain embodiments of any of the foregoing pharmaceutical compositions, the composition is formulated for administration by injection, infusion or oral routes.

In certain embodiments of any of the foregoing pharmaceutical compositions, the composition is formulated as a solution, emulsion, capsule, or tablet.

In certain embodiments of any of the foregoing pharmaceutical compositions, the composition is formulated for controlled release of the compound having a structure represented by Formula (I), Formula (II), Formula (III), Formula (IV), or a combination thereof, to provide slower release of the active ingredient or to prolong the duration of its action within the body.

A further aspect of the invention relates to methods for synthesizing the compounds discussed above, as discussed in more detail below.

DETAILED DESCRIPTION

Figure 1:
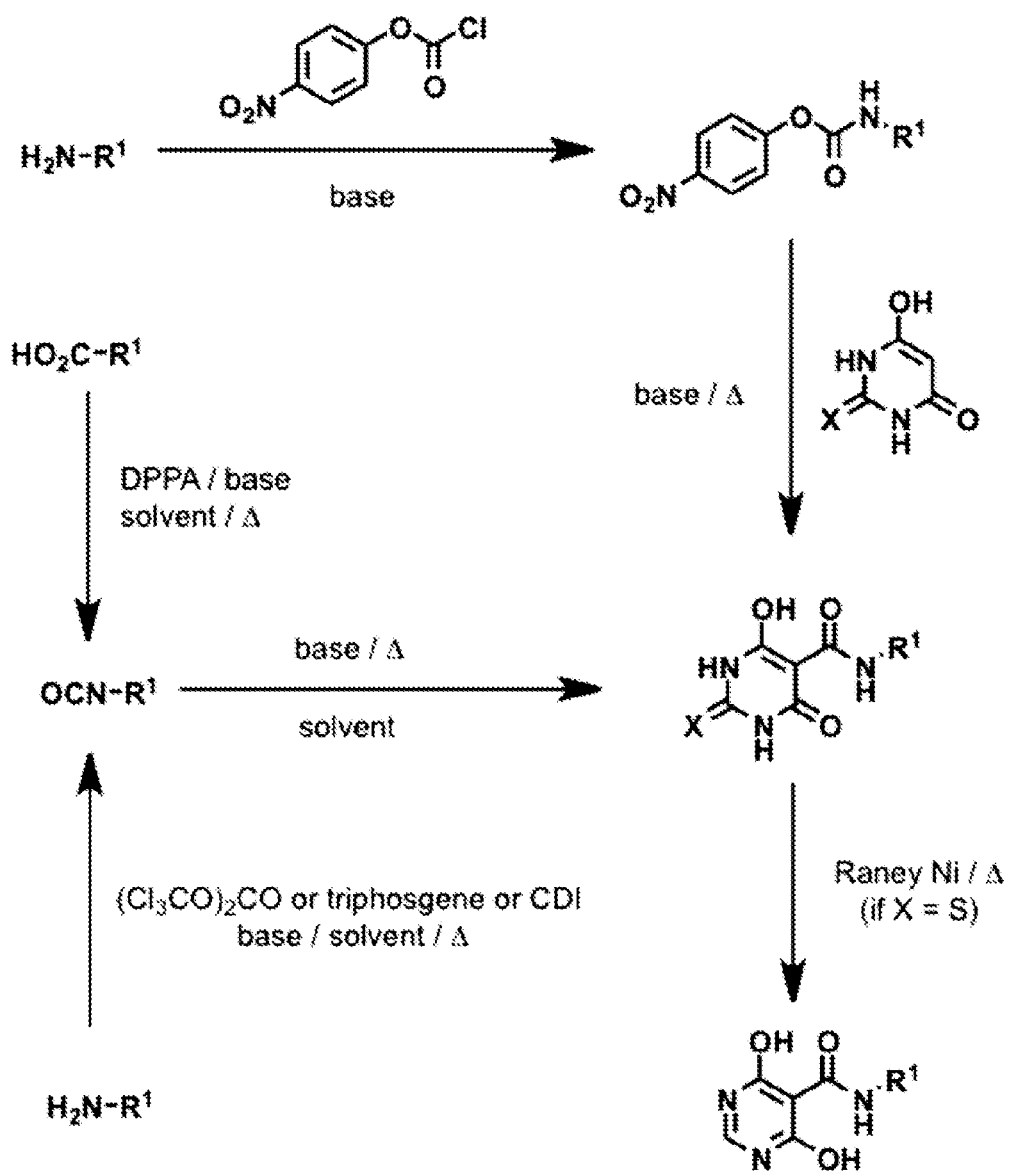
FIG. 1 illustrates a general scheme for synthesis of compounds having a structure represented by Formula (I), wherein Y is —CONH—.

Before describing several exemplary embodiments of the invention, it is to be understood that the invention is not limited to the details of construction or process steps set forth in the following description. The invention is capable of other embodiments and of being practiced or being carried out in various ways.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

As used herein, the term "bifunctional" with respect to disclosed compounds means that the compound inhibits both a renal transporter, including but not limited to URAT1, and xanthine oxidase. The potency of inhibition of either target may vary, but in general an IC50 of less than about 100 μM for both xanthine oxidase and a renal transporter such as URAT1 is considered bifunctional. An IC50 of less than about 50 μM for both xanthine oxidase and URAT1 is considered a particularly active bifunctional compound, and an IC50 of less than 10 μM is considered a highly potent bifunctional compound.

As used herein, the term "monofunctional" with respect to disclosed compounds means that the compound inhibits an enzyme in the uric acid metabolic pathway involved in uric acid excretion that is either a renal transporter, including but not limited to URAT1, or an enzyme involved in uric acid production, including but not limited to xanthine oxidase, but does not inhibit both enzyme types. The potency of inhibition of single target may vary, but in general an IC50 of greater than about 100 μM for one of xanthine oxidase or URAT1, and an IC50 of less than about 100 μM for the other of xanthine oxidase or URAT1, is considered monofunctional. An IC50 of less than about 50 μM for one of xanthine oxidase or URAT1, and an IC50 of greater than about 100 μM for the other of xanthine oxidase or URAT1, is considered a particularly active monofunctional compound. An IC50 of less than about 10 μM for one of xanthine oxidase or URAT1, and an IC50 of greater than about 100 μM for the other of xanthine oxidase or URAT1, is considered a highly potent monofunctional compound.

As used herein, the term "treatment" refers to reducing elevated uric acid levels in blood or serum, preferably by reducing levels to the normal, low-normal or sub-normal range, with an overall goal of relieving symptoms and/or preventing recurrences of active disease. For example, a typical "therapeutic target" for treatment of elevated serum uric acid is a level ≤6.0 mg/dL. "Elevated" uric acid levels generally refers to high-normal and above-normal uric acid levels, as long-term elevated levels can result in conditions that require additional treatment.

As used herein, the term "preventing" elevation of uric acid levels in blood or serum refers to maintaining normal or therapeutically acceptable uric acid levels in blood or serum in a subject who would otherwise experience an increase in uric acid levels, with an overall goal of preventing development or recurrence of symptoms and/or preventing recurrences of active disease. It will be appreciated that prevention of elevation of uric acid levels is a goal of the maintenance therapy discussed below.

The numbering of the positions on the barbiturate ring used herein follows the convention of Warrell (U.S. Pat. No. 4,880,811). It is also to be understood that although the compounds disclosed herein are generally illustrated by specific chemical structures, the disclosure of the compounds is intended to include their tautomers The compounds described herein meet certain needs in the therapeutic field of reduction of uric acid levels in blood and treatment of disorders of uric acid metabolism that are associated with, or caused by, elevated uric acid levels in blood or serum. Certain of the compounds are potent monofunctional inhibitors of URAT1 or xanthine oxidase. Certain of the compounds are bifunctional inhibitors of both URAT1 and xanthine oxidase. Certain of the compounds have the additional advantage of being substantially non-genotoxic.

The improved biological activity profile of the compounds of the invention and their potency make these compounds useful new drugs for reducing uric acid levels in blood, and for treating disorders of uric acid metabolism that are associated with, or caused by, elevated uric acid levels in blood or serum, including gout. Of particular significance is the advantage that the bifunctional compounds can be used effectively as monotherapy for reducing uric acid levels in blood, for treating disorders of uric acid metabolism, and specifically for treating gout.

In a first aspect, the invention relates to a compound having a structure represented by Formula (I):

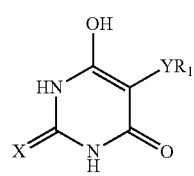

Formula (I)

wherein
X is O or S;
Y is present or absent, and if present is an alkyl group, or a heteroatomic group having from two to six atoms, wherein each atom is independently selected from the group consisting of carbon, oxygen, sulfur and nitrogen; and wherein each atom is optionally substituted with oxygen, sulfur or $C_1$-$C_6$ alkyl;
$R_1$ is substituted or unsubstituted phenyl, substituted or unsubstituted pyrimidyl; substituted or unsubstituted pyridyl; substituted or unsubstituted naphthyl; substituted or unsubstituted purinyl; substituted or unsubstituted thiazole; substituted or unsubstituted oxazole or isoxazole; substituted or unsubstituted cycloalkyl; substituted or unsubstituted piperidinyl; substituted or unsubstituted benzimidazole or imidazole; substituted or unsubstituted indazole; or substituted or unsubstituted benzoxazole or benzisoxazole;
provided that when $R_1$ is unsubstituted phenyl or 4'-hydroxyphenyl, Y is not —CONH—.

Specific embodiments of the compounds having structures represented by Formula (I) include the following compounds:

1. The compound wherein X is S, Y is present and is —CONH—, and $R_1$ is halo-substituted cycloalkyl, for example the compound having a structure represented by Formula ($I_a$):

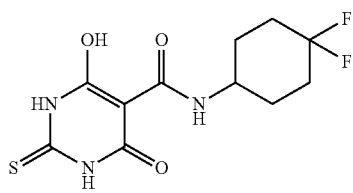

Formula ($I_a$)

N-(4',4'-difluorocyclohex-1-yl)-1,2,3,4-tetrahydro-6-hydroxy-4-oxo-2-thioxo-5-pyrimidinecarboxamide or N-(4,4-difluorocyclohexyl)-6-hydroxy-4-oxo-2-thioxo-1,2,3,4-tetrahydropyrimidine-5-carboxamide or 5-(N-(4',4'-difluorocyclohex-1-yl)carbamoyl)-2-thioxobarbituric acid.

2. The compound wherein X is S, Y is present and is —CONH—, and $R_1$ is halo-substituted phenyl, for example the compound having a structure represented by Formula ($I_b$):

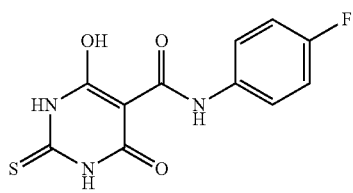

Formula ($I_b$)

N-(4'-fluorophenyl)-1,2,3,4-tetrahydro-6-hydroxy-4-oxo-2-thioxo-5-pyrimidinecarboxamide or 5-(N-(4'-fluorophenyl)carbamoyl)-2-thioxobarbituric acid.

3. The compound wherein X is S, Y is present and is —CONH—, and $R_1$ is halo- and hydroxy-substituted phenyl, for example the compound having a structure represented by Formula ($I_c$):

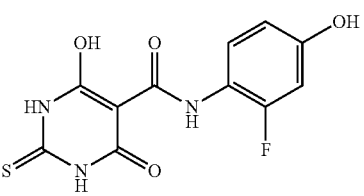

Formula ($I_c$)

N-(2'-fluoro-4'-hydroxyphenyl)-1,2,3,4-tetrahydro-6-hydroxy-4-oxo-2-thioxo-5-pyrimidinecarboxamide or N-(2-fluoro-4-hydroxyphenyl)-6-hydroxy-2,4-dioxo-1,2,3,4-tetrahydropyrimidine-5-carboxamide or N-(4-fluorophenyl)-6-hydroxy-4-oxo-2-thioxo-1,2,3,4-tetrahydropyrimidine-5-carboxamide or 5-(N-(2'-fluoro-4'-hydroxyphenyl))carbamoyl-2-thioxobarbituric acid.

4. The compound wherein X is S, Y is present and is —CONH—, and $R_1$ is thiazole, for example the compound having a structure represented by Formula ($I_d$):

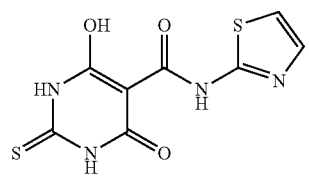

Formula ($I_d$)

1,2,3,4-tetrahydro-6-hydroxy-4-oxo-N-(thiazol-2'-yl)-2-thioxo-5-pyrimidinecarboxamide or 6-hydroxy-4-oxo-N-(thiazol-2-yl)-2-thioxo-1,2,3,4-tetrahydropyrimidine-5-carboxamide or 5-(N-(thiazol-2'-yl)carbamoyl)-2-thioxobarbituric acid.

5. The compound wherein X is S, Y is present and is —CONH—, and $R_1$ is oxazole, for example the compound having a structure represented by Formula ($I_e$):

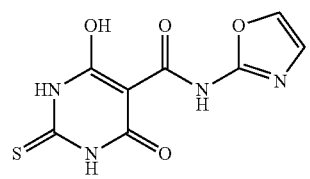

Formula ($I_e$)

1,2,3,4-tetrahydro-6-hydroxy-N-(oxazol-2'-yl)-4-oxo-2-thioxo-5-pyrimidinecarboxamide or 6-hydroxy-N-(oxazol-2-yl)-4-oxo-2-thioxo-1,2,3,4-tetrahydropyrimidine-5-carboxamide or 5-(N-(oxazol-2-yl)carbamoyl)-2-thioxobarbituric acid.

6. The compound wherein X is O, Y is present and is —CONH—, and $R_1$ is substituted pyrimidyl, for example the compound having a structure represented by Formula ($I_f$):

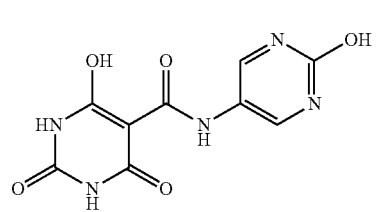

Formula ($I_f$)

1,2,3,4-tetrahydro-6-hydroxy-N-(2'-hydroxypyrimidin-5'-yl)-2,4-dioxo-5-pyrimidinecarboxamide or 6-hydroxy-N-(2-hydroxypyrimidin-5-yl)-2,4-dioxo-1,2,3,4-tetrahydropyrimidine-5-carboxamide or 5-(N-(2'-hydroxypyrimidin-5'-yl))carbamoylbarbituric acid.

7. The compound wherein X is O, Y is present and is —CONH—, and $R_1$ is substituted phenyl, for example wherein $R_1$ is halo- and hydroxy-substituted phenyl, such as fluoro- and hydroxy-substituted phenyl, including the compound having a structure represented by Formula ($I_g$):

Formula (I_g)

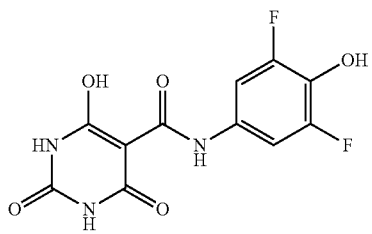

N-(3',5'-difluoro-4'-hydroxyphenyl)-1,2,3,4-tetrahydro-6-hydroxy-2,4-dioxo-5-pyrimidinecarboxamide or N-(3,5-difluoro-4-hydroxyphenyl)-6-hydroxy-2,4-dioxo-1,2,3,4-tetrahydropyrimidine-5-carboxamide or 5-(N-(3',5'-difluoro-4'-hydroxyphenyl))carbamoylbarbituric acid; or 8. The compound having the structure represented by Formula (I_h):

Formula (I_h)

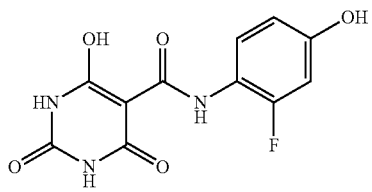

N-(2'-fluoro-4'-hydroxyphenyl)-1,2,3,4-tetrahydro-6-hydroxy-2,4-dioxo-5-pyrimidinecarboxamide or N-(2-fluoro-4-hydroxyphenyl)-6-hydroxy-2,4-dioxo-1,2,3,4-tetrahydropyrimidine-5-carboxamide or 5-(N-(2'-fluoro-4'-hydroxyphenyl))carbamoylbarbituric acid.

9. The compound wherein X is O, Y is present and is —NHCO—, and $R_1$ is substituted phenyl, for example wherein $R_1$ is halo-substituted phenyl, such as the compound having a structure represented by Formula (I_i):

Formula (I_i)

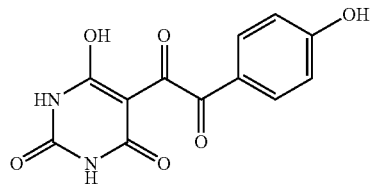

1,2,3,4-tetrahydro-6-hydroxy-5-(N-(4'-hydroxybenzoyl))amino-2,4-dioxopyrimidine or 5-(4-hydroxybenzamido)-2,6-dioxo-1,2,3,6-tetrahydropyrimidin-4-ol or 5-(N-(4'-hydroxybenzoyl))aminobarbituric acid.

10. The compound wherein X is O, Y is absent (i.e., $R_1$ is linked directly to the barbiturate core ring), and $R_1$ is benzoxazole, for example the compound having a structure represented by Formula (I_j):

Formula (I_j)

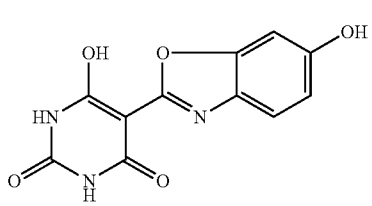

1,2,3,4-tetrahydro-6-hydroxy-5-(5'-hydroxy-1',3'-benzoxazol-2'-yl)-2,4-dioxopyrimidine or 5-(6-hydroxybenzo[d]oxazol-2-yl)pyrimidine-2,4,6(1H,3H,5H)-trione or 5-(5'-hydroxy-1',3'-benzoxazol-2'-yl)barbituric acid.

11. The compound wherein X is O, Y is present and is —CONH—, and $R_1$ is unsubstituted pyridyl, for example the compound having a structure represented by Formula (I_k):

Formula (I_k)

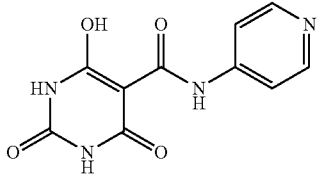

1,2,3,4-tetrahydro-6-hydroxy-2,4-dioxo-N-(pyridin-4'-yl)-5-pyrimidinecarboxamide or 6-hydroxy-2,4-dioxo-N-(pyridin-4-yl)-1,2,3,4-tetrahydropyrimidine-5-carboxamide or 5-(N-(pyridin-4'-yl))carbamoylbarbituric acid.

12. The compound wherein X is O, Y is present and is —CONH—, and $R_1$ is substituted pyridyl, for example the compound having a structure represented by Formula (I_l):

Formula (I_l)

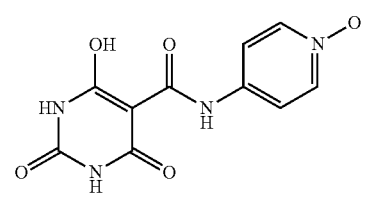

1,2,3,4-tetrahydro-6-hydroxy-2,4-dioxo-N-(1'-oxopyridin-4'-yl)-5-pyrimidinecarboxamide or 5-(N-(1'-oxopyridin-4'-yl))carbamoylbarbituric acid.

13. The compound wherein X is O, Y is present and is —CONH—, and $R_1$ is pyridone, for example the compound having a structure represented by Formula (I_m):

Formula (I_m)

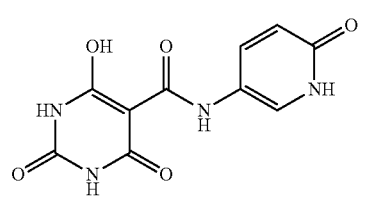

1,2,3,4-tetrahydro-N-(1',2'-dihydro-2'-oxopyridin-5'-yl)-6-hydroxy-4-oxo-5-pyrimidinecarboxamide or 5-(N-(1',2'-dihydro-2'-oxopyridin-5'-yl))carbamoylbarbituric acid.

or, the compound having a structure represented by Formula ($I_n$):

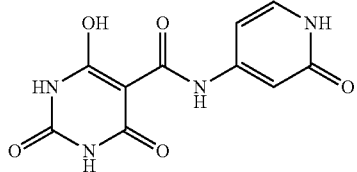

Formula ($I_n$)

1,2,3,4-tetrahydro-N-(1',2'-dihydro-2'-oxopyridin-4'-yl)-6-hydroxy-4-oxo-5-pyrimidinecarboxamide or 5-(N-(1',2'-dihydro-2'-oxopyridin-4'-yl))carbamoylbarbituric acid.

14. The compound wherein X is O, Y is present and is —CONH—, and $R_1$ is benzimidazole, for example the compound having a structure represented by Formula ($I_o$):

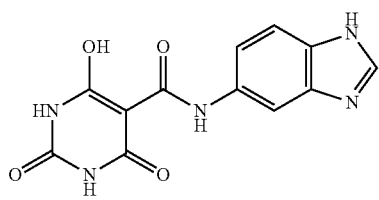

Formula ($I_o$)

N-(1'H-benzimidazol-5'-yl)-1,2,3,4-tetrahydro-6-hydroxy-2,4-dioxo-5-pyrimidinecarboxamide or N-(1H-benzo[d]imidazol-6-yl)-6-hydroxy-2,4-dioxo-1,2,3,4-tetrahydropyrimidine-5-carboxamide or 5-(N-(1'H-benzimidazol-5'-yl))carbamoylbarbituric acid.

15. The compound wherein X is O, Y is present and is —CONH—, and $R_1$ is hydroxy-substituted purinyl, for example the compound having a structure represented by Formula ($I_p$):

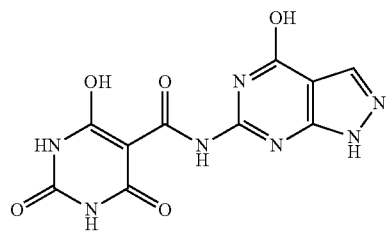

Formula ($I_p$)

N-(4-hydroxy-7H-pyrazolo[3,4-d]pyrimidin-2-yl)-6-hydroxy-2,4-dioxo-1,2,3,4-tetrahydropyrimidine-5-carboxamide or 6-hydroxy-5-[(4-hydroxy-1,2,5,7-tetraza-1H-inden-6-ylamino)carbonyl]-1,3-dihydropyrimidine-2,4-dione or 5-(N-(4'-hydroxy-7'H-pyrazolo[3',4'-d]pyrimidin-2'-yl))carbamoylbarbituric acid.

Compounds having structures represented by Formula (I), wherein Y is —CONH— may be synthesized as shown in FIG. 1. The appropriate activated side chain for the desired compound (—CONH—$R^1$) is coupled to either barbituric acid (X=O) or thiobarbituric acid (X=S) to directly generate compounds represented by Formula (I). Any known method for activating the side chain can be used. For example, the para-nitrophenylcarbamate of the corresponding amine ($H_2N$—$R^1$) may be generated by reaction of the amine ($H_2N$—$R^1$) with 4-nitrophenyl chloroformate in the presence of base. In a further example, the corresponding isocyanate (OCN—$R^1$) of the amine ($H_2N$—$R^1$) can be generated by standard methods, such as reaction of the corresponding amine ($H_2N$—$R^1$) with triphosgene or reaction of the corresponding carboxylic acid ($HO_2C$—$R^1$) with diphenyl phosphorazidate. The activated side chain may then be reacted with either barbituric acid (X=O) or thiobarbituric acid (X=S) using routine methods, such as in the presence of base. Compounds represented by Formula (IV) where X=H can be prepared from compounds of the formula (I) where X=S via various desulfurization methods, such as treatment with rainy nickel.

Figure 5:
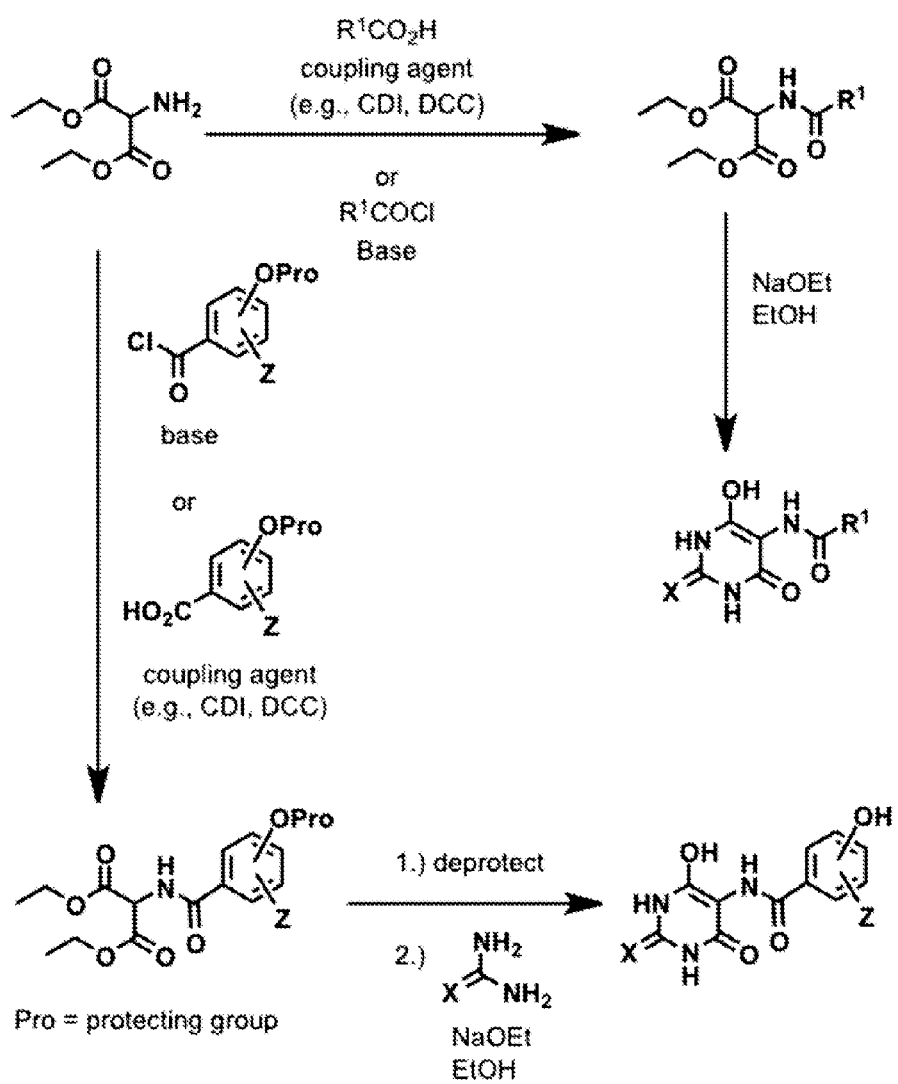
FIG. 5 illustrates a general scheme for synthesis of compounds having a structure represented by Formula (I), wherein Y is —NHCO—.

Compounds having structures represented by Formula (I), wherein Y is —NHCO— may be synthesized as shown in FIG. 5. This scheme depicts an alternative embodiment wherein $R_1$ is hydroxyl-substituted phenyl, but Y is —NHCO (i.e., reverse amide). It centers on the construction of the side chain first from a diester of 2-aminomalonate by coupling it with an appropriately substituted carboxylic acid ($R^1CO_2H$) using a standard coupling reagent like DCC or CDI. Alternatively, the corresponding acid chloride of the appropriately substituted carboxylic acid ($R^1COCl$) could be used in place of the carboxylic acid ($R^1CO_2H$). Once it is coupled, the resultant diester is condensed with either urea (X=O) or thiourea (X=S) under basic conditions to form the barbiturate (X=O) or thiobarbiturate ring (X=S), respectively. If present, the protecting groups on the side chain can be removed by standard deprotection conditions depending on the nature of the protecting group.

Figure 6:
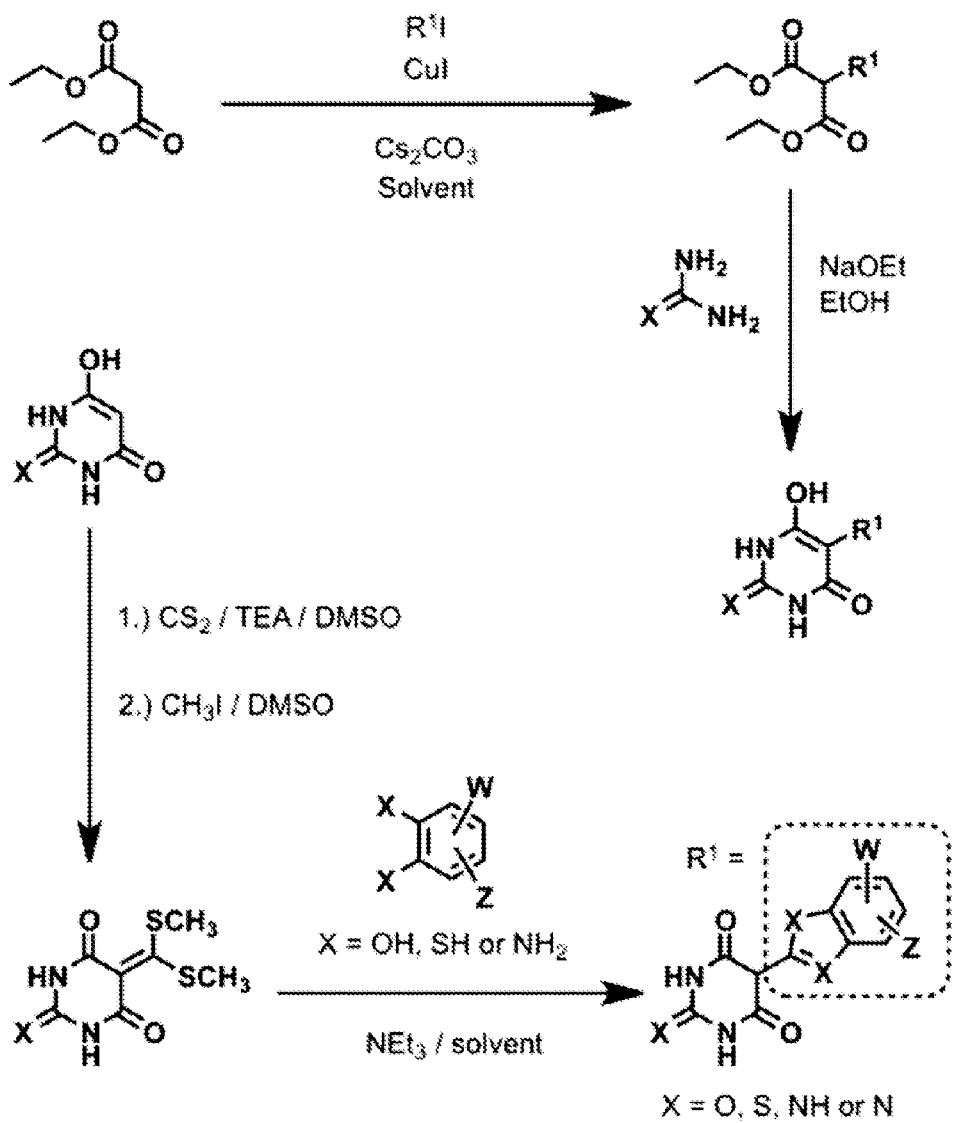
FIG. 6 illustrates a general scheme for synthesis of compounds having a structure represented by Formula (I), wherein Y is absent (i.e., $R_1$ is directly bonded to the barbiturate ring).

Compounds having structures wherein $R_1$ is linked directly to the barbiturate core ring (i.e., Y is absent) may be synthesized as shown in FIG. 6. Such compounds can be prepared by constructing the barbiturate (X=O) or thiobarbiturate ring (X=S) first, similar to the method described in FIG. 1, or by introducing the barbiturate (X=O) or thiobarbiturate ring (X=S) ring last, similar to the method described for FIG. 5. In the first case the appropriate side chain ($R^1$) is first appended to diethylmalonate. This can be accomplished by a variety of standard coupling conditions, including copper mediated coupling conditions or simple alkylation by reacting the anion of a diester of malonate with the appropriate alkyl halide ($R^1X$). The barbiturate (X=O) or thiobarbiturate ring (X=S) ring is then formed as described in FIG. 5. In the latter case the ketene thioacetal is formed first by the reaction of barbituric acid (X=O) or thiobarbituric acid (X=S) with carbon disulfide, followed by a quench with methyl iodide or similar alkylating agent. The thio groups in the resultant intermediate can then be displaced with an appropriate substituted reagent, which is usually a substituted phenyl ring containing two nucleophilic groups to displace the thio moieties. If present, the protecting groups on the side chain can be removed by standard deprotection conditions depending on the nature of the protecting group.

With reference to the foregoing specific embodiments of compounds having a structure represented by Formula I, it is to be understood that a further specific embodiment of the compounds of the invention comprises a compound having a structure represented by Formula (II):

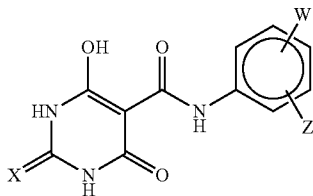

Formula (II)

wherein
X is O or S;
W is present or absent, and if present is one or more hydroxyl moieties;
Z is present or absent, and if present is halo, —CN, —CF$_3$, —OR$^2$—C(O)R$^2$, SR$^2$, —S(O)$_e$R$^3$ wherein e is 1 or 2, —N(R$^2$)$_2$, —NO$_2$, —CO$_2$R$^2$, —OCO$_2$R$^3$, OC(O)R$^2$, —CON(R$^2$)$_2$, —NR$^2$C(O)R$^2$, —CN, alkyl, aryl, alkenyl or alkynyl;
each R$^2$ is independently H, alkyl or aryl; and
each R$^3$ is independently alkyl or aryl;
provided that at least one of W and Z is present; if W is present and Z is absent, W is not 4'-hydroxy, and; if Z is present and W is absent, Z is not —OCH$_3$ or —OCOCH$_3$.

Specific examples of compounds having a structure represented by Formula II include Formula (I$_b$), Formula (I$_c$), Formula (I$_g$), and Formula (I$_h$). Another specific embodiment of a compound having a structure represented by Formula (II) is the compound having a structure represented by Formula (II$_a$):

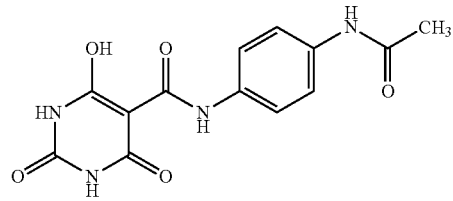

Formula (II$_a$)

wherein X is O, W is absent, and Z is NHC(O)CH$_3$:
N-(4-acetamidophenyl)-6-hydroxy-2,4-dioxo-1,2,3,4-tetrahydropyrimidine-5-carboxamide or 5-(N-(4'-acetamidophenyl))carbamoylbarbituric acid.

Another specific embodiment of a compound having a structure represented by Formula (II) is the compound having a structure represented by Formula (II$_b$):

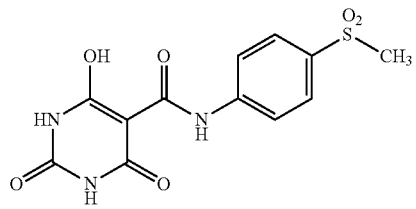

Formula (II$_b$)

wherein X is O, W is absent and Z is S(O)$_2$CH$_3$:
6-hydroxy-N-(4-(methylsulfonyl)phenyl)-2,4-dioxo-1,2,3,4-tetrahydropyrimidine-5-carboxamide or 5-(N-(4'-(methylsulfonyl)phenyl))carbamoylbarbituric acid.

Another specific embodiment of a compound having a structure represented by Formula (II) is the compound having a structure represented by Formula (II$_c$

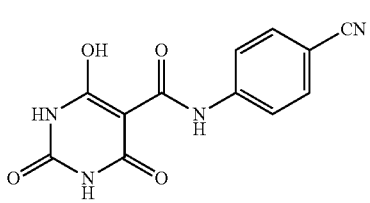

Formula (II$_c$)

wherein X is O, W is absent and Z is —CN:
N-(4-cyanophenyl)-6-hydroxy-2,4-dioxo-1,2,3,4-tetrahydropyrimidine-5-carboxamide or 5-(N-(4'-cyanophenyl))carbamoylbarbituric acid.

Another specific embodiment of a compound having a structure represented by Formula (II) is the compound having a structure represented by Formula (II$_d$):

lp;1p

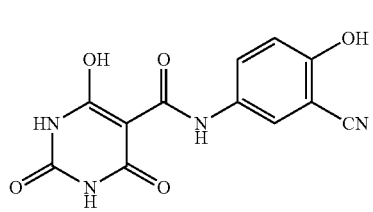

Formula (II$_d$)

wherein X is O, W is present (—OH) and Z is —CN:
N-(3-cyano-4-hydroxyphenyl)-6-hydroxy-2,4-dioxo-1,2,3,4-tetrahydropyrimidine-5-carboxamide or 5-(N-(3'-cyano-4'-hydroxyphenyl))carbamoylbarbituric acid.

Another specific embodiment of a compound having a structure represented by Formula (II) is the compound having a structure represented by Formula (II$_e$):

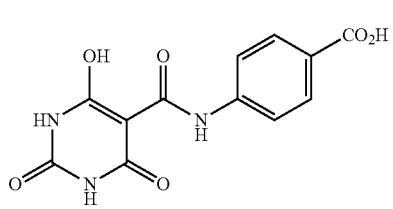

Formula (II$_e$)

wherein X is O, W is absent and Z is —CO$_2$H:
4-(6-hydroxy-2,4-dioxo-1,2,3,4-tetrahydropyrimidine-5-carboxamido)benzoic acid or 5-(N-(4'-carboxyphenyl))carbamoylbarbituric acid.

Another specific embodiment of a compound having a structure represented by Formula (II) is the compound having a structure represented by Formula (II$_f$):

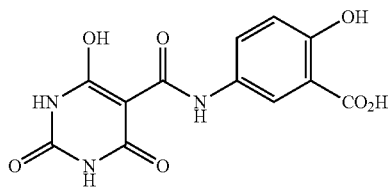

Formula (II$_f$)

wherein X is O, W is present (—OH), and Z is —CO$_2$H:
2-hydroxy-5-(6-oxido-2,4-dioxo-1,2,3,4-tetrahydropyrimidine-5-carboxamido)benzoic acid or 5-(N-(3'-carboxy-4'-hydroxyphenyl))carbamoylbarbituric acid.

Figure 2:
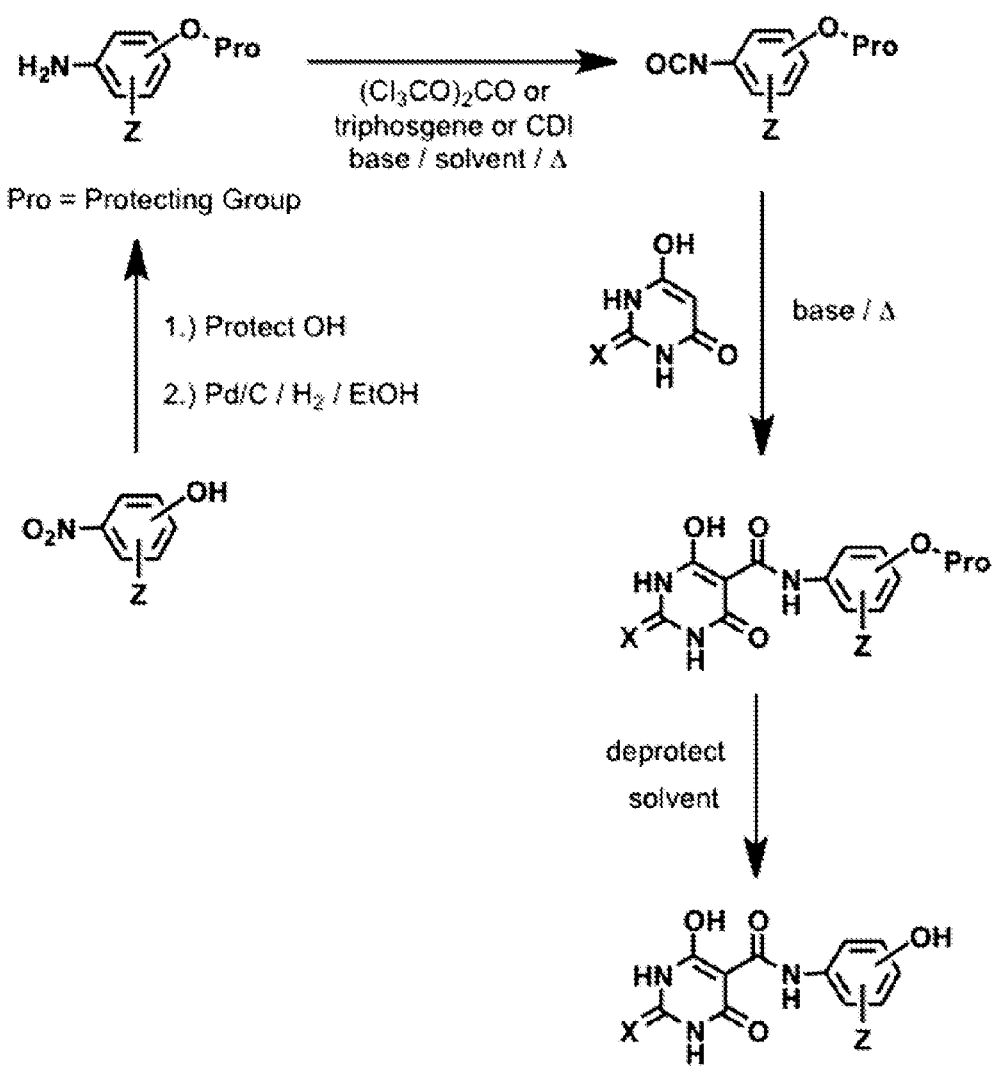
FIG. 2 illustrates a general scheme for synthesis of compounds having a structure represented by Formula (II).

Compounds having structures represented by Formula (II) may be synthesized as shown in FIG. 1 when W is absent and as shown in FIG. 2 when W is present (i.e., W=OH). FIG. 2 is a specific embodiment of FIG. 1 and depicts the embodiment wherein W is OH in the final product. The hydroxyl of the side chain is protected, for example using methods known in the art, and the side chain is activated for coupling to either barbituric acid (X=O) or thiobarbituric acid (X=S) to directly generate compounds represented by Formula (II). In this case, the isocyanate of the appropriately protected phenol is generated from the corresponding aniline by using a variety of methods known in the art, such as reacting the aniline with triphosgene. Alternatively, as depicted in FIG. 1, the activated para-nitrophenylcarbamate of the side chain may be generated by reaction of the substituted aniline with 4-nitrophenyl chloroformate in the presence of base. Reaction of either of these activated side chains with either barbituric acid (X=O) or thiobarbituric acid (X=S) using routine methods, such as in the presence of base, followed by deprotection of the phenol produces the final product.

With reference to the foregoing specific embodiments of compounds having a structure represented by Formula I, it is also to be understood that a further specific embodiment of the compounds of the invention comprises a compound wherein R$^1$ of Formula (I) is heteroaryl (e.g., pyridyl), optionally substituted with W and/or Z. These compounds have a structure represented by Formula (III):

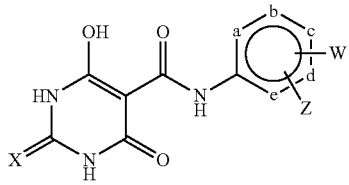

Formula (III)

wherein
X is O or S;
at least one of a, b, c, d, and e is nitrogen;
W if present is one or more hydroxyl moieties;
Z if present is one or more halogen atoms, —CF$_3$, —OR$^2$, —C(O)R$^2$, SR$^2$, —S(O)$_e$R$^3$ where e is 1 or 2, —N(R$^2$)$_2$, —NO$_2$, —CO$_2$R$^2$, —OCO$_2$R$^3$, OC(O)R$^2$, —CON(R$^2$)$_2$, —NR$^2$C(O)R$^2$, —CN, alkyl, aryl, alkenyl or alkynyl;
each R$^2$ is independently H, alkyl or aryl; and
each R$^3$ is independently alkyl or aryl.
Specific examples of compounds having a structure represented by Formula (III) include Formula (I$_f$).

Specific embodiments of compounds having a structure represented by Formula (III) also include the compound having a structure represented by Formula (III$_a$):

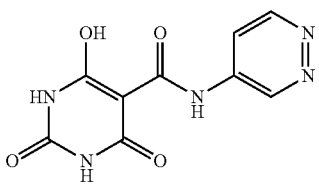

Formula (III$_a$)

wherein X is O; W and Z are absent; c and d are nitrogen, and; a, b, and e are carbon:
6-hydroxy-2,4-dioxo-N-(pyridazin-4-yl)-1,2,3,4-tetrahydropyrimidine-5-carboxamide or 5-(N-(pyridazin-4'-yl))carbamoylbarbituric acid.

Another specific embodiment of a compound having a structure represented by Formula (III) is the compound having a structure represented by Formula (III$_b$):

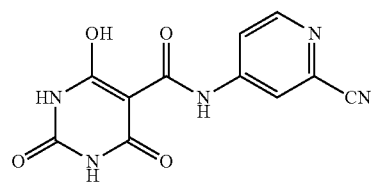

Formula (III$_b$)

wherein X is O; W is absent and Z is —CN; c is nitrogen, and; a, b, d, and e are carbon:
N-(2-cyanopyridin-4-yl)-6-hydroxy-2,4-dioxo-1,2,3,4-tetrahydropyrimidine-5-carboxamide or 5-(N-(2'-cyanopyridin-4'-yl))carbamoylbarbituric acid.

Another specific embodiment of a compound having a structure represented by Formula (III) is the compound having a structure represented by Formula (III$_c$):

Formula (III$_c$)

wherein X is O, W is absent, Z is NH$_2$, and c is nitrogen, and; a, b, d, and e are carbon:
N-(2-aminopyridin-4-yl)-6-hydroxy-2,4-dioxo-1,2,3,4-tetrahydropyrimidine-5-carboxamide or 5-(N-(2'-aminopyridin-4'-yl))carbamoylbarbituric acid.

Figure 3:
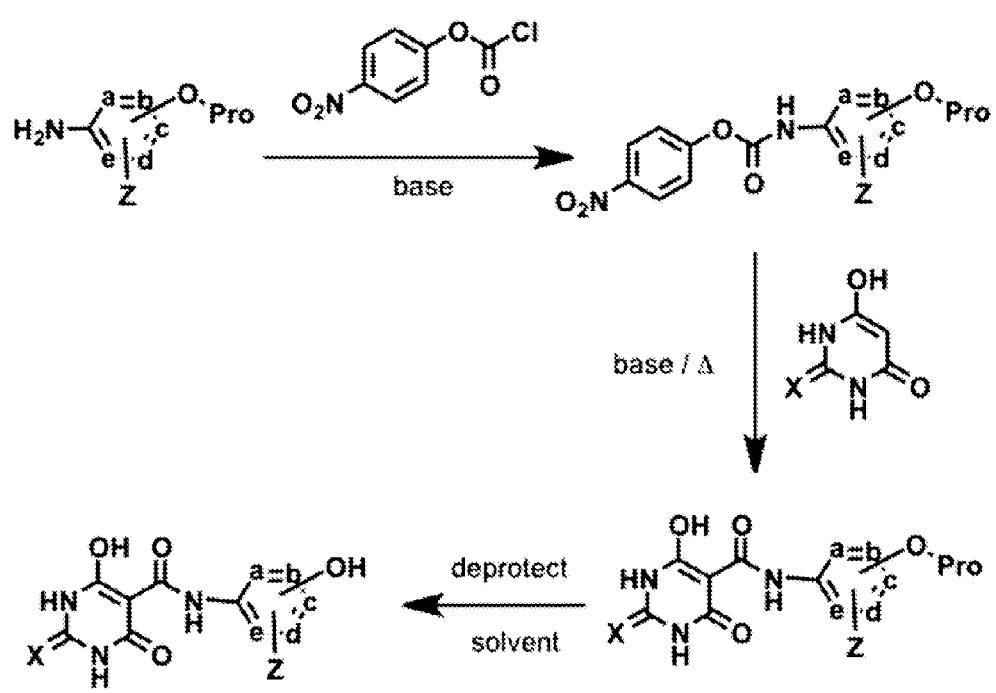
FIG. 3 illustrates a general scheme for synthesis of compounds having a structure represented by Formula (III).

Compounds having structures represented by Formula (III) may be synthesized as shown in FIG. 1 when W is absent and as shown in FIG. 3 when W is present (i.e., W=OH). The illustrated scheme depicts the embodiment wherein W is OH in the final product. This method is a modification of the embodiment for synthesis of compounds represented by Formula (II), and proceeds essentially as shown in FIG. 2, except that the side chain is as shown in Formula (III).

In a second aspect, the invention relates to a compound having a structure represented by Formula (IV):

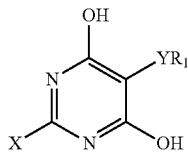

Formula (IV)

wherein
X is H or cyanoamino;
Y is present or absent, and if present is an alkyl group, or a heteroatomic group having from two to twenty atoms, wherein each atom is independently selected from the group consisting of carbon, oxygen, sulfur and nitrogen; and
$R_1$ is substituted or unsubstituted phenyl, substituted or unsubstituted pyrimidyl; substituted or unsubstituted pyridyl; substituted or unsubstituted naphthyl; substituted or unsubstituted purinyl; substituted or unsubstituted thiazole; substituted or unsubstituted oxazole or isoxazole; substituted or unsubstituted cycloalkyl; substituted or unsubstituted benzimidazole or imidazole; substituted or unsubstituted indazole; or substituted or unsubstituted benzoxazole or benzisoxazole Specific embodiments of the compounds having structures represented by Formula (IV) include the following compounds:

1. The compound wherein X is cyanoamino, Y is present and is —CONH—, and $R_1$ is unsubstituted phenyl, for example the compound having a structure represented by Formula (IV$_a$):

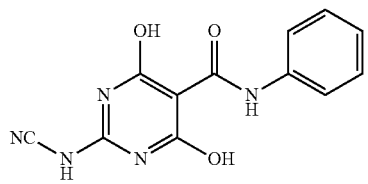

Formula (IV$_a$)

2-cyanoamino-4,6-dihydroxy-N-phenyl-5-pyrimidinecarboxamide or (E)-2-(cyanoimino)-6-hydroxy-4-oxo-N-phenyl-1,2,3,4-tetrahydropyrimidine-5-carboxamide or 2-cyanamido-6-hydroxy-4-oxo-N-phenyl-1,4-dihydropyrimidine-5-carboxamide or 2-cyanoamino-5-(N-phenylcarbamoyl)barbituric acid 2. The compound wherein X is H, Y is present and is —CONH—, and $R_1$ is unsubstituted phenyl, for example the compound having a structure represented by Formula (III$_b$):

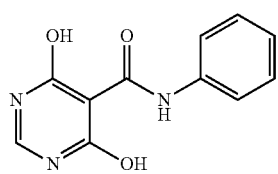

Formula (IV$_b$)

4,6-dihydroxy-N-phenyl-5-pyrimidinecarboxamide or 4-hydroxy-6-oxo-N-phenyl-1,6-dihydropyrimidine-5-carboxamide or 5-(N-phenylcarbamoyl)-2-desoxybarbituric acid.

Figure 4:
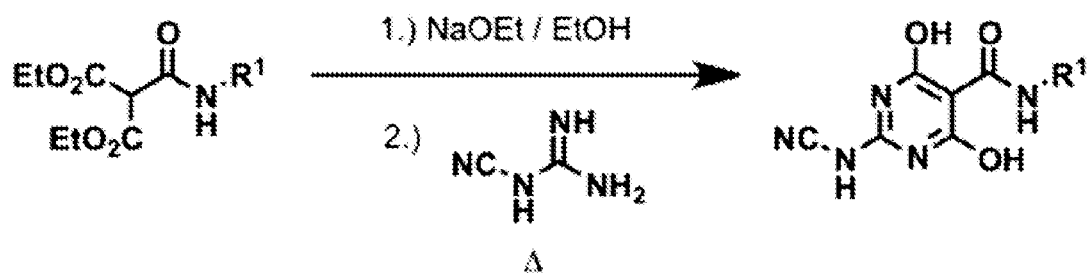
FIG. 4 illustrates a general scheme for synthesis of compounds having a structure represented by Formula (IV), wherein Y is —CONH— and X is cyanoamino (NC—N=) or its tautomer (NC—NH—).

Compounds having structures represented by Formula (IV) may be synthesized as illustrated in FIG. 4. Compounds of this formula may be made in a manner similar to the procedure described in FIG. 5, wherein the appropriately substituted side chain is introduced first to provide the desired malonate derivative. This intermediate is then reacted with cyanoguanidine (instead of either urea or thiourea as described in FIG. 5) under basic conditions, thereby, directly producing compounds of Formula (IV). One skilled in the art will recognize that these cyanoamine derivatives can exist as tautomers (NC—NH— is the tautomer of NC—N=), just as barbituric acid and thiobarbituric acid can exist as a variety of tautomers.

In a first aspect, the invention provides methods for reducing uric acid levels in the blood or serum of a subject comprising administering a compound having a structure represented by Formula (I), Formula (II), Formula (III), Formula (IV), or a combination thereof, to the subject in an amount effective to reduce blood or serum uric acid levels. Typically, the compound having a structure represented by Formula (I), Formula (II), Formula (III), Formula (IV), or a combination thereof, will be administered when the level of uric acid in the blood of the subject is elevated, i.e., in the upper range of normal or above normal levels. One skilled in the art would further recognize that continued administration after normal uric acid levels are achieved is also contemplated in order to maintain uric acid levels within the normal range and to reduce the overall body burden of uric acid that may have occurred due to previously sustained hyperuricemia. Accordingly, methods for preventing elevation of uric acid levels in blood or serum are also an aspect of the invention. Normal uric acid levels in blood are generally in the range of 4.3 mg/dL to 7.0 mg/dL. In certain embodiments, a compound having a structure represented by Formula (I), Formula (II), Formula (III), Formula (IV), or a combination thereof, is administered to a subject with a blood uric acid level of at least about 6 mg/dL. Administration may continue until a blood uric acid level of about 6.0 mg/dL or less is reached; however, it is generally considered to be beneficial to maintain uric acid levels below this target in patients with disorders of uric acid metabolism.

In certain embodiments, the invention provides methods of treating a disorder of uric acid metabolism caused by, or associated with, elevated uric acid levels in blood or serum (hyperuricemia). The method of treating such disorders comprises administering a compound having a structure represented by Formula (I), Formula (II), Formula (III), Formula (IV), or a combination thereof, to a subject in need thereof in an amount effective to reduce serum uric acid levels, thereby treating the disorder of uric acid metabolism in the subject. These disorders are associated with, or caused by, elevated uric acid levels in blood or serum which are in the upper range of normal or above normal, and include gout, hyperuricemia, kidney disease, arthritis, kidney stones, kidney failure, urolithiasis, plumbism, hyperparathyroidism, psoriasis, inborn genetic errors of metabolism, sarcoidosis and cardiovascular disease. These drugs are particularly useful for treating gout and kidney disease (including acute uric acid nephropathy, chronic urate nephropathy, and uric acid nephrolithiasis). In addition, treatment of some cancers with chemotherapy leads to the release of large amounts of uric acid into the blood, which can damage the kidneys. Chemotherapy-induced hyperuricemia, particularly the disorder known as "tumor lysis syndrome," may also be treated, prevented or ameliorated according to the methods of the invention. Administration of a compound having a structure represented by Formula (I), Formula (II), Formula (III), Formula (IV), or a combination thereof, to a subject with hyperuricemia, such as a subject suffering from gout, kidney disease, or a risk of inducing elevated uric acid levels due to chemotherapy, treats, prevents or ameliorates these disorders by reducing uric acid levels in blood, or preventing or controlling their level of increase. In specific embodiments, the disorder of uric acid metabolism treated by administration of a compound having a structure represented by Formula (I), Formula (II), Formula (III), Formula (IV), or a combination thereof, is gout.

The dose of a compound having a structure represented by Formula (I), Formula (II), Formula (III), Formula (IV), or a combination thereof, administered to the subject may be any dose sufficient to achieve a desired reduction in uric acid levels in blood or serum over the time-course of administration. In certain embodiments, a daily dose of about 20 to about 1,500 mg/m$^2$/day is administered. In other embodiments, a daily dose of about 20 to about 500 mg/m$^2$/day, about 20 to about 250 mg/m$^2$/day, about 20 to about 150 mg/m$^2$/day or about 20 to about 100 mg/m$^2$/day is administered. In other embodiments, a daily dose of about 50 to about 1,500 mg/m$^2$/day is administered. In other embodiments, a daily dose of about 50 to about 500 mg/m$^2$/day, about 50 to about 150 mg/m$^2$/day, about 50 to about 100 mg/m$^2$/day, or about 20 to about 100 mg/m$^2$/day is administered.

In certain embodiments of any of the foregoing methods, a compound having a structure represented by Formula (I), Formula (II), Formula (III), Formula (IV), or a combination thereof, is administered to the subject parenterally, intraperitoneally, intravenously, intranasally, intrarectally, or orally. Particularly useful routes of administration include injection, infusion, or oral administration. The amount of the drug administered per dose is an amount sufficient to achieve a reduction in uric acid levels in blood or serum, to prevent elevation of uric acid levels in blood or serum, or to treat or prevent a disorder of uric acid metabolism over the course of therapy. One skilled in the art will recognize that individualization of dosage based on a patient's body composition or his/her hypouricemic response to treatment may be medically necessary or desirable.

The drug(s) may be administered to the subject either intermittently or continuously over a period of time in order to achieve the desired reduction in uric acid levels in blood or serum, or to treat a disorder of uric acid metabolism. For example, doses may be administered intermittently several times per day, or at daily, once, twice or three times per week, or monthly intervals. In a specific example, a compound having a structure represented by Formula (I), Formula (II), Formula (III), Formula (IV), or a combination thereof, may be administered to the subject by continuous intravenous infusion over 24 hours for about five days. Alternatively, a compound having a structure represented by Formula (I), Formula (II), Formula (III), Formula (IV), or a combination thereof, may be administered to the subject by intravenous infusion over about 1 hour to about 5 hours for about five consecutive days. In a specific example, a compound having a structure represented by Formula (I), Formula (II), Formula (III), Formula (IV), or a combination thereof, may be administered to the subject by intramuscular injection or by intravenous infusion over about 10 minutes for about five days. In further specific embodiments, a compound having a structure represented by Formula (I), Formula (II), Formula (III), Formula (IV), or a combination thereof, may be administered to the subject by daily bolus injections for about five consecutive days. The period of time of administration in any of the foregoing protocols may be modified to achieve the desired reduction in uric acid levels, including about 2 days, about 3 days, about 4 days, about one week or about two weeks of administration, and these treatments may be repeated at intervals of every two to every 10 weeks.

In addition to continuous intravenous infusion or bolus injection, a compound having a structure represented by Formula (I), Formula (II), Formula (III), Formula (IV), or a combination thereof, may be administered to the subject orally. In this embodiment, an oral dose in amounts as described above may be administered in one, two, three or four administrations per day for 1, 2, 3, 4, or 5 days to achieve the desired reduction in uric acid levels. In further embodiments, the oral dose as described above may be administered once per day, or in one, two, three or four administrations per day for one week or two weeks, or intermittently for longer periods of time in similar treatment cycles, to achieve the desired reduction in uric acid levels.

It will be appreciated that a subject in need of reduced levels of uric acid in blood or serum, or in need of treatment of a disorder of uric acid metabolism, will be treated more aggressively initially to achieve the desired reduction in uric acid levels. Following initial therapy and reduction of uric acid levels to normal or sub-normal levels, the subject may be further treated over a period of time, or over a lifetime, to maintain normal or sub-normal levels of uric acid in blood or serum and prevent elevation of uric acid levels subsequent to the initial treatment. The maintenance or preventive protocol may comprise reduced dosages and/or less frequent administration of a compound having a structure represented by Formula (I), Formula (II), Formula (III), Formula (IV), or a combination thereof, as necessary or desired to maintain normal or sub-normal uric acid levels in blood or serum. For example, in a maintenance protocol the drug(s) may be administered daily, weekly, monthly, or intermittently as uric acid levels rise between treatment periods. Such maintenance protocols will serve to maintain normal or sub-normal uric acid levels for a prolonged period of time and reduce the subject's lifetime risk of developing a disorder of uric acid metabolism caused by, or associated with, prolonged hyperuricemia. The initial reduction of uric acid levels from above normal or high normal to normal or sub-normal, and maintenance of normal or sub-normal uric acid levels are both features included in treatment of a disorder of uric acid metabolism. It is anticipated that in certain embodiments, a typical patient will require daily treatment of varying duration, and that such daily treatment may be provided intermittently for life or for extended periods.

In certain embodiments of any of the foregoing methods, blood or serum uric acid levels of the subject are reduced by at least 25% compared to uric acid levels prior to administration of a compound having a structure represented by Formula (I), Formula (II), Formula (III), Formula (IV), or a combination thereof. In certain further embodiments, blood or serum uric acid levels of the subject are reduced by 50% or more compared to levels prior to administration. In a specific embodiment, uric acid levels are reduced by about 75% even at daily doses of 500 mg/m$^2$/day or less.

In a second aspect of the invention methods are provided for treating a disorder of uric acid metabolism associated with, or caused by, elevated uric acid in blood or serum comprising administering to a subject in need thereof a compound having a structure represented by Formula (I), Formula (II), Formula (III), Formula (IV), or a combination thereof, in an amount effective to reduce blood or serum uric acid levels, thereby treating the disorder of uric acid metabolism. Specific embodiments of the methods for treating a disorder of uric acid metabolism relating to dosing, routes of administration, initial therapy and maintenance therapy are as described above for reducing uric acid levels in blood or serum. The initial reduction in uric acid levels is typically rapid, and often occurs within 1-5 days. Upon reduction in uric acid levels to normal or sub-normal levels, continued maintenance or preventive therapy results in a detectable improvement in at least one symptom of elevated uric acid, for example reduced inflammation, reduced pain, slowing of development of deformities, reduced development of kidney stones, prevention of tumor lysis syndrome, or improvement in cardiovascular disease. One skilled in the art will recognize that prevention of recurrent symptoms due to recurrence of elevated serum uric acid levels, thereby necessitating extended treatment, would be highly desirable to maximize patient benefit.

A further aspect of the invention provides a pharmaceutical composition comprising a compound having a structure represented by Formula (I), Formula (II), Formula (III), Formula (IV), or a combination thereof, and a pharmaceutically acceptable carrier. In certain embodiments of the pharmaceutical compositions, the composition is formulated as a solution or tablet. Solutions or dispersions of the drug(s) can be prepared in water or saline. In certain embodiments of the pharmaceutical compositions, the pharmaceutically acceptable carrier is one or more component selected from the group consisting of one or more of a solvent, a dispersing agent, a coating (e.g., lecithin), a surfactant (e.g., hydroxypropylcellulose), a preservative (e.g., paraben, phenol, thimerosal, sorbic acid, chlorobutanol), an emulsion, an alcohol (e.g., ethanol), a polyol (e.g., glycerol, propylene glycol), and an isotonic agent (e.g., sugars, sodium chloride).

In certain embodiments of the foregoing pharmaceutical compositions, the composition is formulated for controlled release of the compound having a structure represented by Formula (I), Formula (II), Formula (III), Formula (IV), or a combination thereof. In certain embodiments of the foregoing methods, a compound having a structure represented by Formula (I), Formula (II), Formula (III), Formula (IV), or a combination thereof, is administered in a form for controlled release, formulation, i.e., a formulation that releases the active ingredient more slowly or prolongs the duration of its action within the body. The controlled release compositions may include pharmaceutically acceptable carriers or excipients that delay absorption (e.g., aluminum monostearate, gelatin, natural or synthetic hydrophilic gums). Alternatively, controlled release of the pharmaceutical composition may employ a device such as a pump, implant or transdermal patch. These formulations and devices provide a slow release of the active ingredient and extend the duration of its action within the body.

In certain embodiments of the foregoing pharmaceutical compositions, the composition is formulated for improved oral bioavailability or extended release in the body. For example, microemulsions, particle size reduction and complexation technologies may be used to improve dissolution rates or equilibrium solubilities of the compounds. Other suitable chemical and physical means for improving oral bioavailability or extended release will also be known to those skilled in the art.

EXAMPLES

Example 1

Figure 7:
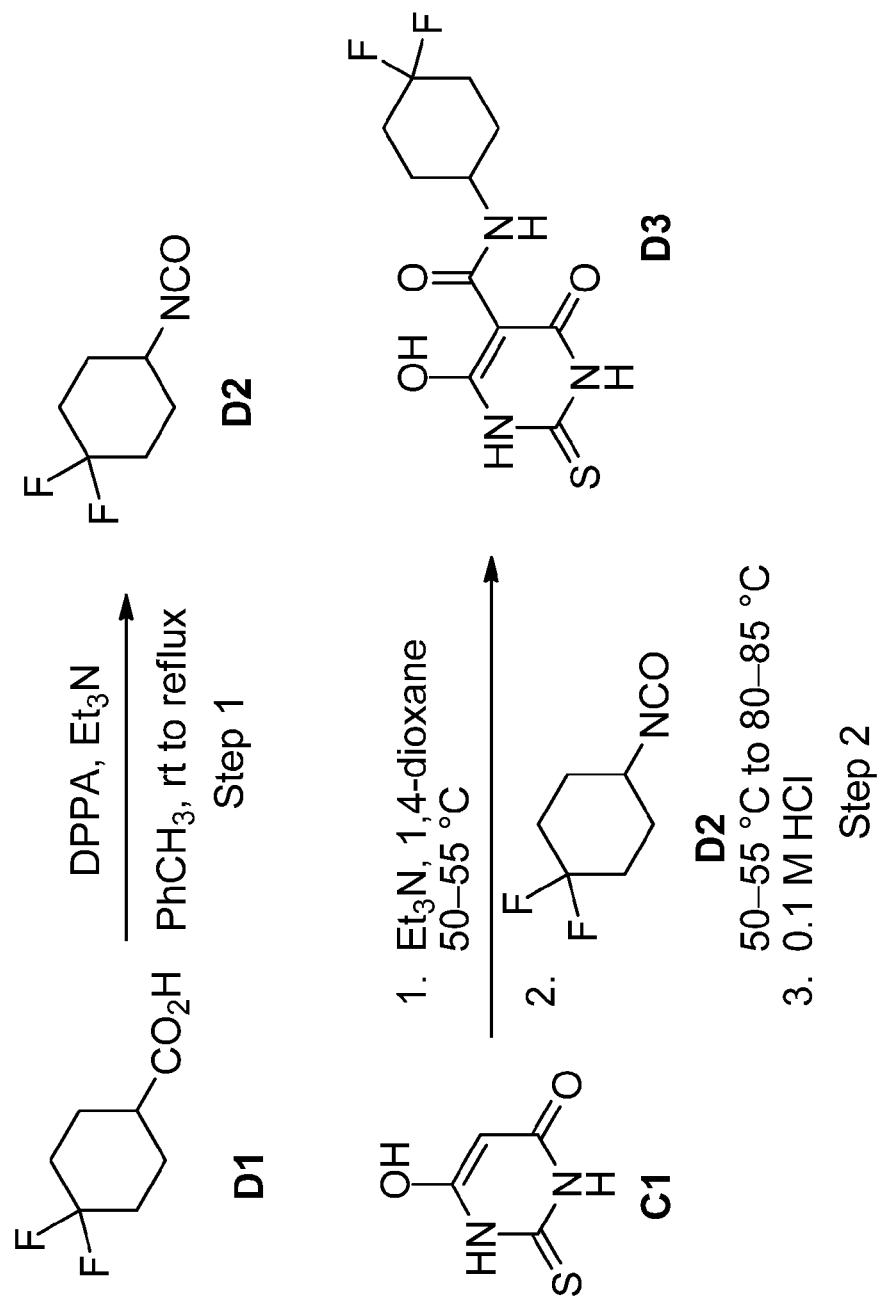
FIG. 7 illustrates synthesis of the compound represented by Formula ($I_a$), described in Example 1.

Preparation of N-(4,4-difluorocyclohexyl)-6-hydroxy-4-oxo-2-thioxo-1,2,3,4-tetrahydropyrimidine-5-carboxamide (Formula ($I_a$), shown as D3 in FIG. 7). The following reaction steps correspond to the steps and compounds shown in FIG. 7.

Step One. 1,1-Difluoro-4-isocyanatocyclohexane (D2)

To the stirred solution of 4,4-difluorocyclohexanecarboxylic acid (D1) (2.95 g, 18.0 mmol) and triethylamine (2.19 g, 21.6 mmol) in anhydrous toluene (50 mL) at room temperature under nitrogen was added diphenyl phosphorazidate (DPPA) (5.44 g, 19.8 mmol) dropwise. After addition, the reaction mixture was heated to reflux for 4 h. After this time, the reaction mixture was cooled to room temperature, washed with water (20 mL), saturated aqueous sodium bicarbonate (20 mL), and brine (20 mL), dried over anhydrous sodium sulphate, and filtered. The filtrate was used for the subsequent step reaction without further purification and characterization.

Step Two. N-(4,4-Difluorocyclohexyl)-6-hydroxy-4-oxo-2-thioxo-1,2,3,4-tetrahydropyrimidine-5-carboxamide (D3)

The stirred mixture of compound C1 (2.59 g, 18.0 mmol) in 1,4-dioxane (100 mL) was heated at 50-55° C. for 25 min under nitrogen. Then to the resulting mixture was added triethylamine (1.82 g, 18.0 mmol) in 1,4-dioxane (15 mL) dropwise over 30 min. After that addition, to the reaction mixture was added the stock solution of D2 (18.0 mmol in 50 mL toluene) dropwise over 25 min. Then to the reaction mixture was added another portion of 1,4-dioxane (30 mL). The resulting reaction mixture was heated to 80-85° C. and stirred overnight at this temperature. After this time, the hot reaction mixture was poured into 0.1 M aqueous hydrochloric acid (650 mL). The resulting mixture was stirred for 30 min and then filtered. The filter cake was washed with water (3×50 mL) and dried under high vacuum to afford crude D3, which then was crystalized with 1,4-dioxane/water to afford compound D3 (3.09 g, 56%) as a light purple solid: mp>300° C.; $^1$H NMR (300 MHz, DMSO-$d_6$) δ 12.66 (bs, 2H), 9.56 (d, J=8.1 Hz, 1H), 4.04-3.90 (m, 1H), 2.08-1.83 (m, 6H), 1.76-1.58 (m, 2H). MS (M−H) 304.

Example 2

Figure 8:
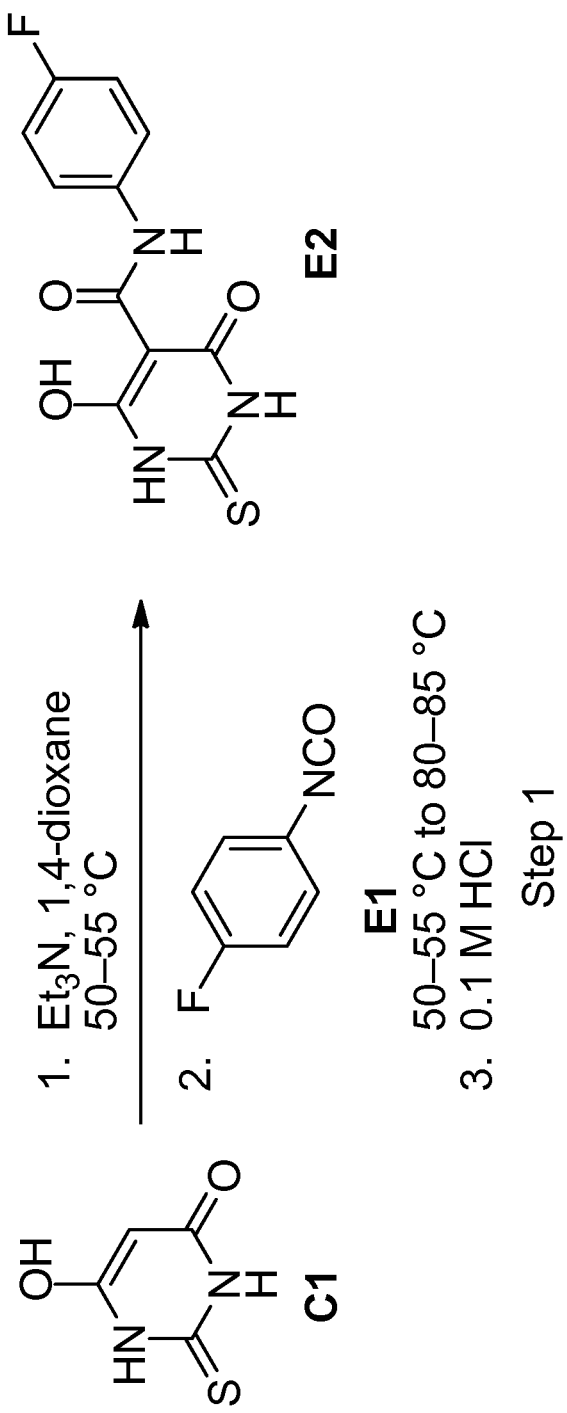
FIG. 8 illustrates synthesis of the compound represented by Formula ($I_b$), described in Example 2.

Preparation of N-(4-Fluorophenyl)-6-hydroxy-4-oxo-2-thioxo-1,2,3,4-tetrahydropyrimidine-5-carboxamide (Formula ($I_b$), shown as E2 in FIG. 8). The following reaction steps correspond to the steps and compounds shown in FIG. 8.

Step One. N-(4-Fluorophenyl)-6-hydroxy-4-oxo-2-thioxo-1,2,3,4-tetrahydropyrimidine-5-carboxamide (E2)

The compound E2 was prepared by following the procedure of Example 1, Step 2 from C1 (2.02 g, 14.0 mmol) and compound E1 to afford compound E2 (2.24 g, 57%) as a white solid: mp>300° C.; $^1$H NMR (300 MHz, DMSO-$d_6$)

δ 12.99 (bs, 2H), 11.36 (s, 1H), 7.63-7.55 (m, 2H), 7.26 (t, J=8.7 Hz, 2H). MS (M−H) 280.

Example 3

Figure 9:
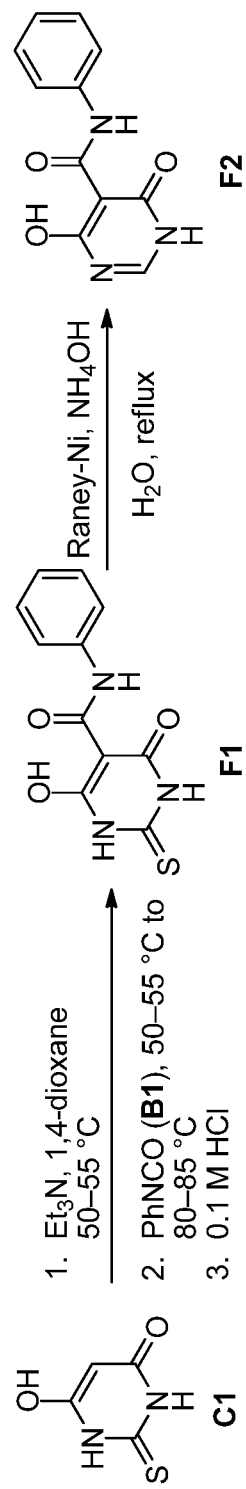
FIG. 9 illustrates synthesis of the compound represented by Formula ($IV_b$), described in Example 3.

Preparation of 4-hydroxy-6-oxo-N-phenyl-1,6-dihydropyrimidine-5-carboxamide (Formula (IV$_b$), shown as F2 in FIG. 9). The following reaction steps correspond to the steps and compounds shown in FIG. 9.

Step One. 6-Hydroxy-4-oxo-N-phenyl-2-thioxo-1,2,3,4-tetrahydropyrimidine-5-carboxamide (F1)

The compound F1 was prepared by following the procedure of Example 1, Step 2 from C1 (3.03 g, 21.0 mmol) and compound B1 to afford compound F1 (4.65 g, 84%) as a white solid: $^1$H NMR (300 MHz, DMSO-d$_6$) δ 12.99 (bs, 2H), 11.43 (s, 1H), 7.55 (d, J=7.8 Hz, 2H), 7.46-7.38 (m, 2H), 7.26-7.20 (m, 1H).

Step Two. 4-hydroxy-6-oxo-N-phenyl-1,6-dihydropyrimidine-5-carboxamide (F2)

To the stirred suspension of compound F1 (3.13 g, 11.9 mmol) in water (95 mL) and concentrated ammonium hydroxide (95 mL) under nitrogen at room temperature was added Raney nickel (11.9 g). After addition, the reaction mixture was heated to reflux for 4 h. After this time, the reaction mixture was cooled to room temperature and acidified by slow addition of 1 M aqueous hydrochloric acid to pH<2. The resulting mixture was filtered. The filter cake was extracted with 2 M aqueous sodium hydroxide (3×100 mL). The combined extracts were acidified to pH<2 with 1.5 M aqueous hydrochloric acid. The resulting precipitates were collected by vacuum filtration. The filter cake was washed with water (2×30 mL) and dried under high vacuum to give a white solid which was dissolved in concentrated ammonium hydroxide (80 mL) and filtered. The filtrate was slowly acidified with 1 M aqueous hydrochloric acid to pH<2. The resulting precipitates were collected by vacuum filtration. The filter cake was then dissolved in 2 M aqueous sodium hydroxide (50 mL) and purified by C18 column chromatography eluting with 10% methanol/water to provide pure sodium salt of compound F2. The purified sodium salt of F2 was acidified with 0.5 M aqueous hydrochloride acid to pH<2. The resulting solid was filtered. The filter cake was washed with water (3×30 mL) and dried under high vacuum to afford compound F2 (0.809 g, 29%) as a white solid: mp 230-233° C.; $^1$H NMR (300 MHz, DMSO-d$_6$) δ 15.45 (bs, 1H), 13.20 (bs, 1H), 11.83 (s, 1H), 8.34 (s, 1H), 7.62 (d, J=7.8 Hz, 2H), 7.40 (t, J=7.8 Hz, 2H), 7.22-7.16 (m, 1H). MS (M−H) 230.

Example 4

Figure 10:
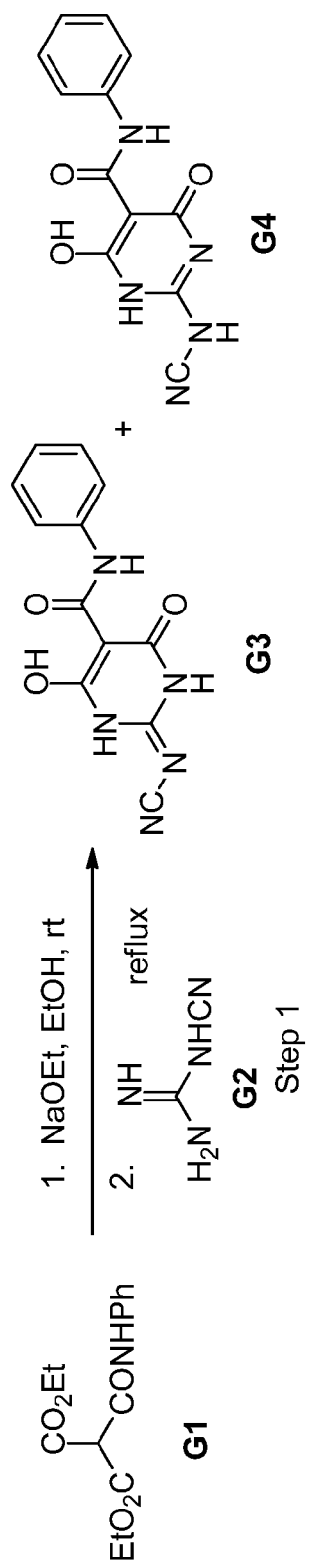
FIG. 10 illustrates synthesis of the compound represented by Formula ($IV_a$), described in Example 4.

Preparation of (E)-2-(cyanoimino)-6-hydroxy-4-oxo-N-phenyl-1,2,3,4-tetrahydropyrimidine-5-carboxamide (the NC—N=tautomer of Formula (IV$_a$), shown as G3 in FIG. 10) and 2-cyanamido-6-hydroxy-4-oxo-N-phenyl-1,4-dihydropyrimidine-5-carboxamide (Formula (IV$_a$), shown as G4 in FIG. 10). The following reaction steps correspond to the steps and compounds shown in FIG. 10.

Step One. (E)-2-(Cyanoimino)-6-hydroxy-4-oxo-N-phenyl-1,2,3,4-tetrahydropyrimidine-5-carboxamide (G3) and 2-cyanamido-6-hydroxy-4-oxo-N-phenyl-1,4-dihydropyrimidine-5-carboxamide (G4)

To ethanol (85 mL) was added sodium (0.543 g, 23.6 mmol). The resulting suspension was stirred at room temperature under nitrogen until a clear solution was obtained. To this solution was added compound G1 (3.00 g, 10.7 mmol) followed by compound G2 (1.08 g, 12.8 mmol). The resulting mixture was heated to reflux for 6 h and then cooled to room temperature. The reaction was quenched with acetic acid (1.4 mL) and concentrated to dryness. The resulting residue was dissolved in water (140 mL) and then acidified by 2 M aqueous hydrochloric acid to pH<2. The resulting precipitates were collected by vacuum filtration. The filter cake was washed with water (3×10 mL) and dried under high vacuum to give a light yellow solid which was further purified by trituration with a mixture of methanol and methylene chloride (1:1, 50 mL), filtered, and dried under high vacuum to provide a mixture of tautomers (G3/G4=1.2:1) (2.23 g, 77%) as an off-white solid: mp 278-280° C.; $^1$H NMR (500 MHz, DMSO-d$_6$) δ 12.36 (bs, 1.1H), 12.13 (bs, 0.6H), 9.71 (bs, 0.45H), 9.11 (bs, 0.54H), 7.91 (bs, 2H), 7.58-7.51 (m, 3H), 5.18 (bs, 0.45H). MS (M−H) 270.

Example 5

Figure 11:
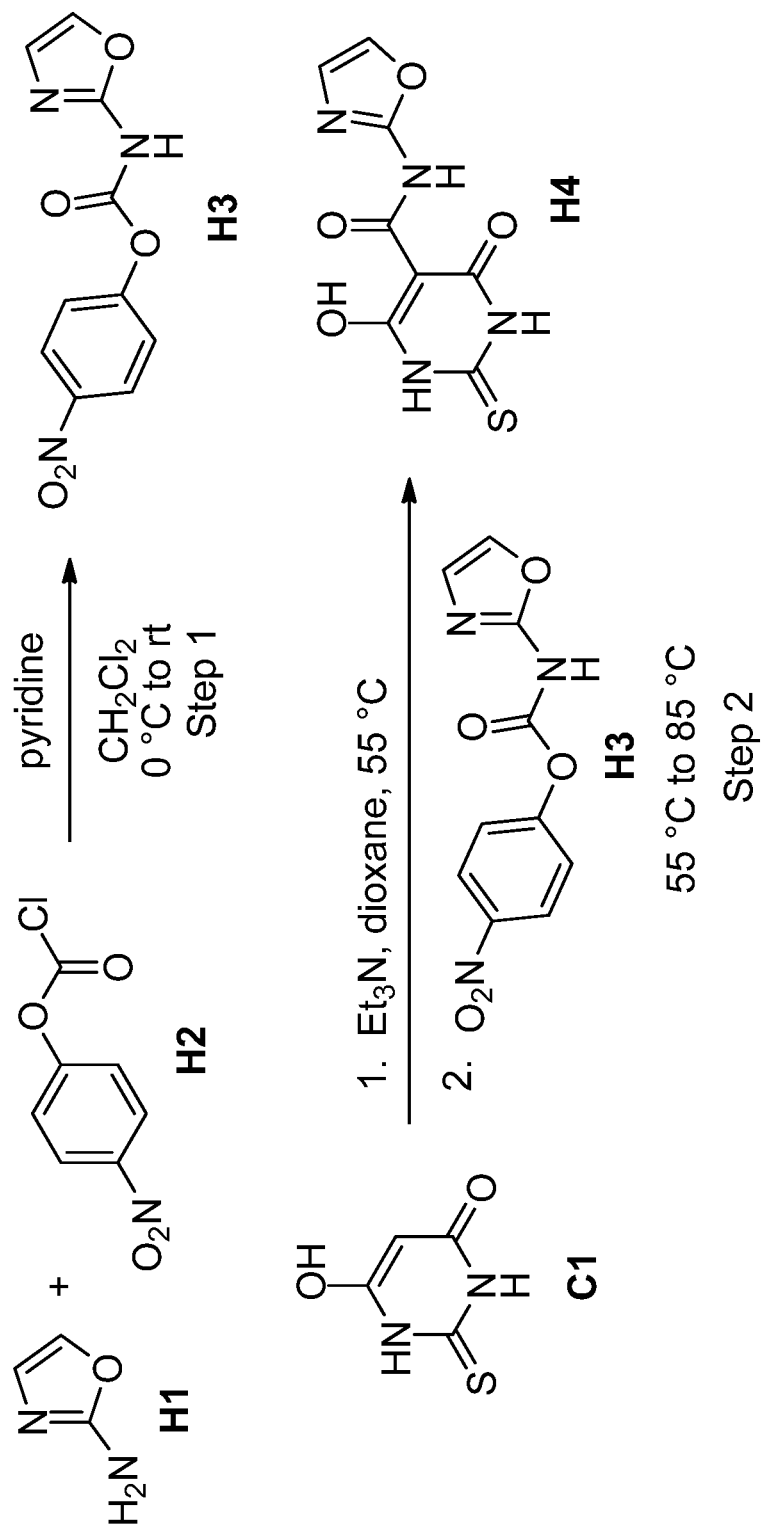
FIG. 11 illustrates synthesis of the compound represented by Formula ($I_e$), described in Example 5.

Preparation of 6-hydroxy-N-(oxazol-2-yl)-4-oxo-2-thioxo-1,2,3,4-tetrahydropyrimidine-5-carboxamide (Formula (I$_e$), shown as H4 in FIG. 11). The following reaction steps correspond to the steps and compounds shown in FIG. 11.

Step One. 4-Nitrophenyl oxazol-2-ylcarbamate (H3)

To a stirred solution of compound H2 (10.1 g, 50.0 mmol) in anhydrous methylene chloride (50 mL) was added a solution of compound H1 (4.20 g, 50.0 mmol) and pyridine (4.16 g, 52.5 mmol) in anhydrous methylene chloride (70 mL) dropwise over 15 min at 0° C. under nitrogen. After the addition, the reaction mixture was warmed to room temperature and stirred for 20 h. The resulting mixture was filtered. The filter cake was washed with anhydrous methylene chloride (2×10 mL), dried under high vacuum to give compound H3 (4.88 g, 39%) as an off-white solid: MS (M+H) 250.

Step Two. 6-hydroxy-N-(oxazol-2-yl)-4-oxo-2-thioxo-1,2,3,4-tetrahydropyrimidine-5-carboxamide (H4)

To a stirred mixture of compound C1 (2.40 g, 16.6 mmol) in 1,4-dioxane (160 mL) was added a solution of triethylamine (2.54 g, 25.1 mmol) in 1,4-dioxane (32 mL) dropwise over 25 min at 55° C. under nitrogen. After the addition, the reaction mixture was stirred at 55° C. for 30 min and then compound H3 (4.15 g, 16.6 mmol) was added. The resulting mixture was stirred at 55° C. for 1 h and then heated to 85° C. for an additional 5 h. After this time, the reaction mixture was cooled to room temperature overnight. The resulting suspension was filtered and the filter cake was washed with a mixture of methanol and 1,4-dioxane (1:1, 50 mL). The combined filtrates were concentrated. The residue was dissolved in 0.1 M aqueous sodium hydroxide (100 mL) and purified by C18 column chromatography eluting with 10% methanol/water. The purified sodium salt of H4 was acidified with 2 M aqueous hydrochloride acid to pH<2. The resulting solid was filtered, washed with water (3×20 mL), and dried under high vacuum to afford compound H4 (1.07 g, 25%) as a light yellow solid: mp 255-257° C. (dec.); $^1$H NMR (300 MHz, DMSO-d$_6$) δ 13.59 (bs, 1H), 12.06 (bs, 2H), 8.05 (d, J=1.2 Hz, 1H), 7.43 (d, J=1.2 Hz, 1H). MS (M−H) 253.

Example 6

Figure 12:
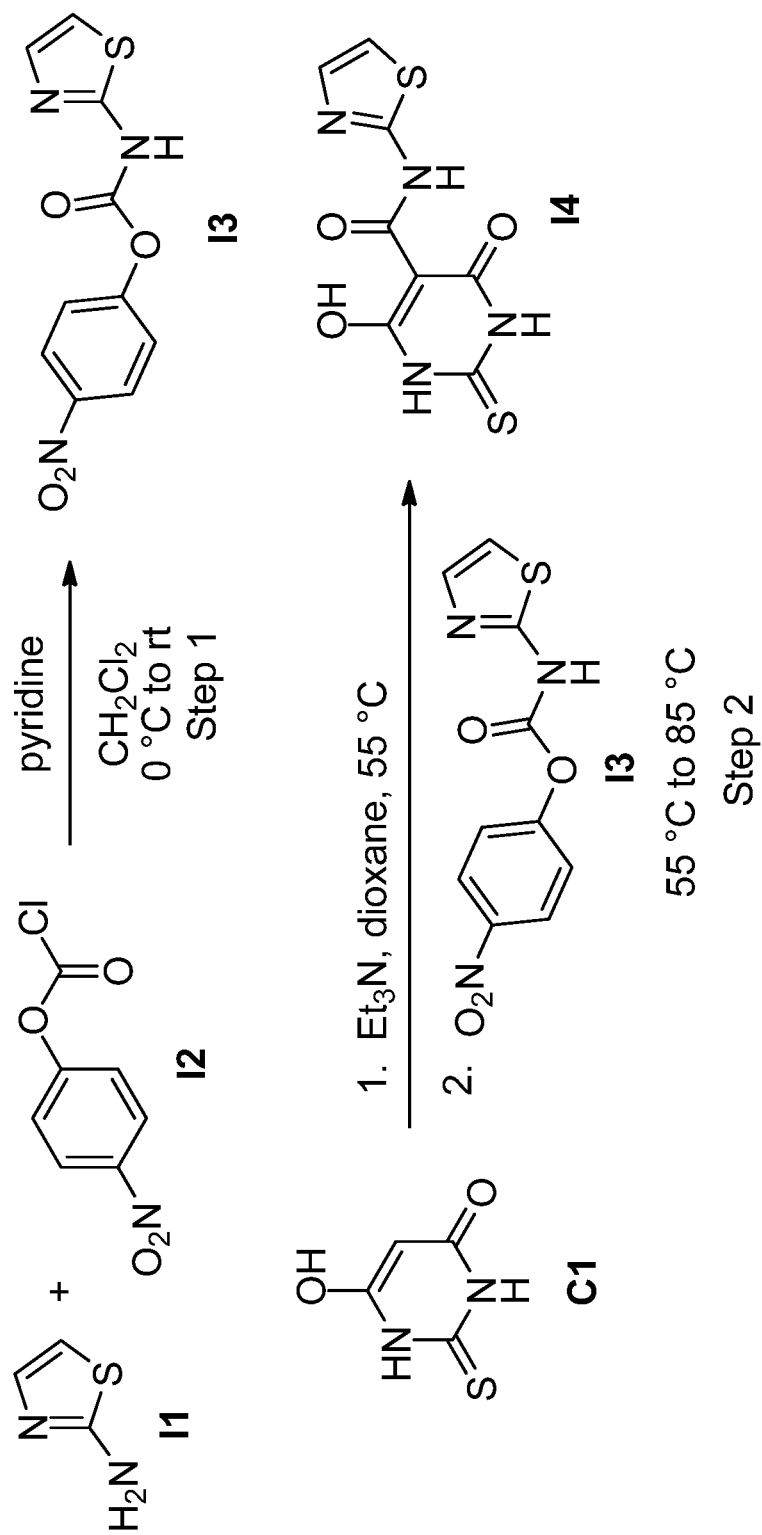
FIG. 12 illustrates synthesis of the compound represented by Formula ($I_d$), described in Example 6.

Preparation of 6-hydroxy-4-oxo-N-(thiazol-2-yl)-2-thioxo-1,2,3,4-tetrahydropyrimidine-5-carboxamide (Formula ($I_d$), shown as 14 in FIG. 12). The following reaction steps correspond to the steps and compounds shown in FIG. 12.

Step One. 4-Nitrophenyl thiazol-2-ylcarbamate (I3)

The compound I3 was prepared by following the procedure of Example 5, Step 1 from I1 (1.00 g, 9.99 mmol) and compound I2 to afford compound I3 (0.885 g, 33%) as an off-white solid: $^1$H NMR (300 MHz, DMSO-$d_6$) δ 11.06 (bs, 1H), 8.12 (d, J=9.0 Hz, 2H), 7.41 (d, J=3.6 Hz, 1H), 7.16 (d, J=3.6 Hz, 1H), 6.94 (d, J=9.0 Hz, 2H). MS (M+H) 266.

Step Two. 6-Hydroxy-4-oxo-N-(thiazol-2-yl)-2-thioxo-1,2,3,4-tetrahydropyrimidine-5-carboxamide (I4)

The compound I4 was prepared by following the procedure of Example 5, Step 2 from C1 (2.64 g, 18.3 mmol) and compound I3 to afford compound I4 (1.04 g, 21%) as a yellow solid: mp>300° C.; $^1$H NMR (300 MHz, DMSO-$d_6$) δ 13.56 (s, 1H), 11.57 (bs, 2H), 7.52 (d, J=3.9 Hz, 1H), 7.19 (d, J=3.9 Hz, 1H). MS (M−H) 269.

Example 7

Figure 13:
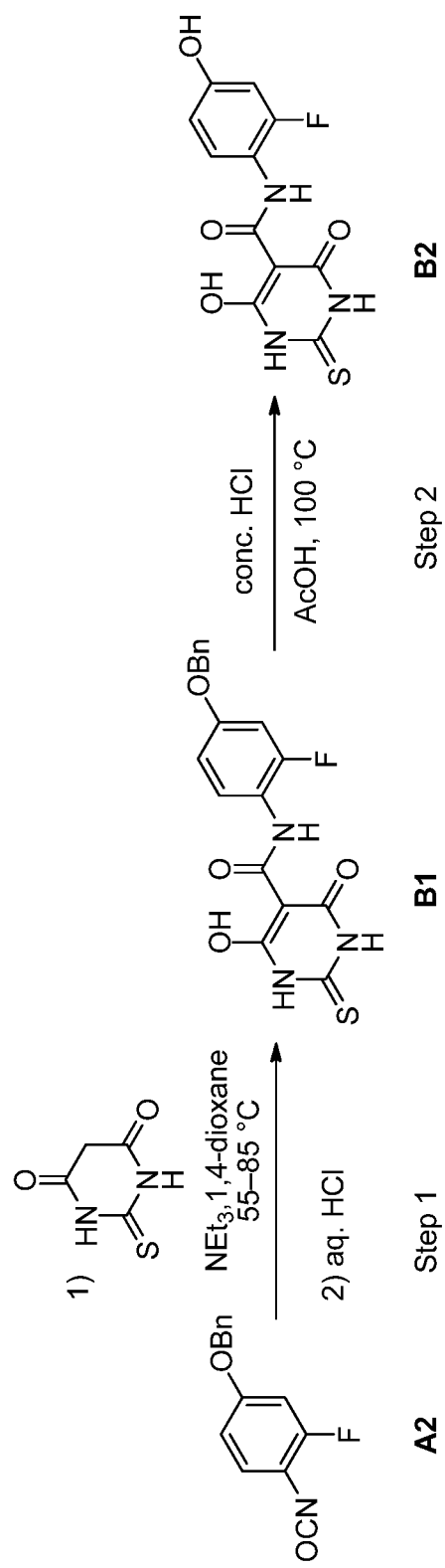
FIG. 13 illustrates synthesis of the compound represented by Formula ($I_c$), described in Example 7.

Preparation of N-(2-fluoro-4-hydroxyphenyl)-6-hydroxy-4-oxo-2-thioxo-1,2,3,4-tetrahydropyrimidine-5-carboxamide (Formula ($I_c$), shown as B2 in FIG. 13). The following reaction steps correspond to the steps and compounds shown in FIG. 13.

Step One. N-(4-(benzyloxy)-2-fluorophenyl)-6-hydroxy-4-oxo-2-thioxo-1,2,3,4-tetrahydropyrimidine-5-carboxamide (B1)

Compound B1 was prepared following the procedure of Example 9, Step 2 from compound A2 (935 mg, 3.85 mmol), 2-thioxodihydropyrimidine-4,6(1H,5H)-dione (554 mg, 3.85 mmol), and triethylamine (0.53 mL, 3.85 mmol) to afford compound B1 (1.22 g, 82%) as a tan solid: $^1$H NMR (500 MHz, DMSO-$d_6$) δ 12.92 (br s, 2H), 11.35 (s, 1H), 7.85 (t, J=9.1 Hz, 1H), 7.46-7.33 (m, 5H), 7.11 (dd, J=12.7, 2.8 Hz, 1H), 6.91 (d, J=Hz, 1H), 5.13 (s, 2H).

Step Two. N-(2-fluoro-4-hydroxyphenyl)-6-hydroxy-4-oxo-2-thioxo-1,2,3,4-tetrahydropyrimidine-5-carboxamide (B2)

A mixture of compound B1 (590 mg, 1.52 mmol), concentrated hydrochloric acid (2 mL), and acetic acid (6 mL) was heated at 100° C. in a sealed tube. After this time, the reaction mixture was cooled to rt and filtered. The collected solid was dissolved in 0.1 M aqueous sodium hydroxide (100 mL) and purified by C18 column chromatography eluting with 10% methanol/water. The purified sodium salt of B2 was acidified with 2 M aqueous hydrochloride acid to pH<2. The resulting solid was filtered, washed with water (3×10 mL), and dried under high vacuum to afford compound B2 (82 mg, 18%) as a light brown solid: mp>250° C.; $^1$H NMR (500 MHz, DMSO-$d_6$) δ 12.88 (br s, 2H), 11.29 (s, 1H), 10.00 (s, 1H), 7.70 (br s, 1H), 6.72 (d, J=12.0 Hz, 1H), 6.64 (d, J=8.0 Hz, 1H). ESI MS, m/z 296 [M−H]$^-$.

Example 8

Figure 14:
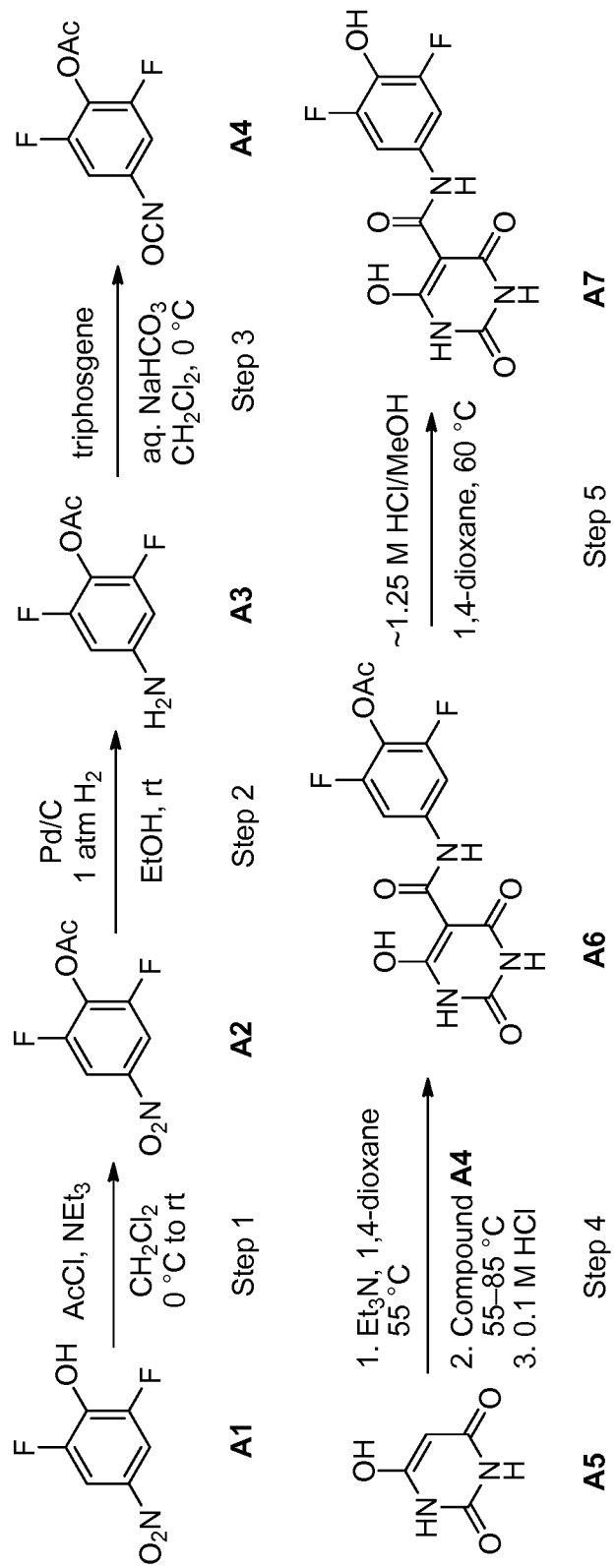
FIG. 14 illustrates synthesis of the compound represented by Formula ($I_g$), described in Example 8.

Preparation of N-(3,5-difluoro-4-hydroxyphenyl)-6-hydroxy-2,4-dioxo-1,2,3,4-tetrahydropyrimidine-5-carboxamide (Formula ($I_g$), shown as A7 in FIG. 14). The following reaction steps correspond to the steps and compounds shown in FIG. 14.

Step One. 2,6-Difluoro-4-nitrophenyl acetate (A2)

To an ice-cooled solution of 2,6-difluoro-4-nitrophenol A1 (175 mg, 1.00 mmol) and triethylamine (152 uL, 1.10 mmol) in dichloromethane (3 mL) was added acetyl chloride (79 uL, 1.10 mmol) dropwise with stirring. Additional dichloromethane (3 mL) was added and the mixture allowed to warm to rt over 2 h. After this time, the reaction mixture was adsorbed on silica (~10 mL). The crude material was purified by chromatography (silica, 0-25% ethyl acetate/hexanes) to afford A2 (120 mg, 55%) as a white solid: $^1$H NMR (500 MHz, DMSO-$d_6$) δ 8.31 (m, 2H), 2.47 (s, 3H).

Step Two. 4-Amino-2,6-difluorophenyl acetate (A3)

A mixture of A2 (560 mg, 2.58 mmol) and 10% palladium on carbon (100 mg) in ethanol (20 mL) was stirred under 1 atmosphere of hydrogen at rt for 16 h. After this time, the reaction mixture was filtered and concentrated under reduced pressure. The residue obtained was purified by chromatography (silica, 0-50% ethyl acetate/hexanes) to afford compound A3 (450 mg, 93%) as a light yellow oil: $^1$H NMR (500 MHz, CDCl3) δ 6.22 (m, 2H), 3.80 (br s, 2H), 2.32 (s, 3H).

Step Three. 2,6-Difluoro-4-isocyanatophenyl acetate (A4)

To a stirred, ice-cooled mixture of A3 (187 mg, 1.00 mmol), saturated aqueous sodium bicarbonate (10 mL), and dichloromethane (10 mL) was added triphosgene (119 mg, 0.400 mmol) in dichloromethane (0.5 mL). After 0.5 h, the dichloromethane layer was dried over magnesium sulfate, the drying agent was removed by filtration, and the resulting solution was concentrated under reduced pressure to afford A4 (151 mg, 71%) as a light yellow solid: $^1$H NMR (500 MHz, CDCl3) δ 6.74 (m, 2H), 2.37 (s, 3H).

Step Four. 2,6-difluoro-4-(6-hydroxy-2,4-dioxo-1,2,3,4-tetrahydropyrimidine-5-carboxamido)phenyl acetate (A6)

To a suspension of pyrimidine-2,4,6(1H,3H,5H)-trione A5 (349 mg, 2.72 mmol) in 1,4-dioxane (5 mL) was added triethylamine (0.37 mL, 2.7 mmol) dropwise at 55° C. After 10 min a solution of compound A4 (580 mg, 2.72 mmol) in 1,4-dioxane (5 mL) was added over 45 min with stirring. The mixture was stirred and heated at 55° C. for an additional 1 h and then warmed to 85° C. for 2 h. After this time, the mixture was cooled to rt, slowly poured into 0.1 N aqueous hydrochloric acid (45 mL) and stirred for 10 min. The resulting solid was collected by filtration and dried under reduced pressure to afford compound A6 (637 mg, 69%) as a yellow solid: $^1$H NMR (500 MHz, DMSO-$d_6$) δ 11.85 (br s, 2H), 11.54 (s, 1H), 7.56 (d, J=9.5 Hz, 2H), 2.40 (s, 3H).

Step Five. N-(3,5-difluoro-4-hydroxyphenyl)-6-hydroxy-2,4-dioxo-1,2,3,4-tetrahydropyrimidine-5-carboxamide (A7)

A mixture of A6 (341 mg, 1.00 mmol) ~1.25 M hydrogen chloride in methanol (10.0 mL, 12.5 mmol), and 1,4-dioxane (10.0 mL) was heated at 60° C. for 18 h in a sealed tube. After this time, the reaction mixture was cooled to rt, filtered, the collected solid washed with methanol (3×15 mL), and dried under reduced pressure (45° C.) to afford A7 (251 mg, 84%) as a light yellow solid: mp>250° C.; $^1$H NMR (500 MHz, DMSO-$d_6$) δ 12.04 (br s, 2H), 11.35 (s, 1H), 10.18 (s, 1H), 7.30 (m, 2H). ESI MS, m/z 298 [M–H]$^-$.

Example 9

Figure 15:
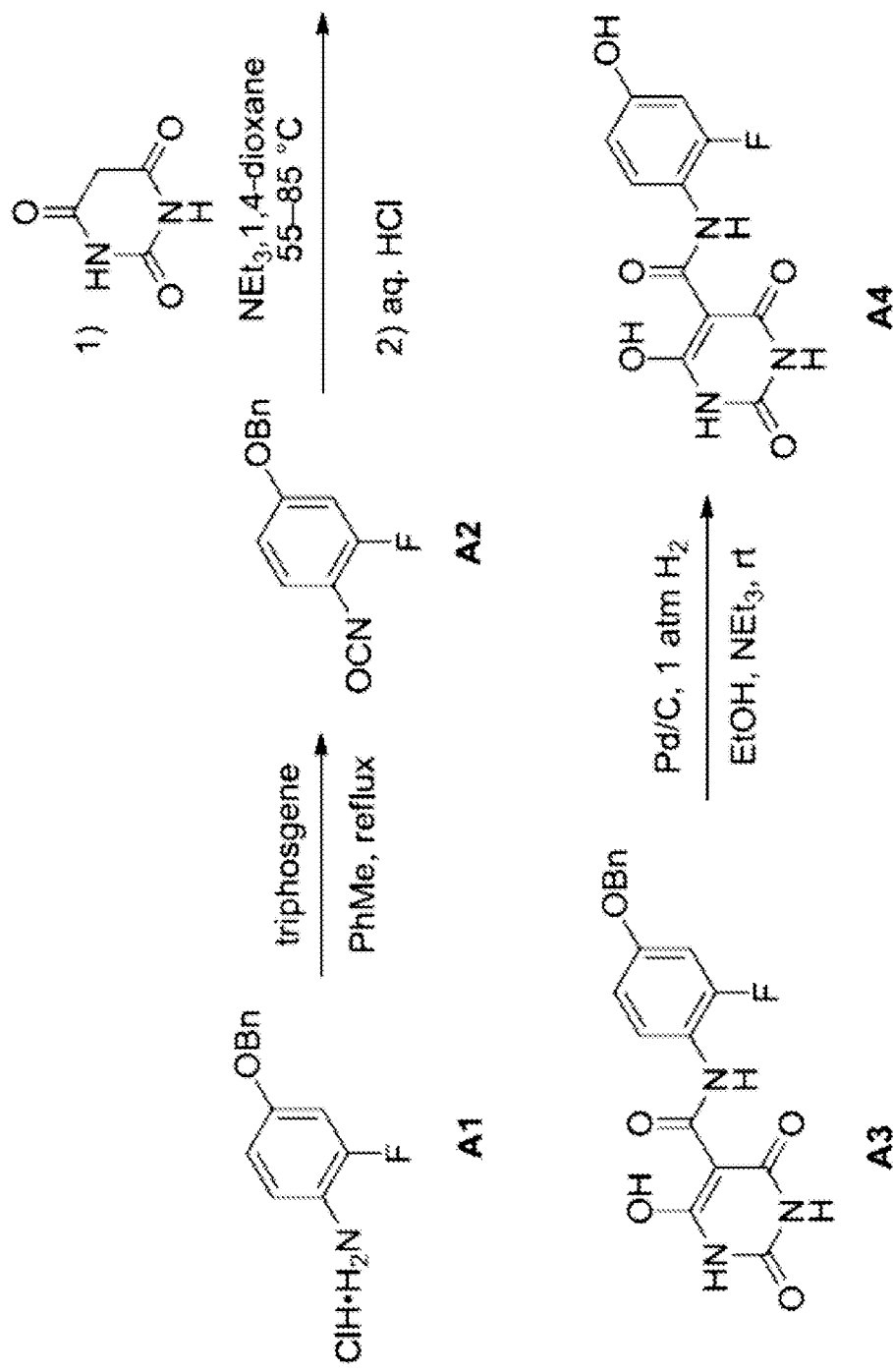
FIG. 15 illustrates synthesis of the compound represented by Formula ($I_i$), described in Example 9.

Preparation of N-(2-fluoro-4-hydroxyphenyl)-6-hydroxy-2,4-dioxo-1,2,3,4-tetrahydropyrimidine-5-carboxamide (Formula ($I_b$), shown as A4 in FIG. 15). The following reaction steps correspond to the steps and compounds shown in FIG. 15.

Step One. 4-(Benzyloxy)-2-fluoro-1-isocyanatobenzene (A2)

A suspension of 4-(benzyloxy)-2-fluoroaniline hydrochloride (A1, 710 mg, 2.80 mmol) and triphosgene (830 mg, 2.80 mmol) in toluene (12 mL) was heated at reflux for 4 h. After this time, the reaction mixture was cooled to room temperature and filtered through a short pad of silica. The filtrate was concentrated under reduced pressure to afford compound A2 (640 mg, 94%) as a white solid: $^1$H NMR (500 MHz, CDCl$_3$) δ 7.41-7.32 (m, 5H), 6.97 (t, J=8.9 Hz, 1H), 6.77 (dd, J=11.4, 2.8 Hz, 1H), 6.68 (d, J=8.9 Hz, 1H), 5.03 (s, 2H).

Step Two. N-(4-(benzyloxy)-2-fluorophenyl)-6-hydroxy-2,4-dioxo-1,2,3,4-tetrahydropyrimidine-5-carboxamide (A3)

To a suspension of pyrimidine-2,4,6(1H,3H,5H)-trione (334 mg, 2.61 mmol) in 1,4-dioxane (15 mL) was added triethylamine (0.36 mL, 2.61) dropwise at 55° C. After 10 min a solution of compound A2 (635 mg, 2.61 mmol) in 1,4-dioxane (5 mL) was added dropwise. The mixture was warmed to 85° C. and stirred for 4 h. After this time the mixture was slowly poured into 0.1 N aqueous hydrochloric acid (75 mL) and stirred for 10 min. The resulting solid was collected by filtration, washed with water, and dried under reduced pressure to afford compound A3 (785 mg, 81%) as an off-white solid: $^1$H NMR (500 MHz, DMSO-$d_6$) δ 12.05 (br s, 1H), 11.42 (s, 2H), 7.90-7.81 (m, 1H), 7.50-7.31 (m, 5H), 7.11-6.99 (m, 1H), 6.92-6.81 (m, 1H), 5.13 (s, 2H). ESI MS (M–H) 370.

Step Three. N-(2-fluoro-4-hydroxyphenyl)-6-hydroxy-2,4-dioxo-1,2,3,4-tetrahydropyrimidine-5-carboxamide (A4)

A mixture of compound A3 (600 mg, 1.62 mmol) and 10% palladium on carbon (300 mg) in ethanol (50 mL) and triethylamine (0.67 mL) was stirred under 1 atmosphere of hydrogen for 18 h. After this time, the reaction mixture was filtered and the initial filtrate discarded. The filter was then rinsed with a mixture of methylene chloride (10 mL), dimethyl sulfoxide (10 mL), and methanol (10 mL). The second filtrate was slowly poured into 0.1 N aqueous hydrochloric acid (100 mL) and stirred for 10 min. The resulting solid was collected by filtration, washed with 0.1 N aqueous hydrochloric acid, and dried under reduced pressure to afford A4 (265 mg, 58%) as light gray solid: mp>250° C.; $^1$H NMR (500 MHz, DMSO-$d_6$) δ 12.03 (br s, 1H), 11.33 (s, 2H), 9.98 (s, 1H), 7.66 (t, J=9.1 Hz, 1H), 6.72 (d, J=2.4 Hz, 1H), 6.70 (d, J=2.4 Hz, 1H). ESI MS, m/z 280 [M–H]$^-$.

Example 10

Figure 16:
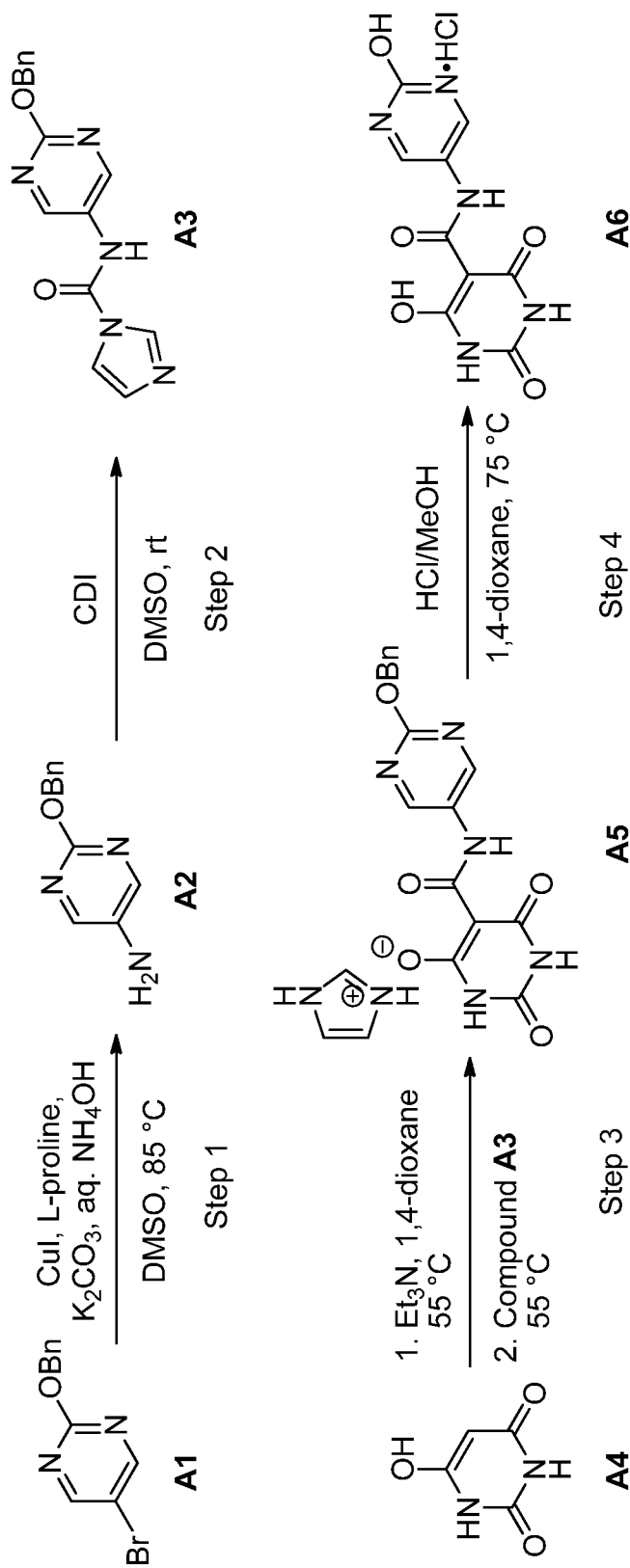
FIG. 16 illustrates synthesis of the compound represented by Formula ($I_f$), described in Example 10.

Preparation of 6-hydroxy-N-(2-hydroxypyrimidin-5-yl)-2,4-dioxo-1,2,3,4-tetrahydropyrimidine-5-carboxamide hydrochloride (Formula ($I_f$), shown as A6 in FIG. 16). The following reaction steps correspond to the steps and compounds shown in FIG. 16.

Step One. 2-(Benzyloxy)pyrimidin-5-amine (A2)

2-(Benzyloxy)-5-bromopyrimidine A1, (265 mg, 1.00 mmol), copper iodide (38 mg, 0.20 mmol), L-proline (46 mg, 0.40 mmol), and potassium carbonate (207 mg, 1.50 mmol) were combined in a sealed tube. The vessel was evacuated and backfilled with dry nitrogen before the addition of dimethylsulfoxide (1.0 mL). After 5 minutes of stirring, concentrated ammonium hydroxide (0.10 mL, 1.5 mmol) was added and the mixture heated at 85° C. for 18 h. After this time, the mixture was cooled, diluted with water (10 mL), and ethyl acetate (10 mL). The ethyl acetate was dried over sodium sulfate, the drying agent was removed by filtration, and the resulting solution was concentrated under reduced pressure. The residue obtained was purified by chromatography (silica, 25-100% ethyl acetate/hexanes) to afford compound A2 (120 mg, 60%) as a tan solid: $^1$H NMR (500 MHz, CDCl$_3$) δ 8.04 (s, 2H), 7.46 (d, J=7.1 Hz, 2H), 7.36-7.26 (m, 3H), 5.36 (s, 2H), 3.40 (br s, 2H).

Step Two. N-(2-(benzyloxy)pyrimidin-5-yl)-1H-imidazole-1-carboxamide (A3)

1,1'-Carbonyldiimidazole (186 mg, 1.15 mmol) was added in one portion to a solution of compound A2, (201 mg, 1.00 mmol) in sieve-dried dimethyl sulfoxide (0.5 mL) and stirred at ambient temperature for 2 h. The resulting stock solution of compound A3 was used for subsequent reaction without purification or characterization.

Step Three. 1H-imidazol-3-ium 5-((2-(benzyloxy)pyrimidin-5-yl)carbamoyl)-2,6-dioxo-1,2,3,6-tetrahydropyrimidin-4-olate (A5)

To a stirred suspension of barbituric acid A4 (128 mg, 1.00 mmol) in 1,4-dioxane (1.5 mL) was added triethylamine (0.14 mL, 1.0 mmol) dropwise at 55° C. After 10 min the stock solution of compound A3 (1.00 mmol) was added dropwise. The mixture was stirred and heated at 55° C. for an additional 45 min. After this time, the reaction mixture was cooled, diluted with 1,4-dioxane (10 mL), and the resulting solid collected by filtration. The solid was washed with 1,4-dioxane (4×10 mL), methanol (2×10 mL), and dried under reduced pressure to afford A5 (234 mg, 55%) as a white solid: $^1$H NMR (500 MHz, DMSO-$d_6$) δ 13.50-11.00 (br s, 2H), 11.81 (s, 1H), 8.77 (s, 2H), 8.62 (s, 1H), 7.47-7.31 (m, 7H), 5.35 (s, 2H).

Step Four. 6-Hydroxy-N-(2-hydroxypyrimidin-5-yl)-2,4-dioxo-1,2,3,4-tetrahydropyrimidine-5-carboxamide hydrochloride (A6)

A suspension of A5 (95 mg, 0.22 mmol) in ~1.25 M hydrogen chloride in methanol (3.0 mL) and 1,4-dioxane (1.0 mL) was stirred and heated at 75° C. for 16 h. After this time, the hot mixture was filtered, the collected solid washed with methanol (3×5 mL), and dried under reduced pressure (45° C.) to afford A6 (45 mg, 56%) as a light pink solid: $^1$H NMR (500 MHz, DMSO-d$_6$) δ 12.50-11.00 (br s, 3H), 10.88 (s, 1H), 8.50 (s, 2H); APCI MS, m/z 264 [M−H]$^−$; mp>250° C.

Example 11

Figure 17:
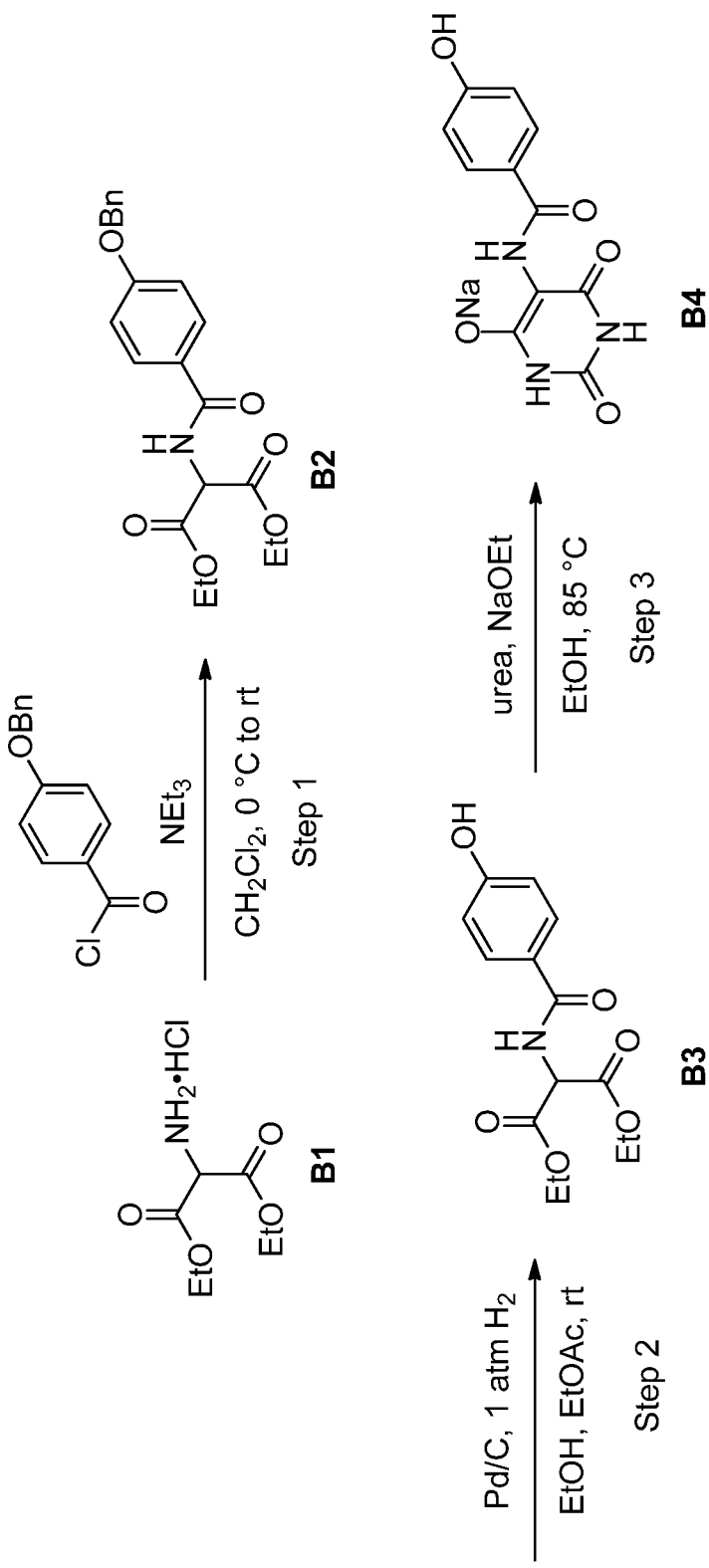
FIG. 17 illustrates synthesis of the compound represented by Formula ($I_l$), described in Example 11.

Preparation of sodium 5-(4-hydroxybenzamido)-2,6-dioxo-1,2,3,6-tetrahydropyrimidin-4-olate (Formula (I$_i$), shown as (B4) in FIG. 17. The following reaction steps correspond to the steps and compounds shown in FIG. 17.

Step One. Diethyl 2-(4-(benzyloxy)benzamido)malonate (B2)

To a stirred, ice-cooled mixture of diethyl 2-aminomalonate hydrochloride (212 mg, 1.00 mmol), triethylamine (0.16 mL, 1.2 mmol), and dichloromethane (5 mL) was added 4-(benzyloxy)benzoyl chloride (272 mg, 1.10 mmol) in dichloromethane (5 mL) over 5 min. The reaction was allowed to warm to ambient temperature and stirred for 18 h. After this time, the reaction mixture was diluted with methanol (1 mL) and adsorbed on silica (~10 mL). The crude material was purified by chromatography (silica, 0-50% ethyl acetate/hexanes) to afford B2 (314 mg, 82%) as a white solid: $^1$H NMR (500 MHz, CDCl3) δ 7.81 (d, J=9.8 Hz, 2H), 7.45-7.30 (m, 5H), 7.03-6.98 (m, 3H), 5.32 (d, J=6.8 Hz, 1H), 5.12 (s, 2H), 4.35-4.25 (m, 4H), 1.32 (t, J=7.1 Hz, 6H).

Step Two. Diethyl 2-(4-hydroxybenzamido)malonate (B3)

A mixture of B2 (725 mg, 1.88 mmol), 10% palladium on carbon (200 mg), ethanol (35 mL), and ethyl acetate (35 mL) was stirred under 1 atmosphere of hydrogen at ambient temperature for 2 d. After this time, the reaction mixture was filtered and concentrated under reduced pressure. The residue obtained was purified by chromatography (silica, 0-100% ethyl acetate/hexanes) to afford compound B3 (150 mg, 27%) as a colorless oil: $^1$H NMR (500 MHz, CDCl3) δ 7.82 (br s, 1H), 7.69 (d, J=6.9 Hz, 2H), 7.14 (d, J=6.6 Hz, 1H), 6.86 (d, J=6.9 Hz, 2H), 5.32 (d, J=6.6 Hz, 1H), 4.36-4.25 (m, 4H), 1.31 (t, J=7.2 Hz, 6H).

Step Three. Sodium 5-(4-hydroxybenzamido)-2,6-dioxo-1,2,3,6-tetrahydropyrimidin-4-olate (B4)

A mixture of B3 (150 mg, 0.510 mmol), urea (153 mg, 2.55 mmol), 21% sodium ethoxide in ethanol (0.50 mL, 1.5 mmol), and ethanol (3 mL) was stirred and heated at 85° C. for 4 h. After this time, the hot reaction mixture was filtered, the collected solid washed with ethanol (2×5 mL), dried under reduced pressure, redissolved in water (2 mL), and lyophilized to afford compound B4 (95 mg, 66%) as an off-white solid: $^1$H NMR (500 MHz, D$_2$O) δ 7.49 (d, J=8.7 Hz, 2H), 6.50 (d, J=8.8 Hz, 2H); APCI MS, m/z 262 [M−H]$^−$; mp>250° C.

Example 12

Figure 18:
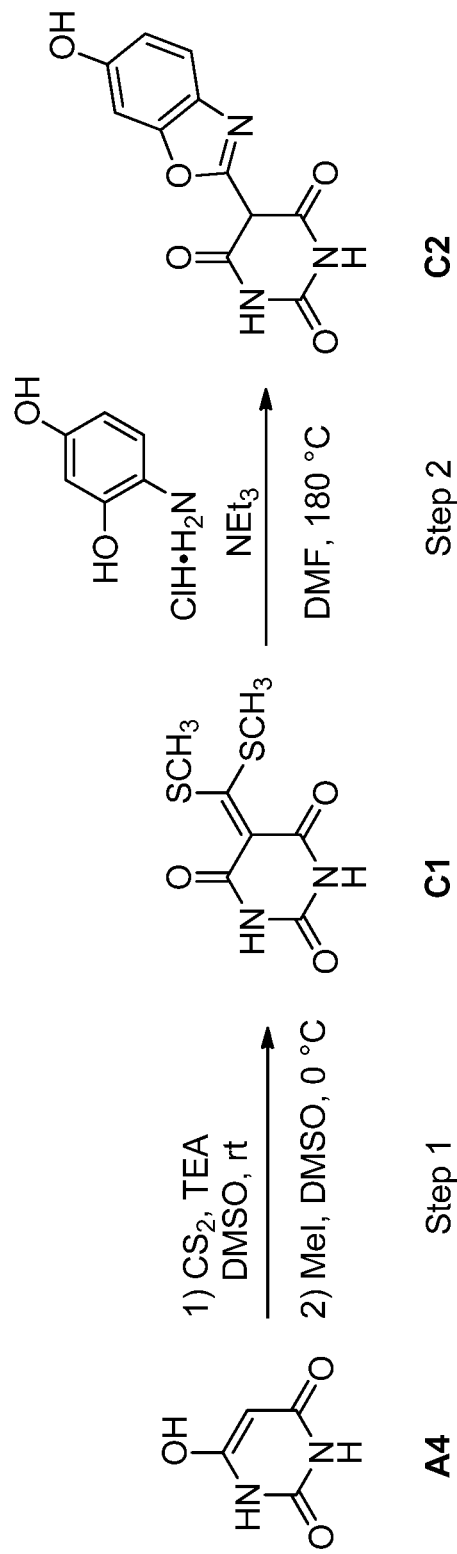
FIG. 18 illustrates synthesis of the compound represented by Formula ($I_j$), described in Example 12.

Preparation of 5-(6-hydroxybenzo[d]oxazol-2-yl)pyrimidine-2,4,6(1H,3H,5H)-trione (Formula (I$_j$) shown as (C2) in FIG. 18). The following reaction steps correspond to the steps and compounds shown in FIG. 18.

Step One. 5-(Bis(methylthio)methylene)pyrimidine-2,4,6(1H,3H,5H)-trione (C1)

A mixture of barbituric acid A4 (3.90 g, 30.0 mmol), triethylamine (8.4 mL, 60 mmol), and carbon disulfide (1.8 mL, 30 mmol) was stirred at ambient temperature for 1 h. The mixture was then cooled in an ice water bath and methyl iodide (3.7 mL, 60 mmol) added in one portion. After removal of the ice bath the mixture was stirred for an additional 3 h. After this time, the mixture was poured into cold water (200 mL) with rapid stirring and then left undisturbed for 1 d. The mixture was then filtered, the collected solid washed with water (3×125 mL), and dried under reduced pressure. The crude product was recrystallized from hot dimethylformamide to afford C1 (467 mg, 7%) as a light yellow solid: $^1$H NMR (500 MHz, DMSO-d$_6$) δ 10.89 (s, 2H), 2.54 (s, 6H).

Step Two. 5-(6-Hydroxybenzo[d]oxazol-2-yl)pyrimidine-2,4,6(1H,3H,5H)-trione (C2)

A mixture of compound C1 (260 mg, 1.12 mmol), 4-aminobenzene-1,3-diol hydrochloride (182 mg, 1.12 mmol), triethylamine (0.17 mL, 1.2 mmol), and dimethylformamide (4 mL) in a sealed microwave process vial (20 mL, Biotage) was stirred and heated at 180° C. for 3 h in a microwave reactor (Biotage). After this time, the cooled reaction mixture was filtered, the collected solid triturated with hot dimethyl formamide (3×10 mL) followed by methanol (3×10 mL), and dried under reduced pressure to afford C2 (273 mg, 93%) as a light purple-red solid: $^1$H NMR (500 MHz, DMSO-d$_6$) δ 13.18 (br s, 1H), 10.53 (s, 2H), 9.92 (s, 1H), 7.44 (d, J=8.6 Hz, 1H), 7.09 (d, J=2.0 Hz, 1H), 6.84 (dd, J=8.6, 2.1 Hz, 1H); ESI MS, m/z 260 [M−H]$^−$; mp>250° C.

Example 13

Figure 19:
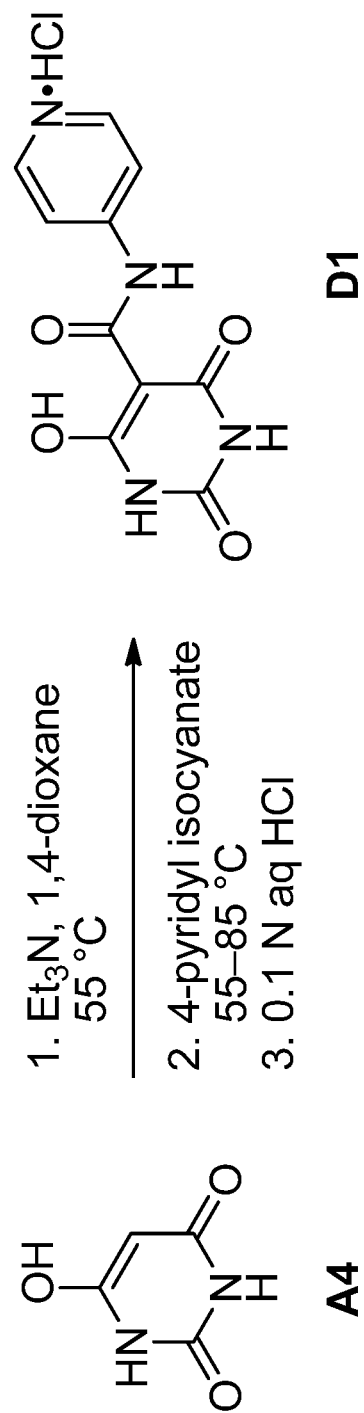
FIG. 19 illustrates synthesis of the compound represented by Formula ($I_k$), described in Example 13.

Preparation of 6-hydroxy-2,4-dioxo-N-(pyridin-4-yl)-1,2,3,4-tetrahydropyrimidine-5-carboxamide hydrochloride (Formula (I$_k$), shown as (D1) in FIG. 19). The following reaction steps correspond to the steps and compounds shown in FIG. 19. To a stirred suspension of barbituric acid A4 (965 mg, 7.53 mmol) in 1,4-dioxane (50 mL) was added triethylamine (1.06 mL, 77.7 mml) drop wise at 55° C. After 10 min 4-pyridyl isocyanate (905 mg, 7.53 mmol) was added in one portion, the mixture heated at 55° C. for 1 h, and then heated for 3 h at 85° C. After this time, the hot reaction mixture was poured into a stirred solution of aqueous 0.1M hydrochloric acid (180 mL), filtered, the collected solid washed with additional 0.1M hydrochloric acid (2×50 mL), washed with ethanol (1×50 mL), and dried under reduced pressure to afford D1 (1.38 g, 65%) as a light brown solid: $^1$H NMR (500 MHz, TFA-d) δ 8.62 (d, J=6.9 Hz, 2H), 8.34 (d, J=7.0 Hz, 2H); APCI MS, m/z 247 [M−H]$^−$; mp>250° C.

Example 14

Figure 20:
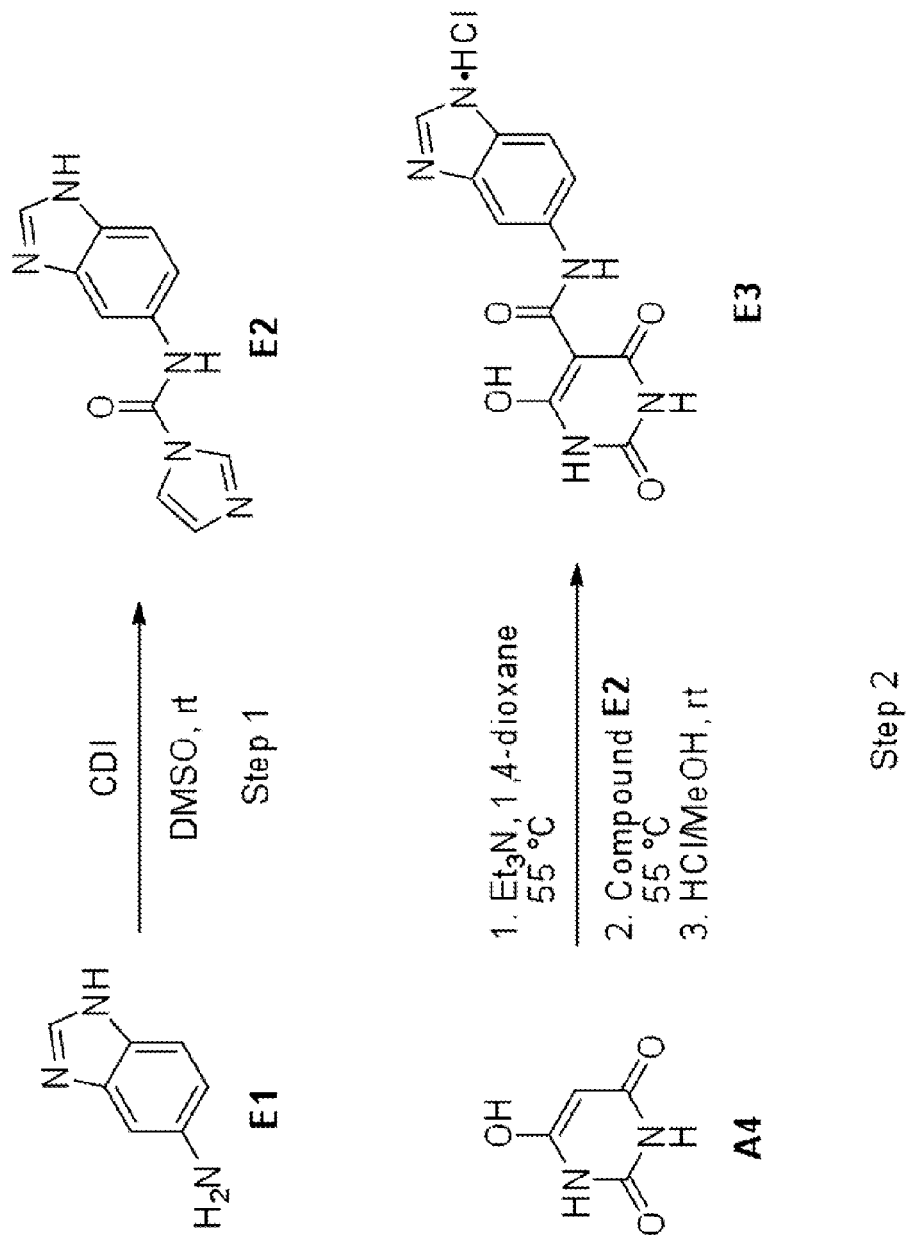
FIG. 20 illustrates synthesis of the compound represented by Formula ($I_o$), described in Example 14.

Preparation of N-(1H-benzo[d]imidazol-6-yl)-6-hydroxy-2,4-dioxo-1,2,3,4-tetrahydropyrimidine-5-carboxamide hydrochloride (Formula I($_o$), shown as (E3) in FIG. 20). The following reaction steps correspond to the steps and compounds shown in FIG. 20.

Step One. N-(1H-benzo[d]imidazol-6-yl)-1H-imidazole-1-carboxamide (E2)

Compound E2 was prepared following the procedure of Example 10, Step 2 from compound E1 (1.29 g, 9.70 mmol) and 1,1'-carbonyldiimidazole (1.83 g, 11.30 mmol) in sieve-dried dimethyl sulfoxide (10 mL) to afford a stock solution of compound E2 for subsequent reaction without purification or characterization.

Step Two. N-(1H-benzo[d]imidazol-6-yl)-6-hydroxy-2,4-dioxo-1,2,3,4-tetrahydropyrimidine-5-carboxamide hydrochloride (E3)

To a stirred suspension of barbituric acid A4 (1.24 g, 9.68 mmol) in 1,4-dioxane (15 mL) was added triethylamine (1.3 mL, 9.7 mmol) drop wise at 55° C. After 10 min the stock solution of compound E2 (9.70 mmol) was added drop wise, the mixture heated at 55° C. for 0.5 h, and then heated for 2 h at 85° C. After this time, the reaction mixture was cooled to ambient temperature and the resulting solid collected by filtration. The solid was then washed with 1,4-dioxane (3×30 mL), methanol (2×30 mL), and dried under reduced pressure to afford crude E3 (2.15 g) as an off-white solid. A suspension of crude E3 (774 mg) in ~1.25 M hydrogen chloride in methanol (15 mL) was stirred at ambient temperature for 18 h. After this time, the resulting solid was collected by filtration, washed with methanol (3×25 mL), and dried under reduced pressure to afford E3 (635 mg, 56% yield calculated based on fraction (774 mg/2150 mg) of crude treated with HCl/MeOH) as a white solid: $^1$H NMR (500 MHz, TFA-d) δ 9.25 (s, 1H), 8.31 (s, 1H), 7.97 (d, J=9.0 Hz, 1H), 7.78 (dd, J=9.0, 1.6 Hz, 1H); ESI MS, m/z 288 [M+H]$^+$.

Example 15

Figure 21:
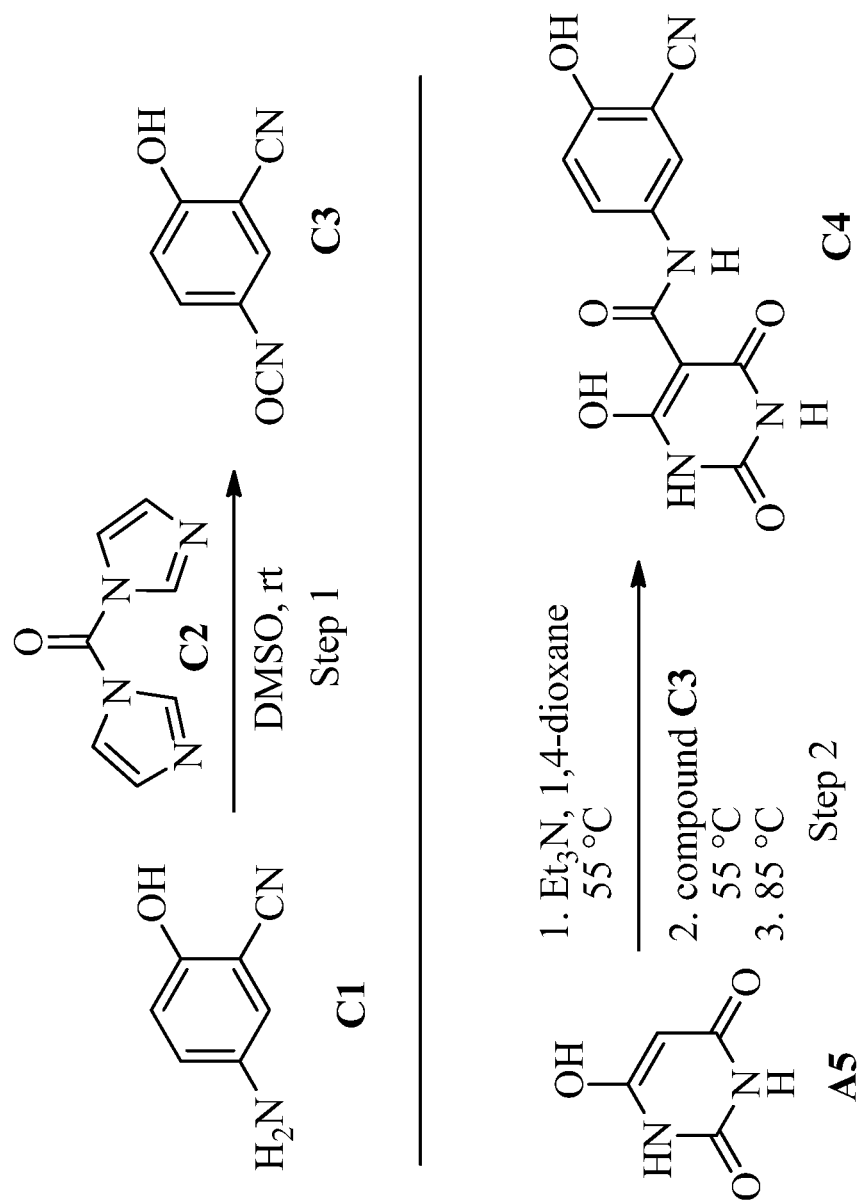
FIG. 21 illustrates synthesis of the compound represented by Formula ($II_d$), described in Example 15.

Preparation of N-(3-cyano-4-hydroxyphenyl)-6-hydroxy-2,4-dioxo-1,2,3,4-tetrahydropyrimidine-5-carboxamide (Formula IId, shown as (C4) in FIG. 21). The following reaction steps correspond to the steps and compounds shown in FIG. 21.

Step One & Two. N-(3-Cyano-4-hydroxyphenyl)-6-hydroxy-2,4-dioxo-1,2,3,4-tetrahydropyrimidine-5-carboxamide (C4)

To a stirred solution of compound C2 (0.181 g, 1.12 mmol) in anhydrous DMSO (4 mL) was added compound C1 (0.100 g, 0.745 mmol) at ambient temperature under nitrogen. The reaction mixture was then stirred for 30 min to provide a solution of compound C3 in DMSO which was used directly in the subsequent step.

In a separate flask, to a suspension of barbituric acid A5 (0.095 g, 0.745 mmol) in anhydrous 1,4-dioxane (4 mL) was added triethylamine (0.075 g, 0.745 mmol) at 55° C. under nitrogen. After the addition was completed, the mixture was stirred for 5 min. Then, to this mixture was added the compound C3 solution in DMSO. The resulting mixture was heated to 85° C. for 2 h. After cooling to ambient temperature, 0.5 N hydrochloric acid (20 mL) was added slowly. The mixture was stirred for 20 min and filtered. The filter cake was washed with 0.5 N hydrochloric acid (2×10 mL) and water (2×10 mL) and dried in vacuo to afford a crude product (0.169 g) which was further purified by recrystallization from DMSO and water to afford compound C4 (0.112 g, 52%) as an off-white solid: $^1$H NMR (300 MHz, DMSO-d$_6$) δ 12.05 (br s, 1H), 11.40 (br s, 1H), 11.32 (s, 1H), 11.20 (s, 1H), 7.81 (d, J=2.7 Hz, 1H), 7.59 (dd, J=9.0, 2.7 Hz, 1H), 7.03 (d, J=9.0 Hz, 1H); ESI MS m/z 287 [M−H]$^−$.

Example 16

Figure 22:
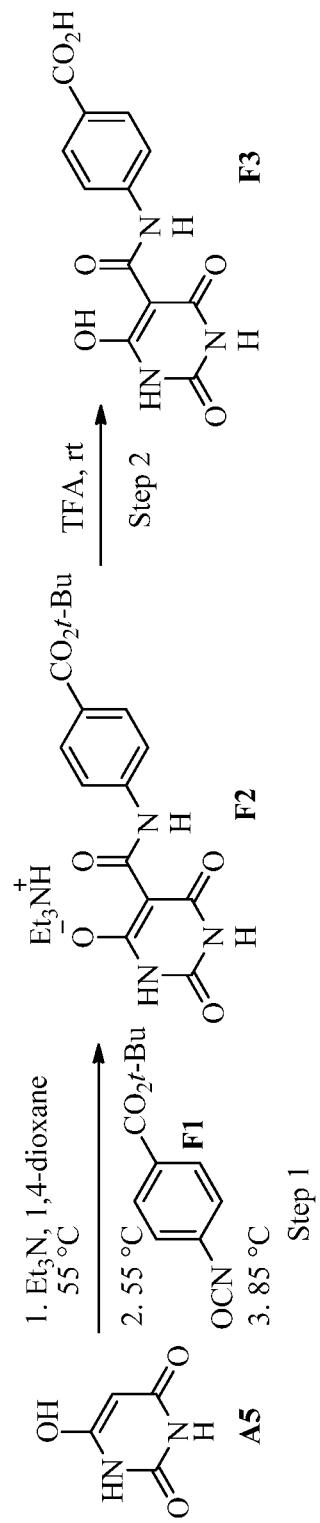
FIG. 22 illustrates synthesis of the compound represented by Formula ($II_e$), described in Example 16.

Preparation of 4-(6-hydroxy-2,4-dioxo-1,2,3,4-tetrahydropyrimidine-5-carboxamido)benzoic acid (Formula IIe, shown as F3 in FIG. 22). The following reaction steps correspond to the steps and compounds shown in FIG. 22.

Step One. tert-Butyl 4-(6-Hydroxy-2,4-dioxo-1,2,3,4-tetrahydropyrimidine-5-carboxamido)benzoate Triethylamine Salt (F2)

To a suspension of barbituric acid A5 (0.278 g, 2.17 mmol) in anhydrous 1,4-dioxane (5 mL) was added triethylamine (0.219 g, 2.17 mmol) at 55° C. under nitrogen. After the addition was completed, the mixture was stirred for 15 min. Then, to this mixture was added a solution of compound F1 (0.475 g, 2.17 mmol) in anhydrous 1,4-dioxane (2 mL), and the resulting mixture was heated to 85° C. for 4 h. After this time, the hot reaction mixture was filtered. The filter cake was washed with 1,4-dioxane (5×15 mL) and dried in vacuo to afford compound F2 (0.780 g, 80%) as a white solid: $^1$H NMR (300 MHz, DMSO-d$_6$) δ 12.40 (s, 1H), 9.71 (s, 1H), 9.40-8.90 (br s, 2H), 7.77 (d, J=8.7 Hz, 2H), 7.60 (d, J=8.7 Hz, 2H), 3.09 (q, J=7.2 Hz, 6H), 1.53 (s, 9H), 1.17 (t, J=7.2 Hz, 9H).

Step Two. 4-(6-Hydroxy-2,4-dioxo-1,2,3,4-tetrahydropyrimidine-5-carboxamido)benzoic Acid (F3)

A suspension of compound F2 (0.448 g, 1.00 mmol) in TFA (5 mL) was stirred at ambient temperature for 4 h. After this time, the mixture was diluted with dichloromethane (5 mL) and filtered. The filter cake was washed with methanol (2×10 mL) and water (2×10 mL), and dried under high vacuum at 45° C. to afford compound F3 (0.217 g, 75%) as a white solid: $^1$H NMR (300 MHz, DMSO-d$_6$) δ 13.20-12.80 (br s, 1H), 12.50-11.30 (br s, 2H), 11.73 (s, 1H), 7.96 (d, J=8.7 Hz, 2H), 7.67 (d, J=8.7 Hz, 2H); APCI MS, m/z 290 [M−H]$^−$.

Example 17

Figure 23:
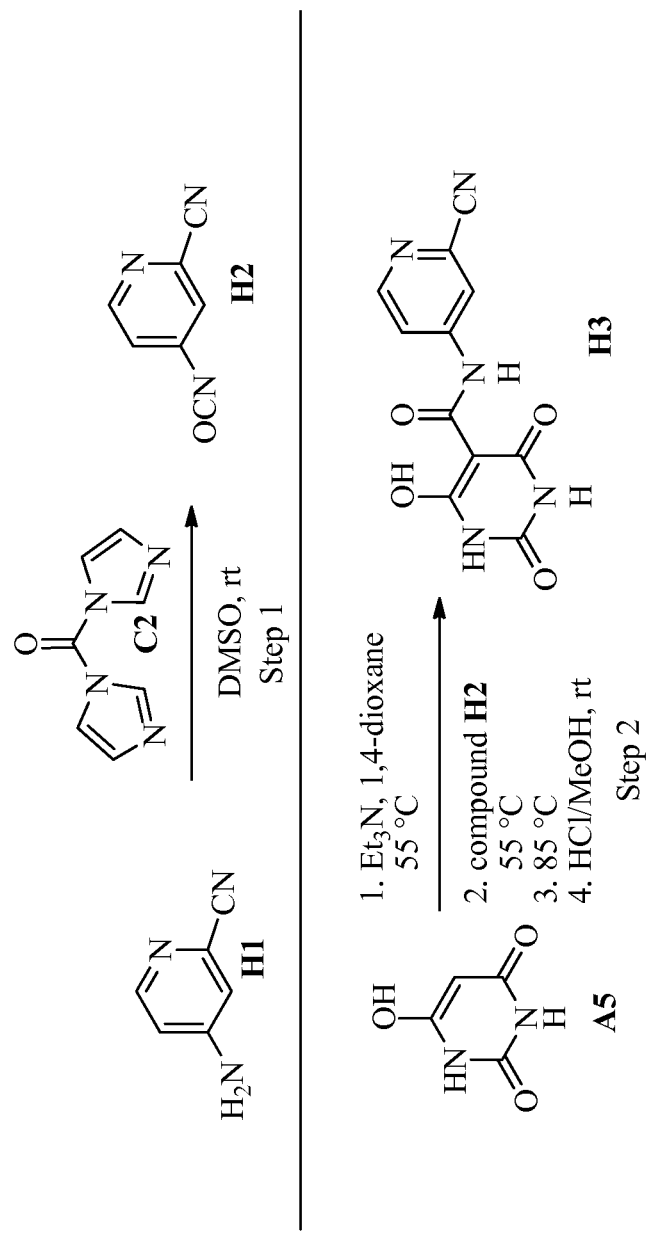
FIG. 23 illustrates synthesis of the compound represented by Formula ($III_b$), described in Example 17.

Preparation of N-(2-cyanopyridin-4-yl)-6-hydroxy-2,4-dioxo-1,2,3,4-tetrahydropyrimidine-5-carboxamide (Formula IIIb, shown as H3 in FIG. 23). The following reaction steps correspond to the steps and compounds shown in FIG. 23.

Step One & Two. N-(2-Cyanopyridin-4-yl)-6-hydroxy-2,4-dioxo-1,2,3,4-tetrahydropyrimidine-5-carboxamide (H3)

To a solution of compound C2 (0.713 g, 4.40 mmol) in anhydrous DMSO (2 mL) was added compound H1 (0.476 g, 4.00 mmol) at ambient temperature under nitrogen. The reaction mixture was then stirred for 1.5 h to provide a solution of compound H2 in DMSO which was used directly in the subsequent step.

In a separate flask, to a suspension of barbituric acid A5 (0.512 g, 4.00 mmol) in anhydrous 1,4-dioxane (20 mL) was added triethylamine (0.404 g, 4.00 mmol) at 55° C. under nitrogen. After the addition was completed, the mixture was stirred for 15 min. Then, to this mixture was added the compound H2 solution in DMSO dropwise over 30 min. The resulting mixture was heated to 85° C. for 3 h. After this time, the hot reaction mixture was filtered. The filter cake was washed with 1,4-dioxane (4×15 mL) and MeOH (3×10 mL), suspended in 1 M hydrogen chloride in methanol (15 mL) and stirred at ambient temperature for 4 h. After this time, the mixture was filtered. The filter cake was suspended in water (5 mL) and stirred at approximately 100° C. for 6 h and the hot mixture was filtered. The filter cake was washed with hot water (6×10 mL) and dried under high vacuum at 45° C. to afford compound H3 (0.160 g, 15%) as a light brown solid: $^1$H NMR (500 MHz, DMSO-$d_6$) δ 11.94 (br s, 2H), 11.86 (s, 1H), 8.64 (d, J=5.6 Hz, 1H), 8.23 (d, J=2.0 Hz, 1H), 7.89 (dd, J=5.6, 2.0 Hz, 1H); ESI MS, m/z 272 [M−H]$^-$.

Example 18

Figure 24:
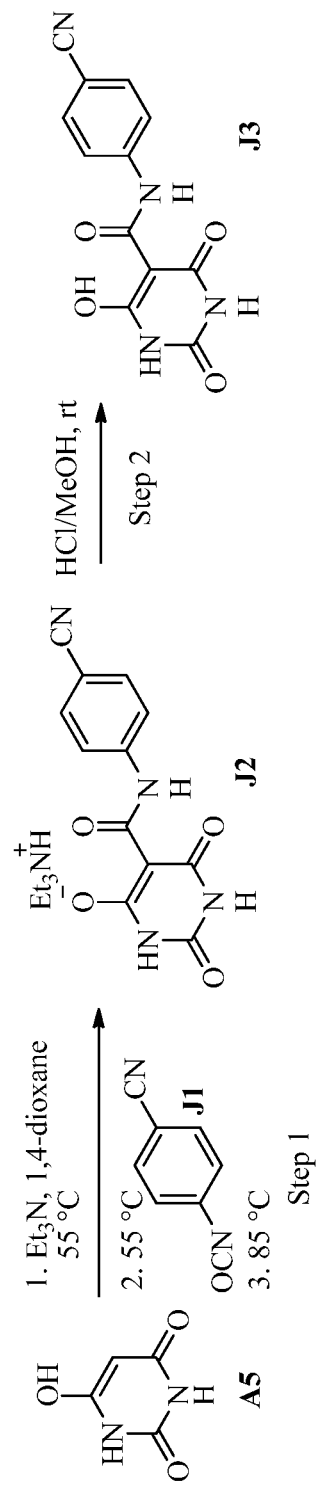
FIG. 24 illustrates synthesis of the compound represented by Formula ($II_c$), described in Example 18.

Preparation of N-(4-cyanophenyl)-6-hydroxy-2,4-dioxo-1,2,3,4-tetrahydropyrimidine-5-carboxamide (Formula IIc, shown as (J3) in FIG. 24). The following reaction steps correspond to the steps and compounds shown in FIG. 24.

Step One. N-(4-Cyanophenyl)-6-hydroxy-2,4-dioxo-1,2,3,4-tetrahydropyrimidine-5-carboxamide Triethylamine Salt (J2)

To a suspension of barbituric acid A5 (1.43 g, 11.2 mmol) in anhydrous 1,4-dioxane (20 mL) was added triethylamine (1.13 g, 11.2 mmol) at 55° C. under nitrogen. After the addition was completed, the mixture was stirred for 30 min. Then, to this mixture was added a solution of compound J1 (1.61 g, 11.2 mmol) in anhydrous 1,4-dioxane (15 mL) dropwise over 10 min. The resulting mixture was heated to 85° C. for 2 h. The hot reaction mixture was filtered. The filter cake was washed with 1,4-dioxane (3×20 mL) and dried in vacuo to afford compound J2 (2.04 g, 49%) as a white solid: $^1$H NMR (300 MHz, DMSO-$d_6$) δ 12.54 (s, 1H), 9.81 (br s, 2H), 9.30 (br s, 1H), 7.67 (br s, 4H), 3.12 (q, J=7.2 Hz, 6H), 1.17 (t, J=7.2 Hz, 9H); ESI MS, m/z 271 [M−H]$^-$.

Step Two. N-(4-Cyanophenyl)-6-hydroxy-2,4-dioxo-1,2,3,4-tetrahydropyrimidine-5-carboxamide (J3)

A suspension of compound J2 (1.00 g, 2.68 mmol) in 1.25 M hydrogen chloride in methanol (20 mL) was stirred at ambient temperature for 8 h. After this time, the reaction mixture was filtered, the filter cake washed with methanol (3×10 mL) and dried under high vacuum at 45° C. to afford compound J3 (0.670 g, 92%) as an off-white solid: $^1$H NMR (300 MHz, DMSO-$d_6$) δ 12.20-11.60 (br s, 2H), 11.75 (s, 1H), 7.86 (d, J=8.7 Hz, 2H), 7.75 (d, J=8.7 Hz, 2H); ESI MS, m/z 271 [M−H]$^-$.

Example 19

Figure 25:
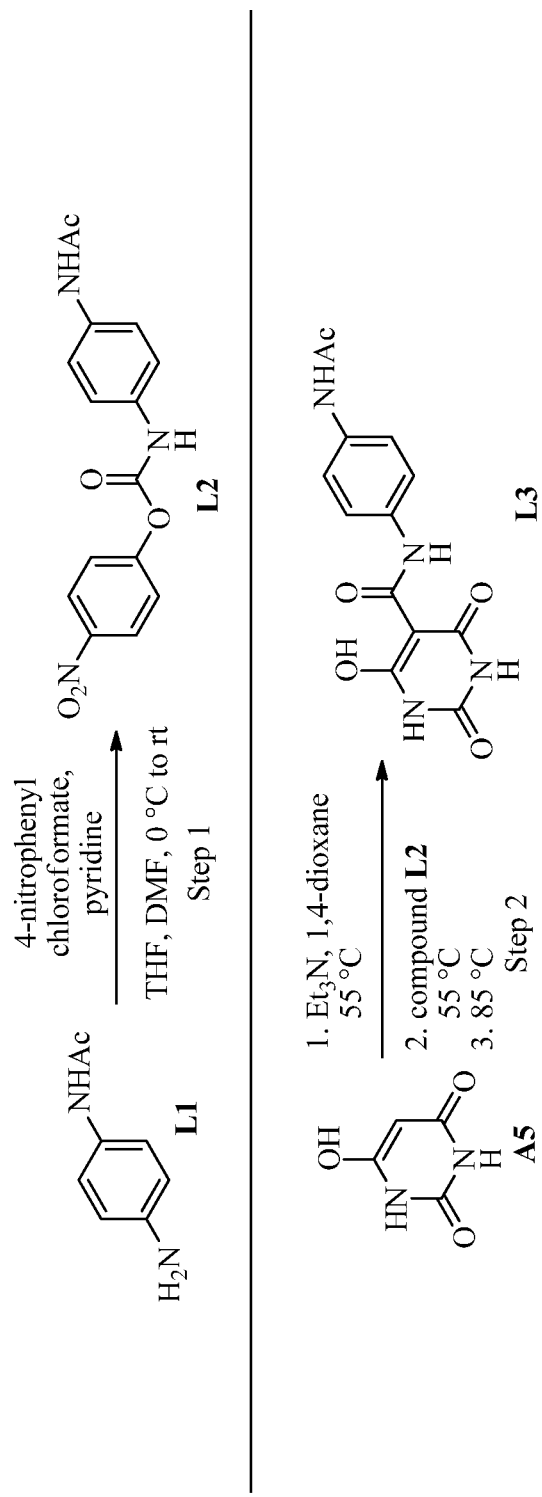
FIG. 25 illustrates synthesis of the compound represented by Formula ($II_a$), described in Example 19.

Preparation of N-(4-acetamidophenyl)-6-hydroxy-2,4-dioxo-1,2,3,4-tetrahydropyrimidine-5-carboxamide (Formula IIa, shown as (L3) in FIG. 25). The following reaction steps correspond to the steps and compounds shown in FIG. 25.

Step One & Two. N-(4-Acetamidophenyl)-6-hydroxy-2,4-dioxo-1,2,3,4-tetrahydropyrimidine-5-carboxamide (L3)

To a stirred solution of 4-nitrophenyl chloroformate (2.01 g, 10.0 mmol) in anhydrous THF (25 mL) was added a solution of compound L1 (1.50 g, 10.0 mmol) and pyridine (0.791 g, 10.0 mmol) in anhydrous THF (20 mL) and anhydrous DMF (15 mL) dropwise over 20 min at 0° C. under nitrogen. After the addition was completed, the reaction was slowly warmed to ambient temperature over 2 h and stirred at ambient temperature for 18 h to provide a solution of compound L2 in THF and DMF which was used directly in the subsequent step.

In a separate flask, to a suspension of barbituric acid A5 (1.28 g, 10.0 mmol) in anhydrous 1,4-dioxane (25 mL) was added triethylamine (2.02 g, 20.0 mmol) at 55° C. under nitrogen. After the addition was completed, the mixture was stirred for 10 min. Then, to this mixture was added the compound L2 solution in THF and DMF dropwise over 25 min. The resulting mixture was heated to 85° C. for 5 h. After cooling to ambient temperature, 0.1 N hydrochloric acid (600 mL) was added. The mixture was stirred for 25 min and filtered. The filter cake was washed with 1,4-dioxane (2×40 mL), then added to 0.1 N NaOH aqueous solution (500 mL), stirred at 40° C. for 30 min, and filtered. The filtrate was acidified with 1 N hydrochloric acid to pH 2. The resulting solid was collected by vacuum filtration, washed with water (3×30 mL), and dried under high vacuum at 50° C. to afford compound L3 (2.39 g, 79%) as a white solid: $^1$H NMR (300 MHz, DMSO-$d_6$) δ 12.30-11.60 (br s, 2H), 11.45 (s, 1H), 10.01 (s, 1H), 7.60 (d, J=8.7 Hz, 2H), 7.45 (d, J=8.7 Hz, 2H), 2.04 (s, 3H); APCI MS, m/z 305 [M+H]$^+$.

Example 20

Figure 26:
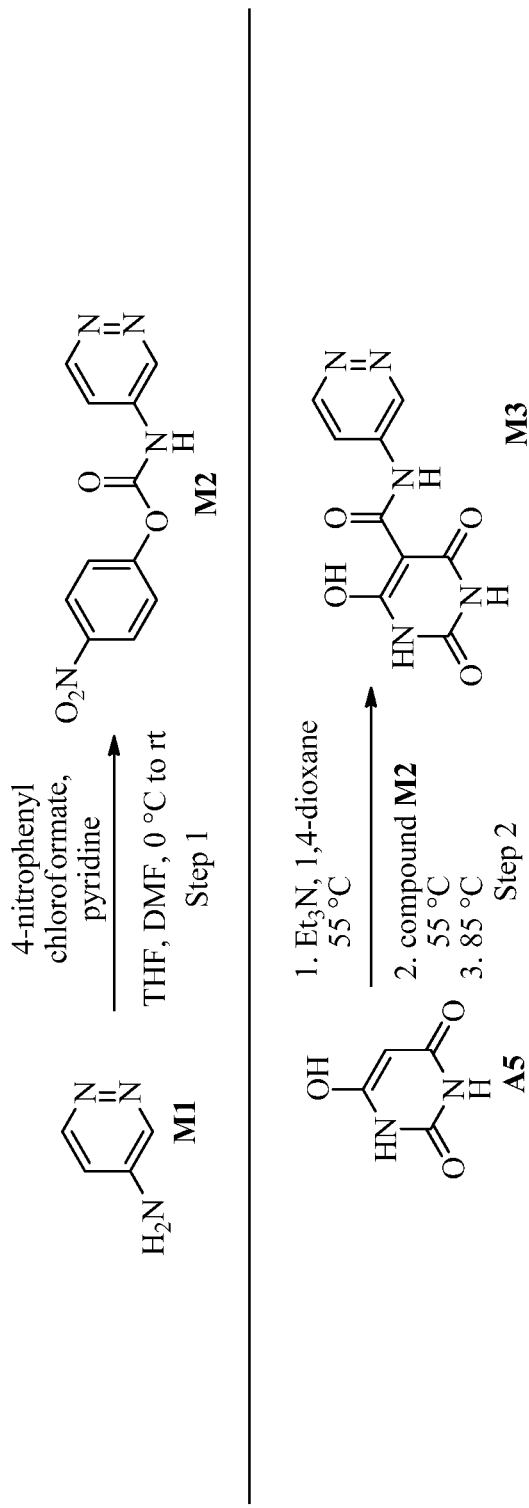
FIG. 26 illustrates synthesis of the compound represented by Formula (III$_a$), described in Example 20.

Preparation of 6-hydroxy-2,4-dioxo-N-(pyridazin-4-yl)-1,2,3,4-tetrahydropyrimidine-5-carboxamide (Formula Ma, shown as (M3) in FIG. 26). The following reaction steps correspond to the steps and compounds shown in FIG. 26.

Step One & Two. 6-Hydroxy-2,4-dioxo-N-(pyridazin-4-yl)-1,2,3,4-tetrahydropyrimidine-5-carboxamide (M3)

To a stirred solution of 4-nitrophenyl chloroformate (2.12 g, 10.5 mmol) in anhydrous THF (20 mL) was added a solution of compound M1 (1.00 g, 10.5 mmol) and pyridine (1.08 g, 13.7 mmol) in anhydrous THF (20 mL) and anhydrous DMF (5 mL) dropwise over 10 min at 0° C. under nitrogen. After the addition was completed, the reaction mixture was slowly warmed to ambient temperature over 2 h and stirred at ambient temperature for 18 h to provide a solution of compound M2 in THF and DMF which was used directly in the subsequent step.

In a separate flask, to a suspension of barbituric acid A5 (1.35 g, 10.5 mmol) in anhydrous 1,4-dioxane (40 mL) was added triethylamine (2.14 g, 21.1 mmol) at 55° C. under nitrogen. After addition was completed, the mixture was stirred for 10 min. Then, to this mixture was added the compound M2 solution in THF and DMF dropwise over 25 min. The resulting mixture was heated to 85° C. for 5 h. After cooling to ambient temperature, 0.1 N hydrochloric acid (600 mL) was added. The mixture was stirred for 25 min and filtered. The filter cake was washed with water (2×30 mL), then dissolved in 1 N NaOH aqueous solution (150 mL) and purified by C18 column chromatography eluting with 10% methanol/water to provide a solution of the pure sodium salt of compound M3. The solution of purified sodium salt of M3 was acidified with 0.1 N hydrochloride acid to pH<2. The resulting solid was filtered. The filter cake was washed with water (3×30 mL) and dried under high vacuum at 50° C. to afford compound M3 (0.236 g, 9%) as a brown solid: $^1$H NMR (300 MHz, CF$_3$CO$_2$D) δ 9.64 (d, J=2.7 Hz, 1H), 9.33 (d, J=6.9 Hz, 1H), 8.97 (dd, J=6.9, 3.0 Hz, 1H); ESI MS, m/z 250 [M+H]$^+$.

Example 21

Figure 27:
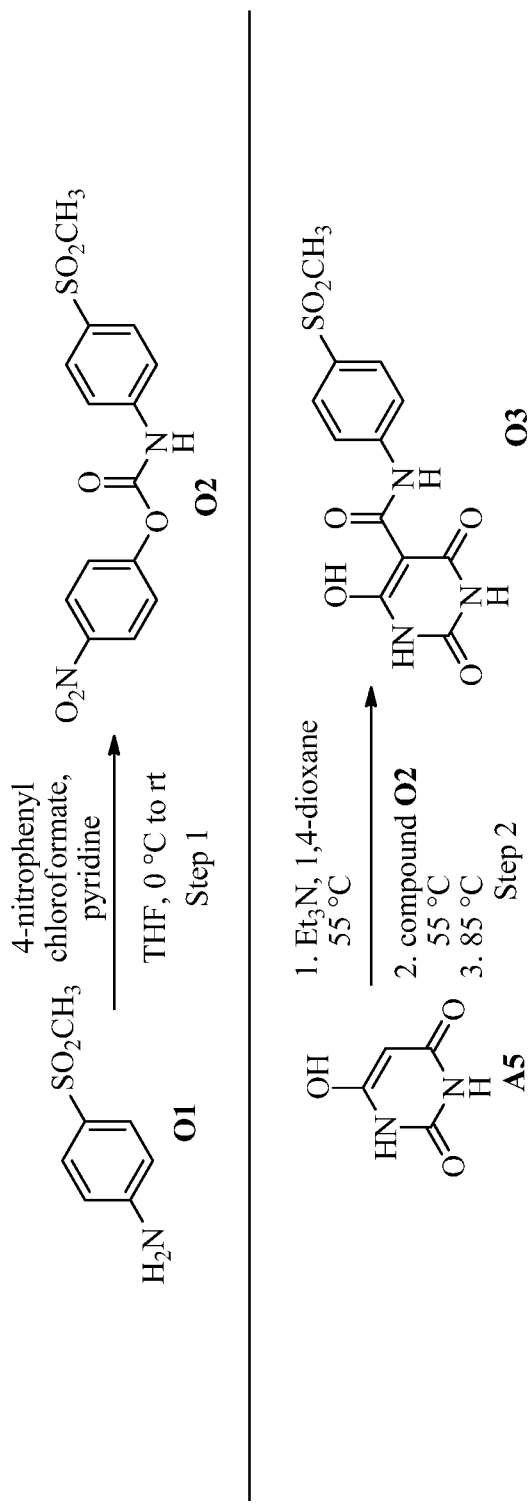
FIG. 27 illustrates synthesis of the compound represented by Formula (II$_b$), described in Example 21.

Preparation of 6-hydroxy-N-(4-(methylsulfonyl)phenyl)-2,4-dioxo-1,2,3,4-tetrahydropyrimidine-5-carboxamide (Formula IIb, shown as (O3) in FIG. 27). The following reaction steps correspond to the steps and compounds shown in FIG. 27.

Step One & Two. 6-Hydroxy-N-(4-(methylsulfonyl) phenyl)-2,4-dioxo-1,2,3,4-tetrahydropyrimidine-5-carboxamide (O3)

To a stirred solution of 4-nitrophenyl chloroformate (4.10 g, 20.3 mmol) in anhydrous THF (50 mL) was added a solution of compound O1 (3.43 g, 20.3 mmol) and pyridine (1.77 g, 22.4 mmol) in anhydrous THF (50 mL) dropwise over 10 min at 0° C. under nitrogen. After the addition was completed, the reaction was warmed to ambient temperature and stirred for 18 h to provide a solution of compound O2 in THF which was used directly in the subsequent step.

In a separate flask, to a suspension of barbituric acid A5 (2.56 g, 20.0 mmol) in anhydrous 1,4-dioxane (50 mL) was added a solution of triethylamine (2.03 g, 20.1 mmol) in anhydrous 1,4-dioxane (20 mL) dropwise over 25 min at 55° C. under nitrogen. After addition was completed, the mixture was stirred for 10 min. Then, to this mixture was added the compound O2 solution in THF dropwise over 20 min. The resulting mixture was heated to 85° C. for 4.5 h. After cooling to ambient temperature, 0.1 N_hydrochloric acid (400 mL) was added. The mixture was stirred for 25 min and filtered. The filter cake was washed with water (2×30 mL) and dried under high vacuum at 60° C. to afford compound 03 (3.72 g, 57%) as a white solid: $^1$H NMR (300 MHz, DMSO-d$_6$) δ 12.20-11.60 (br s, 2H), 11.79 (s, 1H), 7.93 (d, J=8.7 Hz, 2H), 7.81 (d, J=8.7 Hz, 2H), 3.21 (s, 3H); APCI MS, m/z 324 [M−H]$^-$.

Example 22

Figure 28:
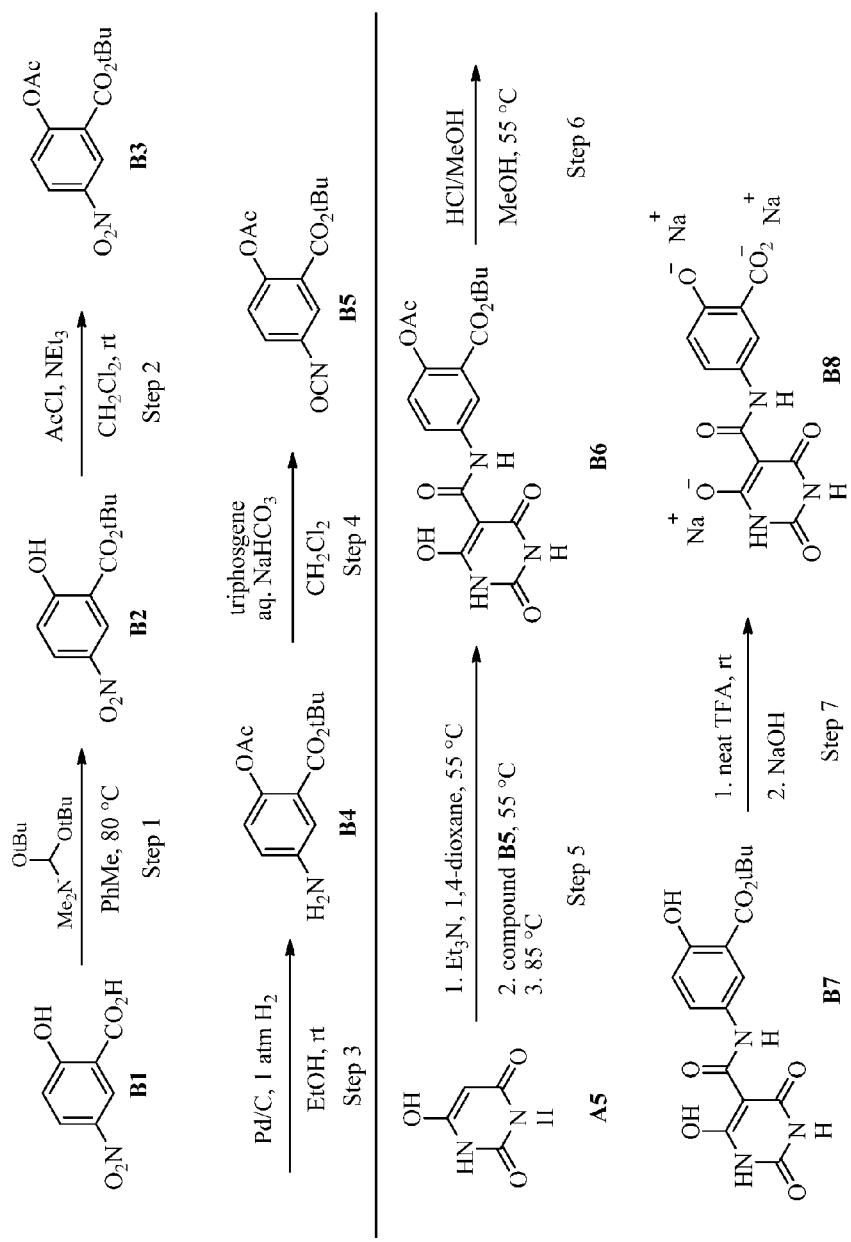
FIG. 28 illustrates synthesis of the compound represented by Formula (II$_f$) described in Example 22.

Preparation of Disodium 2-oxido-5-(6-oxido-2,4-dioxo-1,2,3,4-tetrahydropyrimidine-5-carboxamido)benzoate (shown as B8 in FIG. 28, Formula IIf). The following reaction steps correspond to the steps and compounds shown in FIG. 28.

Step One. tert-Butyl 2-hydroxy-5-nitrobenzoate (B2)

To a suspension of B1 (1.83 g, 10.0 mmol) in toluene (50 mL), at 80° C. and under a nitrogen atmosphere, was added 1,1-di-tert-butoxy-N,N-dimethylmethanamine (4.06 g, 20.0 mmol). After 0.5 h, additional 1,1-di-tert-butoxy-N,N-dimethylmethanamine (4.06 g, 20.0 mmol) was added to the reaction mixture. The mixture was stirred for 1 h and then concentrated under reduced pressure. The residue was dissolved in ethyl acetate (100 mL) and washed with water (5×10 mL), dried over anhydrous Na$_2$SO$_4$, filtered, and concentrated under reduced pressure to afford compound B2 (1.80 g, 77%) as a brown-yellow solid: $^1$H NMR (300 MHz, CDCl$_3$) δ 11.80 (s, 1H), 8.69 (d, J=2.7 Hz, 1H), 8.30 (dd, J=9.3, 3.0 Hz, 1H), 7.05 (d, J=9.3 Hz, 1H), 1.66 (s, 9H).

Step Two. tert-Butyl 2-acetoxy-5-nitrobenzoate (B3)

To an ice cold solution of B2 (1.80 g, 7.53 mmol) and triethylamine (2.1 mL, 15 mmol) in methylene chloride (15 mL), under a nitrogen atmosphere, was added acetyl chloride (0.81 mL, 11 mmol) in methylene chloride (10 mL) dropwise over 15 min. The reaction was warmed to ambient temperature and stirred for 20 h. After this time, the reaction mixture was concentrated under reduced pressure. The residue was dissolved in ethyl acetate (75 mL) and washed with water (3×75 mL), brine (75 mL), dried over anhydrous Na$_2$SO$_4$, filtered, and concentrated under reduced pressure. The residue was purified by flash column chromatography on silica gel eluting with 5-50% ethyl acetate/hexanes to afford compound B3 (1.98 g, 93%) as a white solid: $^1$H NMR (300 MHz, CDCl$_3$) δ 8.75 (d, J=2.7 Hz, 1H), 8.36 (dd, J=8.7, 2.7 Hz, 1H), 7.26 (d, J=2.7 Hz, 1H), 2.39 (s, 3H), 1.60 (s, 9H).

Step Three. tert-Butyl 2-acetoxy-5-aminobenzoate (B4)

A solution of compound B3 (1.00 g, 3.56 mmol) and 10% palladium on carbon (50% wet, 200 mg) in ethanol (15 mL) was stirred under 1 atmosphere of hydrogen at ambient temperature for 2 h. After this time, the reaction mixture was filtered through a short pad of diatomaceous earth and the filtrate was concentrated under reduced pressure. The residue was purified by flash column chromatography on silica gel eluting with 5-50% ethyl acetate/hexanes to afford compound B4 (720 mg, 81%) as a colorless oil: $^1$H NMR (500 MHz, CDCl$_3$, mixture of rotamers) δ 7.18 (d, J=3.0 Hz, 1H), 6.84 (s, 0.4H), 6.83 (s, 0.6H), 6.78 (d, J=3.0 Hz, 0.6H), 6.77 (d, J=3.0 Hz, 0.4H), 3.15 (br s, 2H), 2.29 (s, 3H), 1.55 (s, 9H).

Step Four. tert-Butyl 2-acetoxy-5-isocyanatobenzoate (B5)

To an ice cold solution of B4 (360 mg, 1.43 mmol) in anhydrous methylene chloride (15 mL) and satd. aq. sodium bicarbonate (15 mL), under a nitrogen atmosphere, was added a solution of triphosgene (170 mg, 0.57 mmol) in anhydrous methylene chloride (3 mL) directly to the methylene chloride layer. After the addition was completed, stirring was resumed and the reaction mixture was warmed to ambient temperature and stirred for 0.5 h. After this time, the organic layer was concentrated under reduced pressure. The residue was purified by flash column chromatography on silica gel eluting with 50% ethyl acetate/hexanes to afford compound B5 (310 mg, 77%) as an off-white solid: $^1$H NMR (300 MHz, CDCl$_3$, mixture of rotamers) δ 7.61 (d, J=4.5 Hz, 1H), 7.21 (d, J=4.5 Hz, 0.4H), 7.18 (d, J=0.6H), 7.02 (s, 0.6H), 7.00 (s, 0.4H), 2.33 (s, 3H), 1.55 (s, 9H).

Step Five. tert-Butyl 2-acetoxy-5-(6-hydroxy-2,4-dioxo-1,2,3,4-tetrahydropyrimidine-5-carboxamido) benzoate (B6)

To a suspension of barbituric acid A5 (141 mg, 1.10 mmol) in anhydrous 1,4-dioxane (3 mL), at 55° C. and under a nitrogen atmosphere, was added triethylamine (0.15 mL, 1.1 mmol). After 30 min, a solution of compound B5 (306 mg, 1.10 mmol) in anhydrous 1,4-dioxane (2 mL) was added dropwise over 25 min. The resulting mixture was heated to 85° C. for 3.5 h. After cooling to ambient temperature, 0.05

N hydrochloric acid (25 mL) was added and the mixture was stirred for 25 min. The solid was collected by vacuum filtration, rinsed with 1,4-dioxane (10 mL), methanol (10 mL) and dried to afford compound B6 (280 mg, 62%) as an off-white solid: $^1$H NMR (300 MHz, DMSO-$d_6$, mixture of rotamers) δ 11.58 (br s, 2H), 7.99-7.98 (m, 0.7H), 7.94 (d, J=3.0 Hz, 0.3H), 7.77-7.74 (m, 0.7H), 7.68-7.64 (m, 0.3H), 7.22 (d, J=8.7 Hz, 0.7H), 7.11 (d, J=8.7 Hz, 0.3H), 2.28-2.25 (m, 3H), 1.50 (s, 9H).

Step Six. tert-Butyl 2-hydroxy-5-(6-hydroxy-2,4-dioxo-1,2,3,4-tetrahydropyrimidine-5-carboxamido)benzoate (B7)

A suspension of compound B6 (101 mg, 0.249 mmol) in 1 N HCl in methanol (6 mL) was heated to 55° C., in a sealed tube, for 7 h. After this time, the reaction mixture was filtered and the filter cake was washed with methanol and dried to afford compound B7 (48 mg, 53%) as a white solid: $^1$H NMR (300 MHz, DMSO-$d_6$) δ 12.10-11.33 (m, 3H), 10.64 (s, 1H), 7.98-7.86 (m, 1H), 7.63-7.58 (m, 1H), 7.00 (d, J=9.0 Hz, 1H), 1.58 (s, 9H).

Step Seven. Sodium 2-oxido-5-(6-oxido-2,4-dioxo-1,2,3,4-tetrahydropyrimidine-5-carboxamido)benzoate (B8, Formula IIf)

A suspension of compound B7 (47 mg, 0.13 mmol) in TFA (2 mL) was stirred at ambient temperature for 7 h. After this time, the reaction mixture was filtered and the filter cake was washed with methanol and dried. A portion of the solid (24.5 mg) was suspended in 0.2 N NaOH (1.2 mL, 0.24 mmol) and water (1 mL). The suspension was gently heated with a heat gun and sonicated until the entire suspension dissolved. The solution was lyophilized to afford compound B8 (30 mg, 62%) as an off-white solid: $^1$H NMR (500 MHz, $D_2O$) δ 7.84 (d, J=2.5 Hz, 1H), 7.50 (dd, J=8.5, 2.5 Hz, 1H), 6.96 (d, J=8.5 Hz, 1H); ESI MS, m/z 306 [M−H]$^-$.

Example 23

Figure 29:
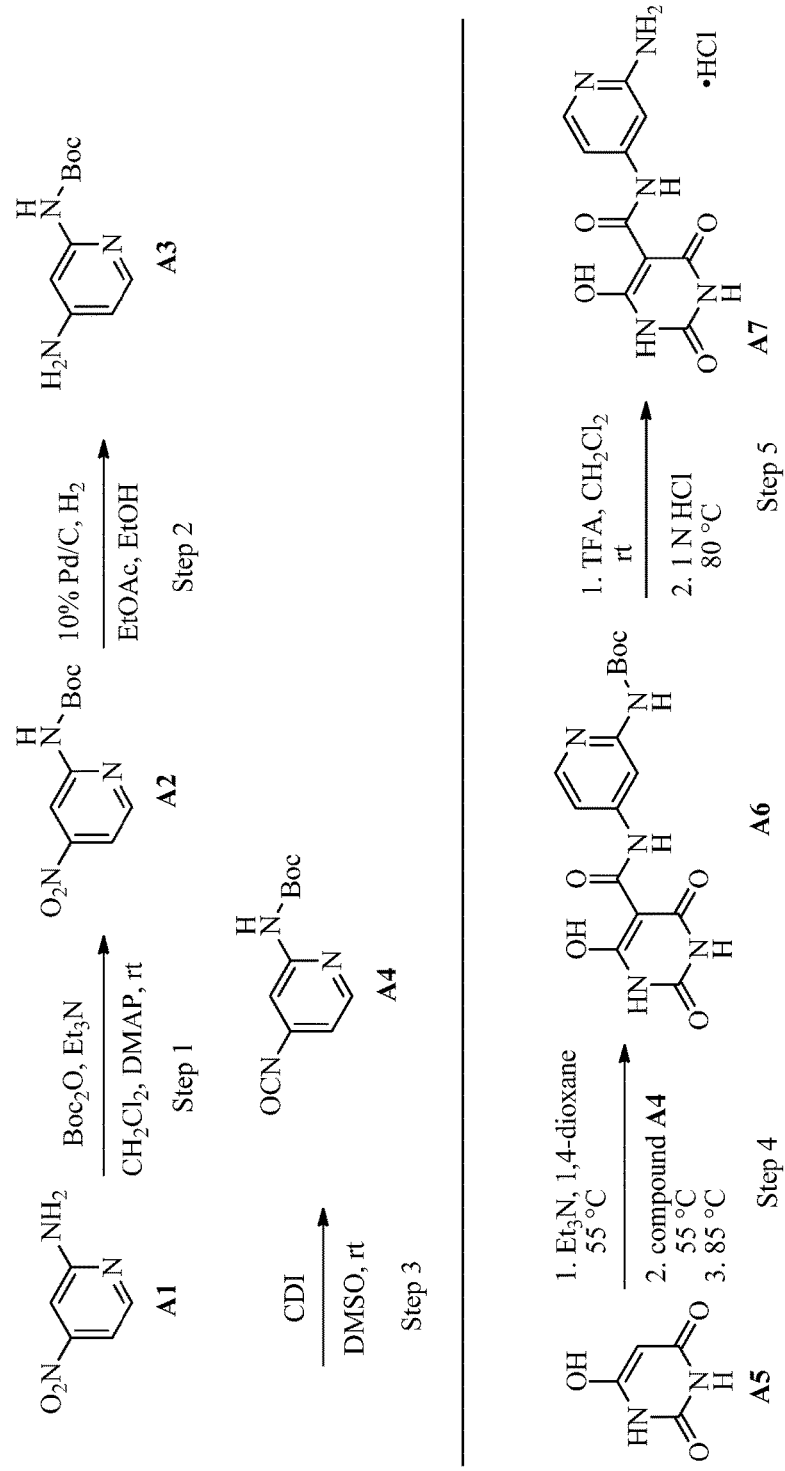
FIG. 29 illustrates synthesis of the compound represented by Formula (III$_c$) described in Example 23.

Preparation of N-(2-aminopyridin-4-yl)-6-hydroxy-2,4-dioxo-1,2,3,4-tetrahydropyrimidine-5-carboxamide (shown as A7 in FIG. 29, Formula IIIc). The following reaction steps correspond to the steps and compounds shown in FIG. 29.

Step One. tert-Butyl (4-nitropyridin-2-yl)carbamate (A2)

To a stirred solution of compound A1 (550 mg, 3.95 mmol), triethylamine (0.55 mL, 4.0 mmol) and 4-dimethylaminopyridine (241 mg, 3.95 mmol) in anhydrous dichloromethane (10 mL) was added a solution of di-tert-butyl dicarbonate (863 mg, 3.95 mmol) in anhydrous dichloromethane (4 mL). After 2.25 h, the reaction mixture was concentrated under reduced pressure. The residue was purified by flash column chromatography on silica gel eluting with 0-50% ethyl acetate/hexanes to afford compound A2 (563 mg, 60%) as a white solid: $^1$H NMR (500 MHz, $CDCl_3$) δ 8.77 (d, J=1.5 Hz, 1H), 8.47 (d, J=6.0 Hz, 1H), 7.98 (br s, 1H), 7.68 (dd, J=5.0, 1.5 Hz, 1H), 1.56 (s, 9H).

Step Two. tert-Butyl (4-aminopyridin-2-yl)carbamate (A3)

A suspension of compound A2 (560 mg, 2.34 mmol) and 10% palladium on carbon (50% wet, 150 mg) in ethanol (10 mL) and ethyl acetate (25 mL) was stirred under 1 atmosphere of hydrogen at ambient temperature for 3.75 h. After this time, the reaction mixture was filtered through a short pad of diatomaceous earth and the filtrate was concentrated under reduced pressure to afford compound A3 (460 mg, 94%) as a white solid: $^1$H NMR (500 MHz, DMSO-$d_6$) δ 9.15 (br s, 1H), 7.66 (d, J=5.5 Hz, 1H), 7.01 (d, J=2.0 Hz, 1H), 6.14 (dd, J=6.0, 2.5 Hz, 1H), 5.96 (br s, 2H), 1.45 (s, 9H).

Steps Three and Four. tert-Butyl (4-(6-hydroxy-2,4-dioxo-1,2,3,4-tetrahydropyrimidine-5-carboxamido)pyridin-2-yl)carbamate (A6)

To a stirred solution of compound A3 (460 mg, 2.19 mmol) in anhydrous DMSO (4 mL), at 0-5° C. and under a nitrogen atmosphere, was added 1,1'-carbonyldiimidazole (391 mg, 2.40 mmol). The reaction mixture was then stirred at ambient temperature for 1 h to provide a solution of compound A4 in DMSO which was used directly in the subsequent step.

In a separate flask, to a suspension of barbituric acid A5 (281 mg, 2.19 mmol) in anhydrous 1,4-dioxane (5 mL) was added triethylamine (0.30 mL, 2.19 mmol) at 55° C. under nitrogen. After the addition was completed, the mixture was stirred for 25 min. Then, to this mixture was added the compound A4 solution in DMSO dropwise over 0.5 h. The resulting mixture was heated to 80° C. for 40 min. After cooling to ambient temperature, water (20 mL) was added and the resulting solid was collected by vacuum filtration. The filter cake was washed with water (10 mL) and dried in vacuo to afford a crude product (154 mg, A6) as a white solid, which was used in the next step without further purification: ESI MS m/z 362 [M−H]$^-$.

Step Five. N-(2-aminopyridin-4-yl)-6-hydroxy-2,4-dioxo-1,2,3,4-tetrahydropyrimidine-5-carboxamide (A7, Formula IIIc)

To a suspension of compound A6 (150 mg, 0.413 mmol) in methylene chloride (2 mL) was added trifluoroacetic acid (2 mL). The solution was stirred at ambient temperature for 1 h. After this time, the reaction mixture was concentrated under reduced pressure to give a yellow solid. The solid was triturated with acetonitrile (5 mL), collected by vacuum filtration and then triturated with warm methanol (5 mL) and collected by filtration. The solid was then heated to 80° C. in 1 N HCl (20 mL) for 20 min. After this time, the suspension was cooled to 0° C. and the solid was collected by filtration and rinsed with water. The solid was dried under high vacuum at 80° C. to afford compound A7 (28.3 mg, 5% from A3) as an off-white solid: $^1$H NMR (300 MHz, TFA-d) δ 7.81 (d, J=7.2 Hz, 1H), 7.69 (d, J=1.8 Hz, 1H), 7.06 (dd, J=7.2, 2.1 Hz, 1H); ESI MS, m/z 264 [M+H]$^+$.

Example 24: Bioactivity Assays

The biological activities of compounds having structures represented by Formula ($I_c$), Formula ($I_g$), Formula ($I_b$) and Formula ($I_k$) were evaluated in two assays for xanthine oxidase and URAT1 activity.

Xanthine oxidase inhibition was determined using a standard fluorescence-based assay for xanthine oxidase activity (McHale A, Grimes H, Coughlan M P: Int J Biochem. 10:317-9, 1979) with minor variations. The procedure was internally standardized using allopurinol and DPI as controls for all experiments after determination of their optimal inhibitory concentrations. Experiments on test compounds were performed in triplicate in multi-well plates using 10 concentrations of each compound that ranged over a 3-fold dilution.

URAT1 (SLC22A12) activity was evaluated in a cellular uptake assay using a 96-well plate with stably transfected URAT-1/CHO cells. $^3$H-orotate was used as the test transport agent, which was measured in a liquid scintillation counter, using benzbromarone as a positive control, and DMSO and non-transfected CHO cells as negative controls (Solvo Biotechnology, Boston, Mass.). Over 7 concentrations (range, 0.01 to 150 µM), a semi-log plot (percent relative transport of oratate vs. time) was generated to determine the concentration at which 50% inhibition was observed (i.e., the IC50).

The results of these assays are shown in the following Table:

| Compound | URAT1 IC$_{50}$ (µM) | Xanthine Oxidase IC$_{50}$ (µM) |
| --- | --- | --- |
| Formula (I$_c$) | 5.83 | 5.60 |
| Formula (I$_g$) | 3.55 | 1.92 |
| Formula (I$_h$) | 1.79 | 5.97 |
| Formula (I$_k$) | 5.30 | 14.26 |
| Allopurinol | >300 | 3.5 |
| Lesinurad | 18.6 | >300† |

†Estimate from public presentation Proc EULAR Abstract #THU0357, 2008

Each of the Formula (I$_c$), Formula (I$_g$) and Formula (I$_h$) compounds is a highly potent bifunctional compound, inhibiting both URAT1 and XO with an IC50 of less than 10 µM. The Formula (I$_k$) compound is only slightly less potent with respect to inhibition of XO than the other compounds. By way of comparison, allopurinol has an IC50 for XO of 2.13 µM and an IC50 for URAT1 of >300 µM. Lesinurad has an IC50 for XO of >300 µM and an IC50 for URAT1 of about 53 µM. In contrast, the compounds of the invention are not only bifunctional, but they are substantially more potent inhibitors of URAT1.

The compounds described herein have different relative levels of XO and URAT1 inhibitory activity. Those with higher XO inhibitory activity relative to their URAT1 inhibitory activity may be desirable for use in certain treatment situations, since it is generally accepted that decreasing UA production is important for a drug to be considered "first-line" treatment, particularly as a monotherapy. For example, in such situations, Formula I$_g$ may be deemed somewhat more desirable than Formula I$_k$. In other treatment situations, compounds having higher URAT1 inhibitory activity relative to XO inhibitory activity may be considered more appropriate. The practitioner, guided by the present disclosure, will be able to select particular compounds as appropriate for a specific use based on the level of skill in the art.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A compound selected from the group consisting of compounds having a structure represented by

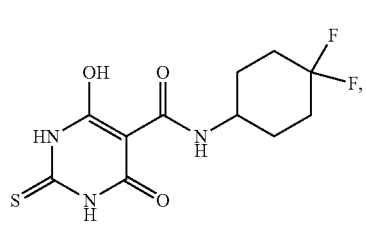

Formula (I$_a$)

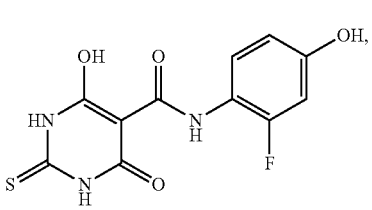

Formula (I$_c$)

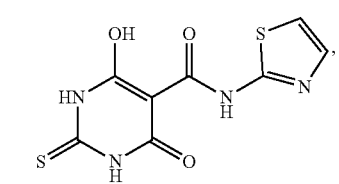

Formula (I$_d$)

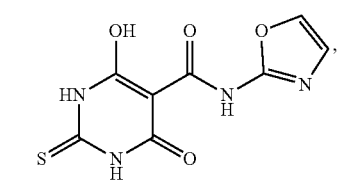

Formula (I$_e$)

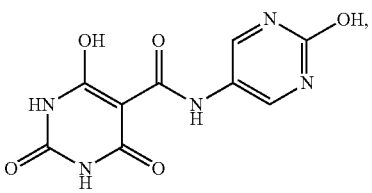

Formula (I$_f$)

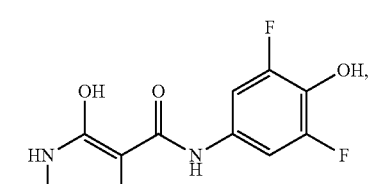

Formula (I$_g$)

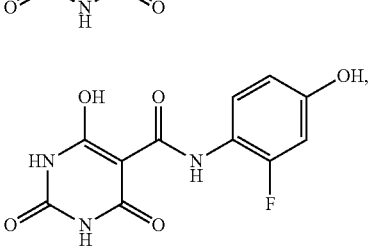

Formula (I$_h$)

-continued
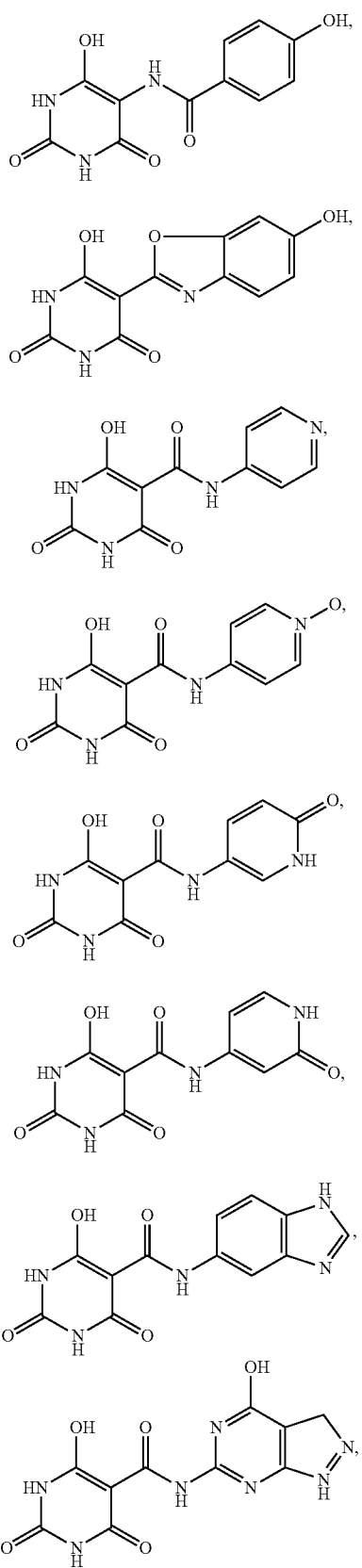
and tautomers thereof.
2. The compound according to claim 1 which has a structure represented by
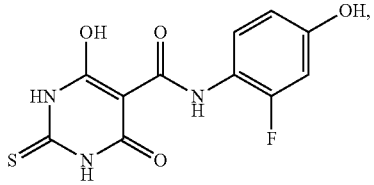
or a tautomer thereof.
3. A compound selected from the group consisting of compounds having a structure represented by
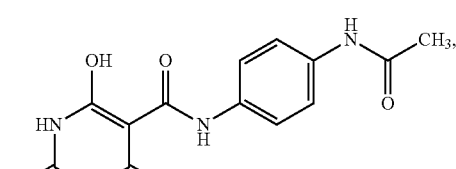
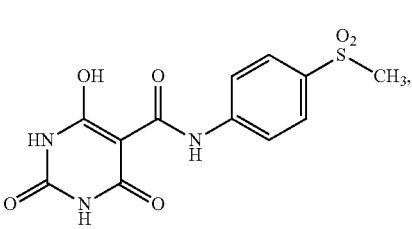

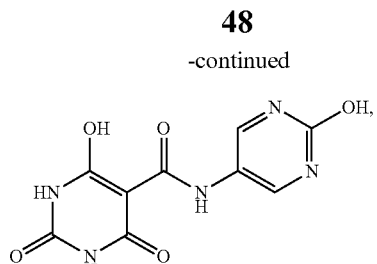
Formula (II$_c$)

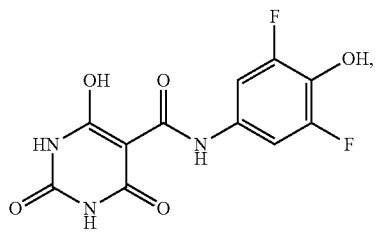
Formula (II$_d$)

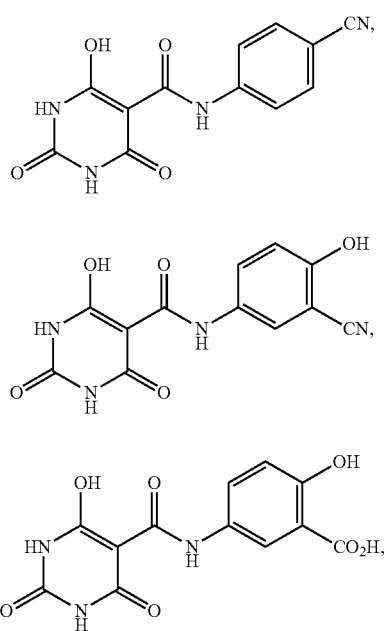
Formula (II$_f$)

and tautomers thereof.

4. A pharmaceutical composition comprising a compound selected from the group consisting of compounds having a structure represented by:

Formula (I$_a$)

Formula (I$_b$)

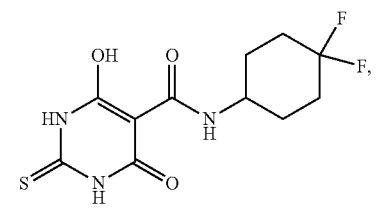
Formula (I$_c$)

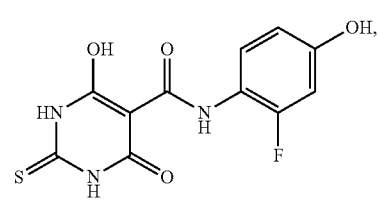
Formula (I$_d$)

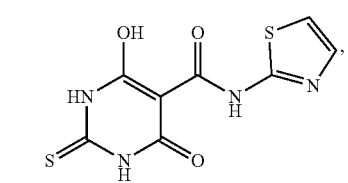
Formula (I$_e$)

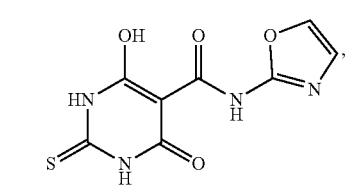

Formula (I$_f$)

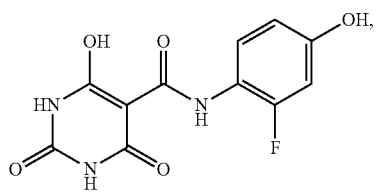
Formula (I$_g$)

Formula (I$_h$)

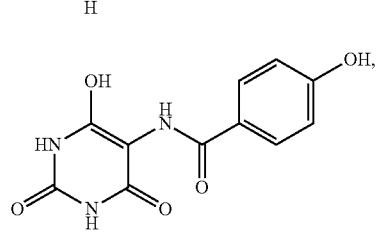
Formula (I$_i$)

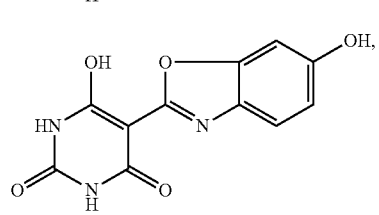
Formula (I$_j$)

Formula (I$_k$)

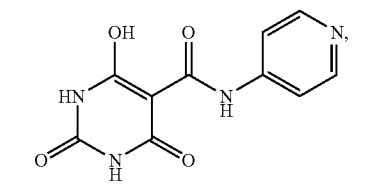
Formula (I$_l$)

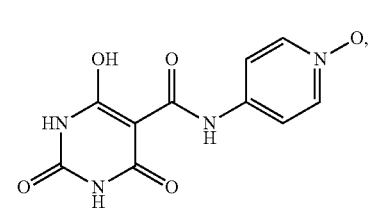
Formula (I$_m$)

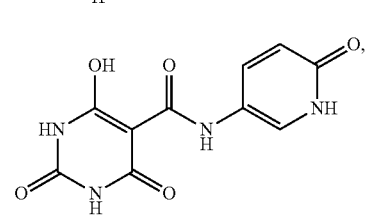

Formula (I_n)
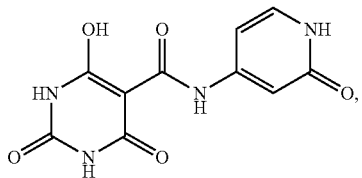

Formula (I_o)
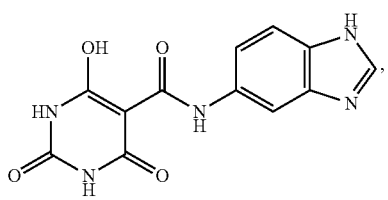

Formula (I_p)
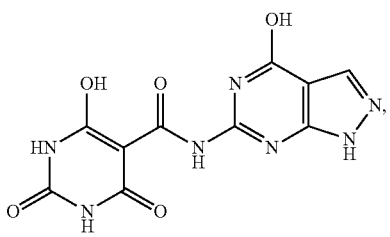

Formula (II_a)
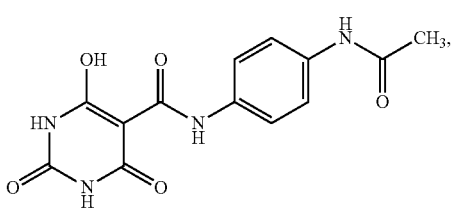

Formula (II_b)
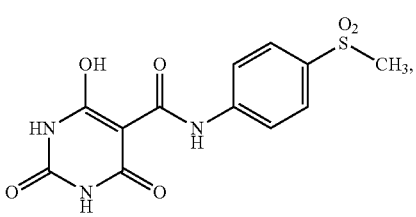

Formula (II_c)
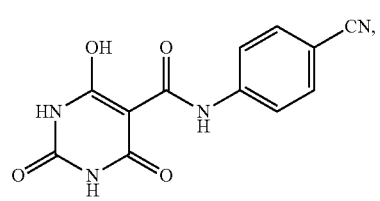

Formula (II_d)
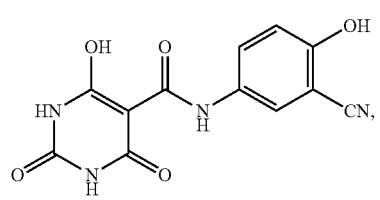

Formula (II_f)
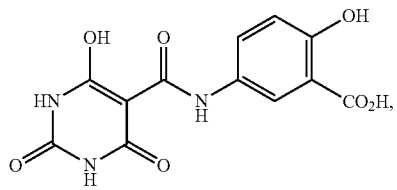

tautomers thereof, and
combinations of any of the foregoing compounds; and
a pharmaceutically acceptable carrier.

5. The pharmaceutical composition according to claim 4, wherein the compound, or combination thereof, is selected from the group consisting of compounds having a structure represented by Formula (I_g)
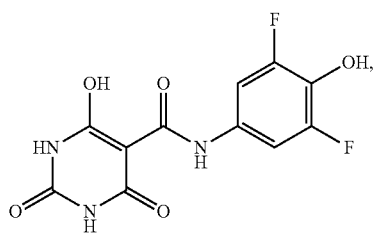

Formula (I_k)
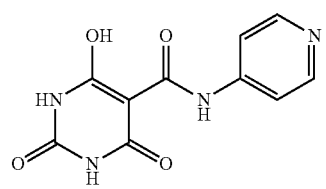

and tautomers thereof.

6. A method for reducing uric acid levels, or preventing elevation of uric acid levels, in blood or serum of a subject comprising administering to a subject in need thereof a pharmaceutical composition according to claim 4 in an amount effective to reduce blood or serum uric acid levels or to prevent elevation of blood or serum uric acid levels.

7. The method according to claim 6, wherein administering the pharmaceutical composition treats a disorder of uric acid metabolism caused by, or associated with, hyperuricemia.

8. The method of claim 7 wherein the disorder of uric acid metabolism is selected from the group consisting of gout, hyperuricemia, tumor lysis syndrome, kidney disease, arthritis, kidney stones, kidney failure, urolithiasis, plumbism, hyperparathyroidism, psoriasis, inborn genetic errors of metabolism, sarcoidosis or cardiovascular disease.

9. The method according to claim 8, wherein the disorder of uric acid metabolism is gout.

10. The method according to claim 6, wherein a daily dose of about 20 to about 1,500 mg/m²/day, or about 20 to about 150 mg/m²/day, of the compound or combination thereof is administered.

11. The method according to claim 10, wherein the pharmaceutical composition is administered by injection, infusion, or oral administration.

12. The method according to claim 11, wherein the pharmaceutical composition is administered by intravenous infusion or bolus injection.

13. The method according to claim 6, wherein the compound, or combination thereof, is selected from the group consisting of compounds having a structure represented by Formula (I_g)

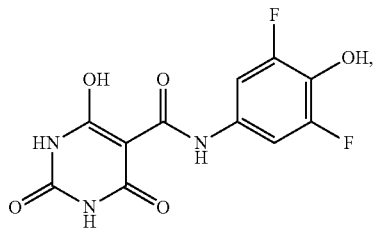

-continued

Formula (I_k)

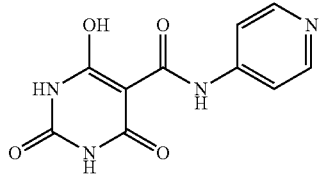

and tautomers thereof.

14. The pharmaceutical composition according to claim 4 which is formulated for extended or controlled release of the compound or combination thereof.

15. The pharmaceutical composition according to claim 4, wherein the pharmaceutically acceptable carrier is selected from the group consisting of water or saline, a solvent, a dispersing agent, a coating, a surfactant, a preservative, an emulsion, an alcohol, a polyol, and an isotonic agent.

* * * * *